12) United States Patent
Cebe et al.

(10) Patent No.: US 11,692,046 B2
(45) Date of Patent: Jul. 4, 2023

(54) FGF21 MIMETIC ANTIBODIES AND USES THEREOF

(71) Applicant: Novartis AG, Basel (CH)

(72) Inventors: Regis Cebe, Saint-Louis (FR); Stephane Olland, Arlington, MA (US); David Langdon Yowe, Belmont, MA (US)

(73) Assignee: Novartis AG, Basel (CH)

( * ) Notice: Subject to any disclaimer, the term of this patent is extended or adjusted under 35 U.S.C. 154(b) by 206 days.

(21) Appl. No.: 17/127,600

(22) Filed: Dec. 18, 2020

(65) Prior Publication Data
US 2021/0171659 A1 Jun. 10, 2021

Related U.S. Application Data

(62) Division of application No. 15/890,302, filed on Feb. 6, 2018, now Pat. No. 10,899,844.

(60) Provisional application No. 62/456,609, filed on Feb. 8, 2017.

(51) Int. Cl.
C07K 16/40 (2006.01)
C07K 16/28 (2006.01)
A61K 39/395 (2006.01)
A61K 39/00 (2006.01)

(52) U.S. Cl.
CPC ........ C07K 16/40 (2013.01); A61K 39/39591 (2013.01); C07K 16/2863 (2013.01); A61K 2039/505 (2013.01); A61K 2039/545 (2013.01); C07K 2317/24 (2013.01); C07K 2317/75 (2013.01); C07K 2317/92 (2013.01); C07K 2317/94 (2013.01)

(58) Field of Classification Search
None
See application file for complete search history.

(56) References Cited

U.S. PATENT DOCUMENTS

| 8,372,952 | B2 | 2/2013 | Smith et al. |
| 8,697,369 | B2 | 4/2014 | Suzuki et al. |
| 8,722,622 | B2 | 5/2014 | Das et al. |
| 9,085,626 | B2 | 7/2015 | Sonoda et al. |
| 9,284,378 | B2 | 3/2016 | Hu et al. |
| 9,580,507 | B2 | 2/2017 | Korman et al. |
| 2002/0018749 | A1* | 2/2002 | Hudson ............ C07K 16/40 424/1.49 |
| 2010/0184665 | A1 | 7/2010 | Suzuki et al. |
| 2011/0135657 | A1 | 6/2011 | Hu et al. |
| 2011/0150901 | A1 | 6/2011 | Smith et al. |
| 2012/0282279 | A1 | 11/2012 | Das et al. |
| 2012/0294861 | A1 | 11/2012 | Sonoda et al. |
| 2012/0328616 | A1 | 12/2012 | Li et al. |
| 2013/0129725 | A1 | 5/2013 | Fachini et al. |
| 2013/0197191 | A1 | 8/2013 | Smith et al. |
| 2014/0142023 | A1 | 5/2014 | Sommerfeld et al. |
| 2014/0189893 | A1 | 7/2014 | Li et al. |
| 2014/0206023 | A1 | 7/2014 | Gao et al. |
| 2015/0210764 | A1 | 7/2015 | Mondal et al. |
| 2015/0218276 | A1 | 8/2015 | Chen et al. |
| 2015/0376283 | A1 | 12/2015 | Sonoda et al. |
| 2016/0108123 | A1 | 4/2016 | Freeman et al. |

FOREIGN PATENT DOCUMENTS

| EP | 2548570 A1 | 1/2013 |
| EP | 2711375 A1 | 3/2014 |
| EP | 2679234 A3 | 4/2014 |
| EP | 2510009 B1 | 4/2017 |
| WO | 2007005874 A2 | 1/2007 |
| WO | 2008123625 A1 | 10/2008 |
| WO | 2011068893 A1 | 6/2011 |
| WO | 2011071783 A1 | 6/2011 |
| WO | 2011130417 A3 | 3/2012 |
| WO | 2012059873 A2 | 5/2012 |
| WO | 2012154263 A1 | 11/2012 |
| WO | 2012158704 A1 | 11/2012 |
| WO | 2012177481 A2 | 12/2012 |
| WO | 2013010780 A1 | 1/2013 |
| WO | 2012170438 A3 | 4/2013 |
| WO | 2014149699 A1 | 9/2014 |
| WO | 2015100366 A1 | 7/2015 |
| WO | 2015112886 A3 | 10/2015 |
| WO | 2015148708 A1 | 10/2015 |
| WO | 2016061142 A1 | 4/2016 |
| WO | 2017021893 A1 | 2/2017 |
| WO | 2017025918 A1 | 2/2017 |

OTHER PUBLICATIONS

Foltz, et al, "Treating Diabetes and obesity with an FGF21-Mimetic Antibody Activating the 13Klotho/FGFR1c Receptor Complex", Science Translational Medicine, 4(162):1-10 (2012).
Gorar, et al., "Serum fibroblast growth factor 21 levels in polycystic ovary syndrome", Gynecological Endocrinology, 26(11):819-826 (2010).
Reitman, et al., "FGF21 Mimetic Shows Therapeutic Promise", Cell Metabolism, 18(3):307-309 (2013).
Siegel, et al, "A C/T single nucleotide polymorphism at the tyrosine kinase domain of the insulin receptor gene is associated with polycystic ovary syndrome", Fertility and Sterility, 78(6):1240-1243 (2002).
Stein, et al., "Serum fibroblast growth factor 21 levels in gestations diabetes mellitus in relation to insulin resistance and dyslipidemia", Metabolism Clinical and experimental 59:33-31 (2010).
Tucci, et al, "Evidence for Association of Polycystic Ovary Syndrome in Caucasian Women with a Marker at the Insulin Receptor Gene Locus", Journal of Clinical Endocrinology & Metabolism, 86(1):446-449 (2001).
Maksimov et al., "Modern drugs for pharmacotherapy of obesity and metabolic syndrome," (Review), Sechenovsky Vestnik. 4(26):64-75 (2016).
Decision to Grant issued in Russian Patent Application No. 2019127917 dated Apr. 21, 2022 (21 pages).

* cited by examiner

Primary Examiner — Marianne P Allen
(74) Attorney, Agent, or Firm — Clark & Elbing LLP

(57) ABSTRACT

The present disclosure relates to monoclonal antibodies and antigen-binding fragments thereof that bind to human β-klotho, and pharmaceutical compositions and methods of treatment comprising the same.

13 Claims, 11 Drawing Sheets

Specification includes a Sequence Listing.

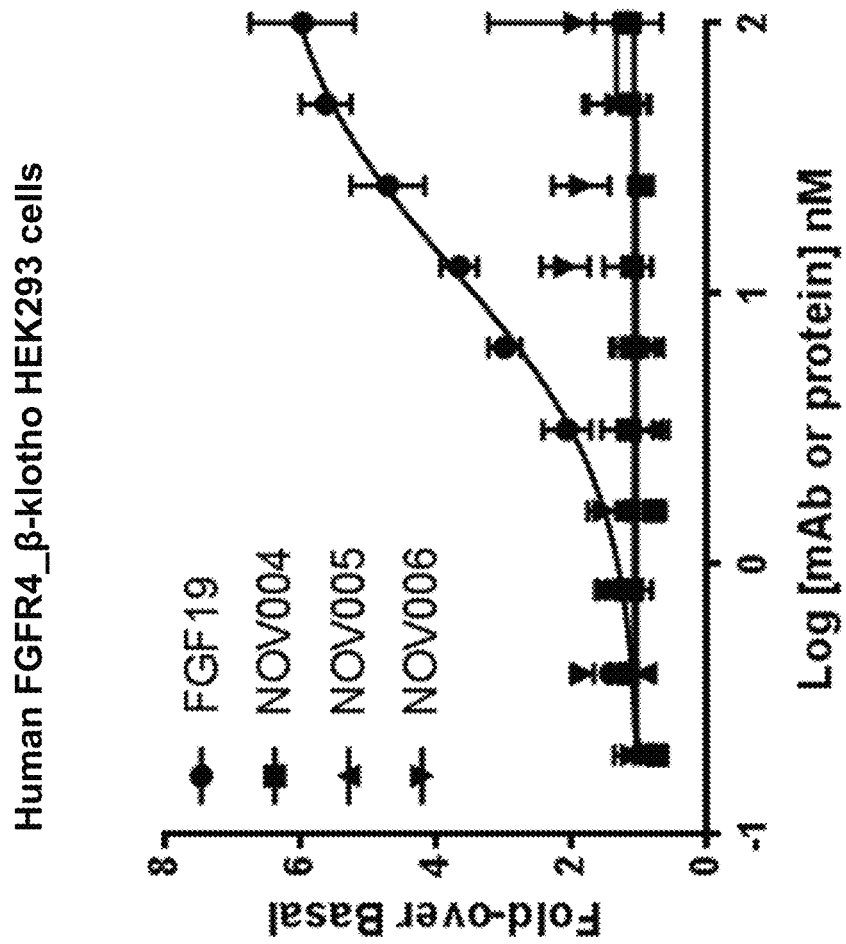

SEQUENCE LISTING

<160> NUMBER OF SEQ ID NOS: 64

<210> SEQ ID NO 1
<211> LENGTH: 209
<212> TYPE: PRT
<213> ORGANISM: Homo sapiens

<400> SEQUENCE: 1

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 2
<211> LENGTH: 938
<212> TYPE: DNA
<213> ORGANISM: Homo sapiens

<400> SEQUENCE: 2
ctgtcagctg aggatccagc cgaaagagga gccaggcact caggccacct gagtctactc    60
acctggacaa ctggaatctg caccaattc taaaccactc agcttctccg agctcacacc    120
ccggagatca cctgaggacc cgagccattg atggactcgg acgagaccgg gttcgagcac   180
tcaggactgt gggtttctgt gctggctggt cttctgctgg gagcctgcca ggcacacccc   240
atccctgact ccagtcctct cctgcaattc gggggccaag tccggcagcg gtacctctac   300
acagatgatg cccagcagac agaagcccac ctggagatca ggaggatgg acggtgggg    360 ggcgctgctg accagagccc cgaaagtctc ctgcagctga agccttgaa gccgggagtt    420 attcaaatct tgggagtcaa gacatccagg ttcctgtgcc agcggccaga tggggccctg   480
tatggatcgc tccactttga ccctgaggcc tgcagcttcc gggagctgct tcttgaggac   540
ggatacaatg tttaccagtc cgaagcccac ggcctcccgc tgcacctgcc agggaacaag   600

| | | |
|---|---|---|
| tccccacacc gggaccctgc accccgagga ccagctcgct tcctgccact accaggcctg | 660 |
| cccccgcac tcccggagcc acccggaatc ctggccccc agcccccga tgtgggctcc | 720 |
| tcggaccctc tgagcatggt gggaccttcc cagggccgaa gccccagcta cgcttcctga | 780 |
| agccagaggc tgtttactat gacatctcct ctttatttat taggttattt atcttattta | 840 |
| ttttttatt tttcttactt gagataataa agagttccag aggagaaaaa aaaaaaaaaa | 900 |
| aaaaaaaaaa aaaaaaaaaa aaaaaaaaaa aaaaaaaa | 938 |

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Tyr Ser Ile Thr Ser Gly Tyr Thr Trp His
1               5                   10

<210> SEQ ID NO 7
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Tyr Ile His Tyr Ser Val Tyr Thr Asn Tyr Asn Pro Ser Leu Lys Ser
1               5                   10                  15

<210> SEQ ID NO 8
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Arg Thr Thr Ser Leu Glu Arg Tyr Phe Asp Val
1               5                   10

```
<210> SEQ ID NO 9
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ser Gly Tyr Thr Trp His
1               5

<210> SEQ ID NO 10
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Tyr Ser Ile Thr Ser Gly Tyr
1               5

<210> SEQ ID NO 11
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

His Tyr Ser Val Tyr
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Tyr Ser Ile Thr Ser Gly Tyr Thr
1               5

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ile His Tyr Ser Val Tyr Thr
1               5

<210> SEQ ID NO 14
<211> LENGTH: 13
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic peptide"

<400> SEQUENCE: 14

Ala Arg Arg Thr Thr Ser Leu Glu Arg Tyr Phe Asp Val
1               5                   10

<210> SEQ ID NO 15
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Thr Trp His Trp Ile Arg Gln His Pro Gly Lys Gly Leu Glu Trp
        35                  40                  45

Ile Gly Tyr Ile His Tyr Ser Val Tyr Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Thr Thr Ser Leu Glu Arg Tyr Phe Asp Val Trp Gly Gln
            100                 105                 110

Gly Thr Leu Val Thr Val Ser Ser
        115                 120

<210> SEQ ID NO 16
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
caagtgcagc tgcaggaatc tggccctggc ctggtcaagc ctagccagac cctgtccctg     60
acctgcaccg tgtccggcta ctccatcacc tccggctaca cctggcactg gatccggcag    120
caccccggca agggcctgga atggatcggc tacatccact actccgtgta caccaactac    180
aaccccagcc tgaagtccag agtgaccatc tcccgggaca cctccaagaa ccagttctcc    240
ctgaagctgt cctccgtgac cgccgctgac accgccgtgt actactgcgc cagacggacc    300
acctccctgg aacggtactt cgacgtgtgg ggccagggca ccctggtcac cgtgtcctct    360

<210> SEQ ID NO 17
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Thr Trp His Trp Ile Arg Gln His Pro Gly Lys Gly Leu Glu Trp
        35                  40                  45

Ile Gly Tyr Ile His Tyr Ser Val Tyr Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Thr Thr Ser Leu Glu Arg Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ala Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Ala Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

```
                        405                 410                 415
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 18
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
caagtgcagc tgcaggaatc tggccctggc ctggtcaagc ctagccagac cctgtccctg      60
acctgcaccg tgtccggcta ctccatcacc tccggctaca cctggcactg gatccggcag     120
caccccggca agggcctgga atggatcggc tacatccact actccgtgta caccaactac     180
aaccccagcc tgaagtccag agtgaccatc tcccgggaca cctccaagaa ccagttctcc     240
ctgaagctgt cctccgtgac cgccgctgac accgccgtgt actactgcgc cagacggacc     300
acctccctgg aacggtactt cgacgtgtgg ggccagggca cctggtcac cgtgtcctct     360 gcttccacca agggcccctc cgtgttccct ctggccccct tccagcaagt cacctctggc     420
ggcaccgccg ctctgggctg cctcgtgaag gactacttcc ccgagcccgt gaccgtgtcc     480
tggaactctg gcgccctgac ctccggcgtg cacaccttcc ctgccgtgct gcagtcctcc     540
ggcctgtact ccctgtccag cgtcgtgacc gtgccctcca gctctctggg cacccagacc     600
tacatctgca acgtgaacca caagccctcc aacaccaaag tggacaagcg ggtggaaccc     660
aagtcctgcg acaagaccca cacctgtcct cctgccctg cccctgagct gctgggcgga     720
ccttccgtgt tcctgttccc tccaaagccc aaggacaccc tgatgatctc ccggacccct     780
gaagtgacct gcgtggtggt ggccgtgtcc cacgaggatc ccgaagtgaa gttcaattgg     840
tacgtggacg gcgtggaagt gcacaacgcc aagaccaagc cagagagga acagtacaac     900 tccacctacc gggtggtgtc cgtgctgacc gtgctgcacc aggactggct gaacggcaaa     960
gagtacaagt gcaaagtgtc caacaaggcc ctggccgctc ccatcgaaaa gaccatctcc    1020
aaggccaagg gccagccccg cgagcccaa gtgtacacac tgcctcccag ccggagag       1080 atgaccaaga atcaagtgtc cctgacatgt ctggtcaagg gcttctaccc tagcgatatc    1140
gccgtggaat gggagtccaa cggccagcct gagaacaact acaagaccac ccctcccgtg    1200
ctggactccg acggctcatt cttcctgtac tccaagctga ccgtggacaa gtcccggtgg    1260
cagcagggca acgtgttctc ctgctccgtg atgcacgagg ccctgcacaa ccactacacc    1320
cagaagtccc tgagcctgtc ccctggcaag                                    1350

<210> SEQ ID NO 19
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 19

Gln Ala Ser Gln Asp Ile Ser Asn Tyr Leu Asn
1               5                   10

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Tyr Thr Ser Arg Leu Gln Ser
1               5

<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln Gln Gly Asn Thr Leu Pro Tyr Thr
1               5

<210> SEQ ID NO 22
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Gln Asp Ile Ser Asn Tyr
1               5

<210> SEQ ID NO 23
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Tyr Thr Ser
1

<210> SEQ ID NO 24
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Asn Thr Leu Pro Tyr
1               5
```

```
<210> SEQ ID NO 25
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gln Asp Ile Ser Asn Tyr
1               5

<210> SEQ ID NO 26
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Ala Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gln Gly Thr Lys Leu Glu Ile Lys
            100                 105

<210> SEQ ID NO 27
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
gacatccaga tgacccagag cccgtcgtcc ctctccgctt ccgtgggaga tagagtgacc      60
atcacctgtc aagccagcca ggatatttca aactacctga attggtacca gcagaagccg    120
gggaaggctc ccaagttgct catctactac acatcgaggc tgcagtccgg cgtgcccagc    180
cggttctccg gtccggatc aggcgccgac tataccttca ccatttcctc cctgcaaccg     240
gaggacattg ccacttactt ctgccaacaa gggaacaccc tgccctacac tttcggacaa    300
ggaactaagc tggaaatcaa g                                              321

<210> SEQ ID NO 28
<211> LENGTH: 214
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Ala Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 29
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29

```
gacatccaga tgacccagag cccctccagc ctgtccgcct ccgtgggcga cagagtgacc    60
atcacctgtc aggcctccca ggacatctcc aactacctga ctggtatca gcagaagccc   120
ggcaaggccc ctaagctgct gatctactac acctcccggc tgcagtccgg cgtgccctcc   180
agattctccg gctctggctc tggcgccgac tacaccttca ccatctccag cctgcagccc   240
gaggatatcg ctacctactt ctgtcagcaa ggcaacaccc tgccctacac cttcggccag   300
ggcaccaagc tggaaatcaa gcgtacggtg gccgctccct ccgtgttcat cttcccaccc   360
tccgacgagc agctgaagtc cggcaccgcc tccgtcgtgt gcctgctgaa caacttctac   420
cctcgcgagg ccaaagtgca gtggaaagtg gacaacgccc tgcagagcgg caactcccag   480
gaatccgtca ccgagcagga ctccaaggac agcacctact ccctgtcctc caccctgacc   540
ctgtccaagg ccgactacga gaagcacaaa gtgtacgcct gcgaagtgac ccaccagggc   600
```

```
ctgtccagcc ccgtgaccaa gtccttcaac cggggcgagt gc                    642
```

<210> SEQ ID NO 30
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30

```
caagtgcagc tgcaggaatc tggccctggc ctggtcaagc ctagccagac cctgtccctg      60
acctgcaccg tgtccggcta ctccatcacc tccggctaca cctggcactg gatccggcag     120
caccccggca agggcctgga atggatcggc tacatccact actccgtgta caccaactac     180
aaccccagcc tgaagtccag agtgaccatc tcccgggaca cctccaagaa ccagttctcc     240
ctgaagctgt cctccgtgac cgccgctgac accgccgtgt actactgcgc cagacggacc     300
acctccctgg aacggtactt cgacgtgtgg ggccagggca cctggtcac cgtgtcctct      360
gcttccacca agggcccctc cgtgttccct ctggcccctt ccagcaagtc cacctctggc     420
ggcaccgccg ctctgggctg cctcgtgaag gactacttcc ccgagcccgt gaccgtgtcc     480
tggaactctg gcgccctgac ctccggcgtg cacaccttcc ctgccgtgct gcagtcctcc     540
ggcctgtact ccctgtccag cgtcgtgacc gtgccctcca gctctctggg cacccagacc     600
tacatctgca acgtgaacca caagccctcc aacaccaaag tggacaagcg ggtggaaccc     660
aagtcctgcg acaagaccca cacctgtcct cctgccctg ccctgagct gctgggcgga      720
ccttccgtgt tcctgttccc tccaaagccc aaggacaccc tgatgatctc ccggaccct     780
gaagtgacct gcgtggtggt ggccgtgtcc cacgaggatc ccgaagtgaa gttcaattgg     840
tacgtggacg gcgtggaagt gcacaacgcc aagaccaagc cagagagga cagtacaac      900
tccacctacc gggtggtgtc cgtgctgacc gtgctgcacc aggactggct gaacggcaaa     960
gagtacaagt gcaaagtgtc caacaaggcc ctggccgctc catcgaaaa gaccatctcc     1020
aaggccaagg gccagccccg cgagcccaa gtgtacacac tgcctcccag ccgggaagag     1080
atgaccaaga tcaagtgtc cctgacatgt ctggtcaagg gcttctaccc tagcgatatc     1140
gccgtggaat gggagtccaa cggccagcct gagaacaact acaagaccac ccctcccgtg     1200
ctggactccg acggctcatt cttcctgtac tccaagctga ccgtggacaa gtcccggtgg     1260
cagcagggca cgtgttctc ctgctccgtg atgcacgagg ccctgcacaa ccactacacc     1320
cagaagtccc tgagcctgtc ccctggcaag                                      1350
```

<210> SEQ ID NO 31
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 31

```
Arg Ala Ser Gln Asp Ile Ser Asn Tyr Leu Asn
1               5                   10
```

<210> SEQ ID NO 32
<211> LENGTH: 107

-continued

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
50                  55                  60

Ser Gly Ser Gly Ala Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys
            100                 105

<210> SEQ ID NO 33
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
gagatcgtga tgacccagtc ccctgccacc ctgtccctga gccctggcga gagagccacc    60
ctgagctgcc gggcctccca ggacatctcc aactacctga actggtatca gcagaagccc   120
ggccaggccc ctcggctgct gatctactac acctcccggc tgcagtccgg catccctgcc   180
agattctccg gctctggctc tggcgccgac tacaccctga ccatctccag cctgcagccc   240
gaggacttcg ccgtgtactt ctgtcagcaa ggcaacaccc tgccctacac cttcggccag   300
ggcaccaagc tggaaatcaa g                                              321

<210> SEQ ID NO 34
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
50                  55                  60

Ser Gly Ser Gly Ala Asp Tyr Thr Leu Thr Ile Ser Ser Leu Gln Pro

Glu Asp Phe Ala Val Tyr Phe Cys Gln Gln Gly Asn Thr Leu Pro Tyr
65                  70                  75                  80

Thr Phe Gly Gln Gly Thr Lys Leu Glu Ile Lys Arg Thr Val Ala Ala
            85                  90                  95

Pro Ser Val Phe Ile Phe Pro Pro Ser Asp Glu Gln Leu Lys Ser Gly
        100                 105                 110

Thr Ala Ser Val Val Cys Leu Leu Asn Asn Phe Tyr Pro Arg Glu Ala
    115                 120                 125

Lys Val Gln Trp Lys Val Asp Asn Ala Leu Gln Ser Gly Asn Ser Gln
130                 135                 140

Glu Ser Val Thr Glu Gln Asp Ser Lys Asp Ser Thr Tyr Ser Leu Ser
145                 150                 155                 160

Ser Thr Leu Thr Leu Ser Lys Ala Asp Tyr Glu Lys His Lys Val Tyr
            165                 170                 175

Ala Cys Glu Val Thr His Gln Gly Leu Ser Ser Pro Val Thr Lys Ser
        180                 185                 190

Phe Asn Arg Gly Glu Cys
    195                 200                 205

210

<210> SEQ ID NO 35
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
gagatcgtga tgacccagtc ccctgccacc ctgtccctga gccctggcga gagagccacc    60
ctgagctgcc gggcctccca ggacatctcc aactacctga actggtatca gcagaagccc   120
ggccaggccc ctcggctgct gatctactac acctcccggc tgcagtccgg catccctgcc   180
agattctccg gctctggctc tggcgccgac tacaccctga ccatctccag cctgcagccc   240
gaggacttcg ccgtgtactt ctgtcagcaa ggcaacaccc tgcccacac cttcggccag   300 ggcaccaagc tggaaatcaa gcgtacggtg gccgctccct ccgtgttcat cttcccaccc   360
tccgacgagc agctgaagtc cggcaccgcc tccgtcgtgt gcctgctgaa caacttctac   420
cctcgcgagg ccaaagtgca gtggaaagtg gacaacgccc tgcagagcgg caactcccag   480
gaatccgtca ccgagcagga ctccaaggac agcacctact ccctgtcctc caccctgacc   540
ctgtccaagg ccgactacga gaagcacaaa gtgtacgcct gcgaagtgac ccaccagggc   600
ctgtccagcc ccgtgaccaa gtccttcaac cggggcgagt gc                      642

<210> SEQ ID NO 36
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36
caagtccagc tgcaagaatc cggacccggc ctcgtcaagc cgtcccagac tctgtctctc    60
acttgcacgg tgtcaggcta cagcatcacc agcggttaca cctggcactg gatcaggcag   120

| catcctggaa agggctgga atggattggg tacattcact actcggtgta caccaactac | 180 |
| aacccatcgc tcaagtcgag agtcaccatt tcccgggaca cctccaagaa ccagttcagc | 240 |
| ctcaagctgt cctctgtgac cgccgctgat actgccgtgt actattgcgc acgccggact | 300 |
| acttccctgg agcgctactt cgacgtctgg ggcagggca ctttggtcac cgtcagctcc | 360 |

<210> SEQ ID NO 37
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37

| caagtccagc tgcaagaatc cggacccggc ctcgtcaagc cgtcccagac tctgtctctc | 60 |
| acttgcacgg tgtcaggcta cagcatcacc agcggttaca cctggcactg gatcaggcag | 120 |
| catcctggaa agggctgga atggattggg tacattcact actcggtgta caccaactac | 180 |
| aacccatcgc tcaagtcgag agtcaccatt tcccgggaca cctccaagaa ccagttcagc | 240 |
| ctcaagctgt cctctgtgac cgccgctgat actgccgtgt actattgcgc acgccggact | 300 |
| acttccctgg agcgctactt cgacgtctgg ggcagggca ctttggtcac cgtcagctcc | 360 |
| gccagcacta agggccccag cgtgtttccg ctggccccct cctccaaaag cacctccggc | 420 |
| ggaactgccg cgctcggatg tctcgtgaag gactatttcc ccgagcctgt gacagtgtca | 480 |
| tggaactcgg gagcactgac cagcggagtg catactttc ccgcggtcct gcagtcctcc | 540 |
| ggattgtaca gcctgtcatc ggtcgtgacc gtgccgtcct catcgctggg cacccagacc | 600 |
| tacatctgca acgtgaacca caaacctagc aacaccaaag tggataagcg ggtggaacct | 660 |
| aagtcctgcg acaagactca cacttgtccg ccatgcccag cgcctgaact cctgggtggt | 720 |
| ccttcggtgt tcctgttccc gccaaagccg aaggacaccc tgatgatctc ccggacgcct | 780 |
| gaagtgacct gtgtggtggt ggctgtgtca catgaggacc ctgaagtcaa gttcaattgg | 840 |
| tacgtggacg gcgtggaggt gcacaacgcc aagaccaagc ctagagagga acagtacaac | 900 |
| tccacctacc gcgtcgtgtc ggtgctgacc gtgttgcacc aagactggct gaatggaaag | 960 |
| gagtataagt gcaaagtgtc caacaaggcc ctggccgcac caattgagaa aaccatctcc | 1020 |
| aaggccaagg gacagccgcg cgaacccca gtgtacaccc ttcccccgtc ccgggaggaa | 1080 |
| atgaccaaga atcaagtctc cctgacttgc cttgtgaagg gtttctaccc ctccgacatc | 1140 |
| gccgtggagt gggagtcaaa cgggcagccg gaaaacaact acaagaccac acctccggtg | 1200 |
| ctggattccg acggctcctt cttcttgtac tcgaagctga ccgtggataa gagcaggtgg | 1260 |
| cagcagggaa acgtgttctc ctgctccgtg atgcacgaag ctctgcacaa ccactacact | 1320 |
| cagaagtcgc tctcgctgag ccccgggaag | 1350 |

<210> SEQ ID NO 38
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 38

| caagtccagc tgcaagaatc cggacccggc ctcgtcaagc cgtcccagac tctgtctctc | 60 |

-continued

```
acttgcacgg tgtcaggcta cagcatcacc agcggttaca cctggcactg gatcaggcag      120
catcctggaa aggggctgga atggattggg tacattcact actcggtgta caccaactac      180
aacccatcgc tcaagtcgag agtcaccatt tcccgggaca cctccaagaa ccagttcagc      240
ctcaagctgt cctctgtgac cgccgctgat actgccgtgt actattgcgc acgccggact      300
acttccctgg agcgctactt cgacgtctgg ggccagggca cttttggtcac cgtcagctcc     360
```

<210> SEQ ID NO 39
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 39

```
caagtccagc tgcaagaatc cggacccggc ctcgtcaagc cgtcccagac tctgtctctc       60
acttgcacgg tgtcaggcta cagcatcacc agcggttaca cctggcactg gatcaggcag      120
catcctggaa aggggctgga atggattggg tacattcact actcggtgta caccaactac      180
aacccatcgc tcaagtcgag agtcaccatt tcccgggaca cctccaagaa ccagttcagc      240
ctcaagctgt cctctgtgac cgccgctgat actgccgtgt actattgcgc acgccggact      300
acttccctgg agcgctactt cgacgtctgg ggccagggca cttttggtcac cgtcagctcc     360 gccagcacta agggcccag cgtgtttccg ctggccccct cctccaaaag cacctccggc       420
ggaactgccg cgctcggatg tctcgtgaag gactatttcc ccgagcctgt gacagtgtca      480
tggaactcgg gagcactgac cagcggagtg catactttc ccgcggtcct gcagtcctcc       540
ggattgtaca gcctgtcatc ggtcgtgacc gtgccgtcct catcgctggg cacccagacc      600
tacatctgca acgtgaacca caaacctagc aacaccaaag tggataagcg ggtggaacct      660
aagtcctgcg acaagactca cacttgtccg ccatgcccag cgcctgaact cctgggtggt      720
ccttcggtgt tcctgttccc gccaaagccg aaggacaccc tgatgatctc ccggacgcct      780
gaagtgacct gtgtggtggt ggctgtgtca catgaggacc ctgaagtcaa gttcaattgg      840 tacgtgacg gcgtggaggt gcacaacgcc aagaccaagc ctagagagga acagtacaac       900
tccacctacc gcgtcgtgtc ggtgctgacc gtgttgcacc aagactggct gaatggaaag      960
gagtataagt gcaaagtgtc caacaaggcc ctggccgcac aattgagaa aaccatctcc      1020 aaggccaagg gacagccgcg cgaaccccaa gtgtacaccc ttcccccgtc ccgggaggaa      1080
atgaccaaga atcaagtctc cctgacttgc cttgtgaagg gtttctaccc ctccgacatc     1140
gccgtggagt gggagtcaaa cgggcagccg gaaaacaact acaagaccac acctccggtg     1200
ctggattccg acggctcctt cttcttgtac tcgaagctga ccgtggataa gagcaggtgg     1260
cagcagggaa acgtgttctc ctgctccgtg atgcacgaag ctctgcacaa ccactacact     1320
cagaagtcgc tctcgctgag ccccgggaag                                       1350
```

<210> SEQ ID NO 40
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

-continued

<400> SEQUENCE: 40

```
gaaatcgtga tgactcagtc ccccgccact ctctccctgt ccctggcga acgggccacc    60
ctgtcgtgcc gggcgtcgca ggacatctca aactatctga actggtacca gcagaagcct   120
ggacaggcac ccaggctcct gatctactac acctcgcgcc tgcaatccgg aatcccagcc   180
cgcttctccg gttccggctc cggcgctgat acaccctca ccattagcag cctgcagccg    240
gaggacttcg ccgtgtactt ctgtcaacaa ggaaacaccc tcccgtacac atttgggcag   300
ggaaccaagc tggagattaa g                                             321
```

<210> SEQ ID NO 41
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 41

```
gaaatcgtga tgactcagtc ccccgccact ctctccctgt ccctggcga acgggccacc    60
ctgtcgtgcc gggcgtcgca ggacatctca aactatctga actggtacca gcagaagcct   120
ggacaggcac ccaggctcct gatctactac acctcgcgcc tgcaatccgg aatcccagcc   180
cgcttctccg gttccggctc cggcgctgat acaccctca ccattagcag cctgcagccg    240
gaggacttcg ccgtgtactt ctgtcaacaa ggaaacaccc tcccgtacac atttgggcag   300
ggaaccaagc tggagattaa gcgtacggtg gccgcgccgt ccgtgttcat cttccctcct   360
tctgacgagc agctcaagag cggcaccgcg tcggtggtct gcctgctgaa caacttctac   420
ccacgggagg ccaaggtcca gtggaaagtg gataacgcat gcagtcggg aaactcacag    480
gagtcggtga ccgaacagga ctccaaagac tcaacctact ccctgtcctc cactcttacc   540
ctgtccaagg cggactacga aaagcacaag gtctacgcct gcgaagtgac ccatcagggt   600
ctgagcagcc ctgtgactaa gagctttaac cgcggcgaat gc                      642
```

<210> SEQ ID NO 42
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 42

```
Tyr Ile His Tyr Ser Val Tyr Thr Asn Tyr Asn Pro Ser Val Lys Gly
1               5                   10                  15
```

<210> SEQ ID NO 43
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

```
Glu Val Gln Leu Val Glu Ser Gly Gly Gly Leu Val Lys Pro Gly Gly
1               5                   10                  15

Ser Leu Arg Leu Ser Cys Ala Val Ser Gly Tyr Ser Ile Thr Ser Gly
```

```
                20                  25                  30
Tyr Thr Trp His Trp Val Arg Gln Ala Pro Gly Lys Gly Leu Glu Trp
            35                  40                  45

Leu Ser Tyr Ile His Tyr Ser Val Tyr Thr Asn Tyr Asn Pro Ser Val
        50                  55                  60

Lys Gly Arg Phe Thr Ile Ser Arg Asp Thr Ala Lys Asn Ser Phe Tyr
 65                  70                  75                  80

Leu Gln Met Asn Ser Leu Arg Ala Glu Asp Thr Ala Val Tyr Tyr Cys
                85                  90                  95

Ala Arg Arg Thr Thr Ser Leu Glu Arg Tyr Phe Asp Val Trp Gly Gln
            100                 105                 110

Gly Thr Leu Val Thr Val Ser Ser
            115                 120

<210> SEQ ID NO 44
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44
gaagtccaac tcgtcgaatc cggcggcgga ctggtcaagc cgggaggatc gctgagactg      60
tcgtgcgcag tgtcagggta cagcatcacc tccggttaca cctggcactg ggtcagacag     120
gcgccgggaa aaggcctgga atggctgtcc tacattcatt actccgtgta cactaactac     180
aacccctcag tgaaggggcg gttcaccatc tcccgggaca ctgccaagaa tagcttctat     240
ctgcaaatga actccctgcg ggccgaggat accgccgtgt actactgcgc gaggcgcacc     300
acgtccctgg agcgctactt tgacgtgtgg ggccagggta ccctcgtgac tgtgtcctcg     360

<210> SEQ ID NO 45
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Glu Val Gln Leu Val Glu Ser Gly Gly Gly Leu Val Lys Pro Gly Gly
 1               5                  10                  15

Ser Leu Arg Leu Ser Cys Ala Val Ser Gly Tyr Ser Ile Thr Ser Gly
            20                  25                  30

Tyr Thr Trp His Trp Val Arg Gln Ala Pro Gly Lys Gly Leu Glu Trp
        35                  40                  45

Leu Ser Tyr Ile His Tyr Ser Val Tyr Thr Asn Tyr Asn Pro Ser Val
    50                  55                  60

Lys Gly Arg Phe Thr Ile Ser Arg Asp Thr Ala Lys Asn Ser Phe Tyr
65                  70                  75                  80

Leu Gln Met Asn Ser Leu Arg Ala Glu Asp Thr Ala Val Tyr Tyr Cys
                85                  90                  95

Ala Arg Arg Thr Thr Ser Leu Glu Arg Tyr Phe Asp Val Trp Gly Gln
            100                 105                 110

Gly Thr Leu Val Thr Val Ser Ser Ala Ser Thr Lys Gly Pro Ser Val
        115                 120                 125
```

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ala Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Ala Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 46
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46
gaagtccaac tcgtcgaatc cggcggcgga ctggtcaagc cgggaggatc gctgagactg      60
tcgtgcgcag tgtcagggta cagcatcacc tccggttaca cctggcactg ggtcagacag     120

```
gcgccgggaa aaggcctgga atggctgtcc tacattcatt actccgtgta cactaactac      180
aacccctcag tgaagggcg gttcaccatc tcccgggaca ctgccaagaa tagcttctat       240
ctgcaaatga actccctgcg ggccgaggat accgccgtgt actactgcgc gaggcgcacc     300
acgtccctgg agcgctactt tgacgtgtgg ggccagggta ccctcgtgac tgtgtcctcg    360
gctagcacca agggcccctc cgtgttccct ctggccccctt ccagcaagtc tacctccggc    420
ggcacagctg ctctgggctg cctggtcaag gactacttcc ctgagcctgt gacagtgtcc     480
tggaactctg gcgccctgac ctctggcgtg cacaccttcc ctgccgtgct gcagtcctcc    540
ggcctgtact ccctgtcctc cgtggtcaca gtgccttcaa gcagcctggg cacccagacc    600
tatatctgca acgtgaacca caagccttcc aacaccaagg tggacaagcg ggtggagcct    660
aagtcctgcg acaagaccca cacctgtcct ccctgccctg ctcctgaact gctgggcggc     720
ccttctgtgt tcctgttccc tccaaagccc aaggacaccc tgatgatctc ccggacccct    780
gaagtgacct gcgtggtggt ggccgtgtcc acgaggatc ctgaagtgaa gttcaattgg     840
tacgtggacg gcgtggaggt gcacaacgcc aagaccaagc ctcgggagga acagtacaac   900
tccacctacc gggtggtgtc cgtgctgacc gtgctgcacc aggactggct gaacggcaaa    960
gagtacaagt gcaaagtctc caacaaggcc ctggccgccc ctatcgaaaa gacaatctcc   1020
aaggccaagg gccagcctag ggaacccag gtgtacaccc tgccacccag ccgggaggaa    1080
atgaccaaga accaggtgtc cctgacctgt ctggtcaagg gcttctaccc ttccgatatc   1140
gccgtggagt gggagtctaa cggccagcct gagaacaact acaagaccac ccctcctgtg    1200
ctggactccg acggctcctt cttcctgtac tccaaactga ccgtggacaa gtcccggtgg   1260
cagcagggca acgtgttctc ctgctccgtg atgcacgagg ccctgcacaa ccactacacc    1320
cagaagtccc tgtccctgtc tcccggcaag                                      1350
```

<210> SEQ ID NO 47
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Thr Gly
    50                  55                  60

Ser Gly Ser Gly Ala Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gln Gly Thr Lys Leu Glu Ile Lys
                100                 105
```

<210> SEQ ID NO 48
<211> LENGTH: 321

<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 48

```
gatattcaga tgactcagag cccctcctcg ctctccgcct ccgtggggga tcgcgtgaca    60
atcacctgtc aagcgtccca ggacatctca aactacctga ctggtatca gcagaagcca   120
gggaaggccc cgaagctgct gatctactac acttcgcggc tgcagtccgg cgtgccgtca   180
cggttcactg gctcgggctc cggagcagac tacaccttca ccattagcag cctgcagccc   240
gaggacatcg ctacctactt ttgccaacaa ggaaacaccc tgccttacac cttcggacag   300
ggtactaagc tggaaatcaa a                                              321
```

<210> SEQ ID NO 49
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Thr Gly
    50                  55                  60

Ser Gly Ser Gly Ala Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 50
<211> LENGTH: 642
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 50

```
gatattcaga tgactcagag cccctcctcg ctctccgcct ccgtggggga tcgcgtgaca    60
atcacctgtc aagcgtccca ggacatctca aactacctga ctggtatca gcagaagcca    120
gggaaggccc cgaagctgct gatctactac acttcgcggc tgcagtccgg cgtgccgtca    180
cggttcactg gctcgggctc cggagcagac tacaccttca ccattagcag cctgcagccc    240
gaggacatcg ctacctactt tgccaacaa ggaaacaccc tgccttacac cttcggacag    300
ggtactaagc tggaaatcaa acgtacggtg gccgctccca gcgtgttcat cttccccccc    360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac aggggcgagt gc                      642
```

<210> SEQ ID NO 51
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 51

```
gacatccaga tgacccagag cccgtcgtcc ctctccgctt ccgtgggaga tagagtgacc    60
atcacctgtc aagccagcca ggatatttca aactacctga attggtacca gcagaagccg    120
gggaaggctc ccaagttgct catctactac acatcgaggc tgcagtccgg cgtgcccagc    180
cggttctccg gtccggatc aggcgccgac tataccttca ccatttcctc cctgcaaccg    240
gaggacattg ccacttactt ctgccaacaa gggaacaccc tgccctacac tttcggacaa    300
ggaactaagc tggaaatcaa gcgtacggtg gccgcgccgt ccgtgttcat cttccctcct    360
tctgacgagc agctcaagag cggcaccgcg tcggtggtct gcctgctgaa caacttctac    420
ccacgggagg ccaaggtcca gtggaaagtg gataacgcat gcagtcggg aaactcacag    480
gagtcggtga ccgaacagga ctccaaagac tcaacctact ccctgtcctc cactcttacc    540
ctgtccaagg cggactacga aaagcacaag gtctacgcct gcgaagtgac ccatcagggt    600
ctgagcagcc ctgtgactaa gagctttaac cgcggcgaat gc                      642
```

<210> SEQ ID NO 52
<211> LENGTH: 1044
<212> TYPE: PRT
<213> ORGANISM: Homo sapiens

<400> SEQUENCE: 52

```
Met Lys Pro Gly Cys Ala Ala Gly Ser Pro Gly Asn Glu Trp Ile Phe
 1               5                   10                  15

Phe Ser Thr Asp Glu Ile Thr Thr Arg Tyr Arg Asn Thr Met Ser Asn
                20                  25                  30

Gly Gly Leu Gln Arg Ser Val Ile Leu Ser Ala Leu Ile Leu Leu Arg
```

```
                35                  40                  45
Ala Val Thr Gly Phe Ser Gly Asp Gly Arg Ala Ile Trp Ser Lys Asn
            50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
        355                 360                 365

Phe Phe Ala Phe Ser Phe Gly Pro Asn Asn Phe Lys Pro Leu Asn Thr
    370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
        435                 440                 445

Leu Asp Glu Ile Arg Val Phe Gly Tyr Thr Ala Trp Ser Leu Leu Asp
    450                 455                 460
```

```
Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
            500                 505                 510

Ser Thr Pro Asp Val Gln Gly Gln Phe Pro Cys Asp Phe Ser Trp Gly
        515                 520                 525

Val Thr Glu Ser Val Leu Lys Pro Glu Ser Val Ala Ser Ser Pro Gln
    530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
        595                 600                 605

Thr Gly Asn Leu Ser Ala Val Asn Arg Gln Ala Leu Arg Tyr Tyr Arg
    610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
        675                 680                 685

Ile Thr Ile Asn Glu Pro Asn Arg Leu Ser Asp Ile Tyr Asn Arg Ser
    690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
        755                 760                 765

Ile Ala Trp Phe Ala Glu Pro Leu Phe Lys Thr Gly Asp Tyr Pro Ala
    770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
        835                 840                 845

Phe Leu Gln Asp Ile Thr Arg Leu Ser Ser Pro Thr Arg Leu Ala Val
    850                 855                 860

Ile Pro Trp Gly Val Arg Lys Leu Leu Arg Trp Val Arg Arg Asn Tyr
865                 870                 875                 880
```

```
Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
            915                 920                 925

Tyr Ala Phe Lys Leu Ala Glu Glu Lys Ser Lys Pro Arg Phe Gly Phe
        930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Ser Arg Cys
                965                 970                 975

Ser Gln Thr Gln Glu Asn Thr Glu Cys Thr Val Cys Leu Phe Leu Val
                980                 985                 990

Gln Lys Lys Pro Leu Ile Phe Leu Gly Cys Cys Phe Phe Ser Thr Leu
            995                 1000                1005

Val Leu Leu Leu Ser Ile Ala Ile Phe Gln Arg Gln Lys Arg Arg
        1010                1015                1020

Lys Phe Trp Lys Ala Lys Asn Leu Gln His Ile Pro Leu Lys Lys
        1025                1030                1035

Gly Lys Arg Val Val Ser
        1040

<210> SEQ ID NO 53
<211> LENGTH: 181
<212> TYPE: PRT
<213> ORGANISM: Homo sapiens

<400> SEQUENCE: 53

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 54
```

<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54

```
gacatccaga tgacccagag cccctccagc ctgtccgcct ccgtgggcga cagagtgacc      60
atcacctgtc aggcctccca ggacatctcc aactacctga ctggtatca gcagaagccc     120
ggcaaggccc ctaagctgct gatctactac acctcccggc tgcagtccgg cgtgccctcc    180
agattctccg gctctggctc tggcgccgac tacaccttca ccatctccag cctgcagccc    240
gaggatatcg ctacctactt ctgtcagcaa ggcaacaccc tgccctacac cttcggccag    300
ggcaccaagc tggaaatcaa g                                               321
```

<210> SEQ ID NO 55
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

```
Gln Val Gln Leu Val Gln Ser Gly Ala Glu Val Lys Lys Pro Gly Ser
1               5                  10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Arg Ile His Pro Gly Ser Gly Asn Thr Tyr Tyr Asn Glu Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Leu Leu Leu Arg Ser Tyr Gly Met Asp Asp Trp Gly Gln Gly
            100                 105                 110

Thr Thr Val Thr Val Ser Ser
        115
```

<210> SEQ ID NO 56
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

```
Gln Val Gln Leu Val Gln Ser Gly Ala Glu Val Lys Lys Pro Gly Ser
1               5                  10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45
```

Gly Arg Ile His Pro Gly Ser Gly Asn Thr Tyr Tyr Asn Glu Lys Phe
 50                  55                  60

Gln Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ile Leu Leu Leu Arg Ser Tyr Gly Met Asp Asp Trp Gly Gln Gly
                100                 105                 110

Thr Thr Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 57

```
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57
```

| | | | | | | | | | | | | | | | |
|---|---|---|---|---|---|---|---|---|---|---|---|---|---|---|---|
| Asp | Val | Val | Met | Thr | Gln | Thr | Pro | Leu | Ser | Leu | Ser | Val | Thr | Pro | Gly |
| 1 | | | | 5 | | | | | 10 | | | | | 15 | |
| Gln | Pro | Ala | Ser | Ile | Ser | Cys | Lys | Ser | Ser | Gln | Ser | Ile | Val | His | Ser |
| | | | 20 | | | | | 25 | | | | | 30 | | |
| Ser | Gly | Asn | Thr | Tyr | Leu | Glu | Trp | Tyr | Leu | Gln | Lys | Pro | Gly | Gln | Ser |
| | | | 35 | | | | | 40 | | | | | 45 | | |
| Pro | Gln | Leu | Leu | Ile | Tyr | Lys | Val | Ser | Asn | Arg | Phe | Ser | Gly | Val | Pro |
| | 50 | | | | | 55 | | | | | 60 | | | | |
| Asp | Arg | Phe | Ser | Gly | Ser | Gly | Ser | Gly | Thr | Asp | Phe | Thr | Leu | Lys | Ile |
| 65 | | | | | 70 | | | | | 75 | | | | | 80 |
| Ser | Arg | Val | Glu | Ala | Glu | Asp | Val | Gly | Val | Tyr | Tyr | Cys | Phe | Gln | Gly |
| | | | | 85 | | | | | 90 | | | | | 95 | |
| Ser | His | Ile | Pro | Tyr | Thr | Phe | Gly | Gln | Gly | Thr | Lys | Leu | Glu | Ile | Lys |
| | | | 100 | | | | | 105 | | | | | 110 | | |

```
<210> SEQ ID NO 58
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58
```

| | | | | | | | | | | | | | | | |
|---|---|---|---|---|---|---|---|---|---|---|---|---|---|---|---|
| Asp | Val | Val | Met | Thr | Gln | Thr | Pro | Leu | Ser | Leu | Ser | Val | Thr | Pro | Gly |
| 1 | | | | 5 | | | | | 10 | | | | | 15 | |
| Gln | Pro | Ala | Ser | Ile | Ser | Cys | Lys | Ser | Ser | Gln | Ser | Ile | Val | His | Ser |
| | | | 20 | | | | | 25 | | | | | 30 | | |
| Ser | Gly | Asn | Thr | Tyr | Leu | Glu | Trp | Tyr | Leu | Gln | Lys | Pro | Gly | Gln | Ser |
| | | | 35 | | | | | 40 | | | | | 45 | | |
| Pro | Gln | Leu | Leu | Ile | Tyr | Lys | Val | Ser | Asn | Arg | Phe | Ser | Gly | Val | Pro |
| | 50 | | | | | 55 | | | | | 60 | | | | |
| Asp | Arg | Phe | Ser | Gly | Ser | Gly | Ser | Gly | Thr | Asp | Phe | Thr | Leu | Lys | Ile |
| 65 | | | | | 70 | | | | | 75 | | | | | 80 |
| Ser | Arg | Val | Glu | Ala | Glu | Asp | Val | Gly | Val | Tyr | Tyr | Cys | Phe | Gln | Gly |
| | | | | 85 | | | | | 90 | | | | | 95 | |
| Ser | His | Ile | Pro | Tyr | Thr | Phe | Gly | Gln | Gly | Thr | Lys | Leu | Glu | Ile | Lys |
| | | | 100 | | | | | 105 | | | | | 110 | | |
| Arg | Thr | Val | Ala | Ala | Pro | Ser | Val | Phe | Ile | Phe | Pro | Pro | Ser | Asp | Glu |
| | | | 115 | | | | | 120 | | | | | 125 | | |
| Gln | Leu | Lys | Ser | Gly | Thr | Ala | Ser | Val | Val | Cys | Leu | Leu | Asn | Asn | Phe |
| | 130 | | | | | 135 | | | | | 140 | | | | |
| Tyr | Pro | Arg | Glu | Ala | Lys | Val | Gln | Trp | Lys | Val | Asp | Asn | Ala | Leu | Gln |
| 145 | | | | | 150 | | | | | 155 | | | | | 160 |
| Ser | Gly | Asn | Ser | Gln | Glu | Ser | Val | Thr | Glu | Gln | Asp | Ser | Lys | Asp | Ser |
| | | | | 165 | | | | | 170 | | | | | 175 | |
| Thr | Tyr | Ser | Leu | Ser | Ser | Thr | Leu | Thr | Leu | Ser | Lys | Ala | Asp | Tyr | Glu |
| | | | 180 | | | | | 185 | | | | | 190 | | |

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 59
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Glu Val Gln Leu Val Glu Ser Gly Gly Gly Leu Val Lys Pro Gly Gly
1               5                   10                  15

Ser Leu Arg Leu Ser Cys Ala Val Ser Gly Tyr Ser Ile Thr Ser Gly
            20                  25                  30

Tyr Thr Trp His Trp Val Arg Gln Ala Pro Gly Lys Gly Leu Glu Trp
        35                  40                  45

Leu Ser Tyr Ile His Tyr Ser Val Tyr Thr Asn Tyr Asn Pro Ser Val
    50                  55                  60

Lys Gly Arg Phe Thr Ile Ser Arg Asp Thr Ala Lys Asn Ser Phe Tyr
65                  70                  75                  80

Leu Gln Met Asn Ser Leu Arg Ala Glu Asp Thr Ala Val Tyr Tyr Cys
                85                  90                  95

Ala Arg Arg Thr Thr Ser Leu Glu Arg Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu

```
            325                 330                 335
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 60
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Thr Gly
50                  55                  60

Ser Gly Ser Gly Ala Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 61
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

```
Gln Val Gln Leu Val Gln Ser Gly Ala Glu Val Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Arg Ile His Pro Gly Ser Gly Asn Thr Tyr Tyr Asn Glu Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Leu Leu Leu Arg Ser Tyr Gly Met Asp Asp Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Ala Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Ala Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 62
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Ile Val His Ser
            20                  25                  30

Ser Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 63
<211> LENGTH: 546
<212> TYPE: DNA
<213> ORGANISM: Homo sapiens
```

-continued

```
<400> SEQUENCE: 63 cacccatcc ctgactccag tcctctcctg caattcgggg gccaagtccg gcagcggtac      60
ctctacacag atgatgccca gcagacagaa gcccacctgg agatcaggga ggatgggacg    120 gtgggggcg ctgctgacca gagccccgaa agtctcctgc agctgaaagc cttgaagccg    180
ggagttattc aaatcttggg agtcaagaca tccaggttcc tgtgccagcg gccagatggg    240
gccctgtatg gatcgctcca ctttgaccct gaggcctgca gcttccggga gctgcttctt    300
gaggacggat acaatgttta ccagtccgaa gcccacggcc tcccgctgca cctgccaggg    360
aacaagtccc cacaccggga ccctgcaccc cgaggaccag ctcgcttcct gccactacca    420
ggcctgcccc ccgcactccc ggagccaccc ggaatcctgg ccccccagcc cccgatgtg     480 ggctcctcgg accctctgag catggtggga ccttcccagg gccgaagccc cagctacgct    540
tcctga                                                               546

<210> SEQ ID NO 64
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 64

His His His His His His
1               5
```

FGF21 MIMETIC ANTIBODIES AND USES THEREOF

This application is a division of U.S. application Ser. No. 15/890,302, filed Feb. 6, 2018, which claims the benefit of U.S. Provisional Application No. 62/456,609 filed on Feb. 8, 2017, which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jan. 22, 2018, is named PAT057578-US-NP_SL.TXT and is 80,531 bytes in size.

FIELD

The present disclosure relates to fibroblast growth factor 21 (FGF21) mimetic antibodies. Also disclosed are methods for treating FGF21-associated disorders, such as obesity, type 1 and type 2 diabetes mellitus, pancreatitis, dyslipidemia, nonalcoholic steatohepatitis (NASH), insulin resistance, hyperinsulinemia, glucose intolerance, hyperglycemia, metabolic syndrome, and other metabolic disorders, and in reducing the mortality and morbidity of critically ill patients.

BACKGROUND

The fibroblast growth factor (FGF) family is characterized by 22 genetically distinct, homologous ligands, which are grouped into seven subfamilies. According to the published literature, the FGF family now consists of at least twenty-three members, FGF-1 to FGF-23 (Reuss et al. (2003) Cell Tissue Res. 313:139-157).

Fibroblast growth factor 21 (FGF21) was isolated from mouse embryos and is closest to FGF19 and FGF23. This FGF subfamily regulates diverse physiological processes uncommon to classical FGFs, namely energy and bile acid homeostasis, glucose and lipid metabolism, and phosphate as well as vitamin D homeostasis. Moreover, unlike classical FGFs, this subfamily acts in an endocrine fashion (Moore, D. D. (2007) Science 316, 1436-8). FGF21 has been reported to be preferentially expressed in the liver (Nishimura et al. (2000) Biochimica et Biophysica Acta, 1492:203-206; patent publication WO01/36640; and patent publication WO01/18172) and described as a treatment for ischemic vascular disease, wound healing, and diseases associated with loss of pulmonary, bronchia or alveolar cell function and numerous other disorders.

FGF21 has been identified as a potent metabolic regulator. Systemic administration of FGF21 to rodents and rhesus monkeys with diet-induced or genetic obesity and diabetes exerts strong anti-hyperglycemic and triglyceride-lowering effects, and reduction of body weight (Coskun, T, et al. (2008) Endocrinology 149:6018-6027; Kharitonenkov, A. et al. (2005) Journal of Clinical Investigation 115:1627-1635; Kharitonenkov, A., et al. (2007) Endocrinology 148:774-781; Xu, J, et al. (2009) Diabetes 58:250-259). FGF21 is a 209 amino acid polypeptide containing a 28 amino acid leader sequence. Human FGF21 has about 79% amino acid identity to mouse FGF21 and about 80% amino acid identity to rat FGF21.

In mammals, FGFs mediate their action via a set of four FGF receptors FGFR1-4 that in turn are expressed in multiple spliced variants. Each FGF receptor contains an intracellular tyrosine kinase domain that is activated upon ligand binding, leading to downstream signaling pathways involving MAPKs (Erk1/2), RAF1, AKT1 and STATs. (Kharitonenkov, A. et al. (2008) BioDrugs 22:37-44). Several reports suggested that the "c"-reporter splice variants of FGFR1-3 exhibit specific affinity to β-klotho and could act as endogenous receptors for FGF21 (Kurosu et al., 2007 J. Biol. Chem. 282:26687-26695); Ogawa et al., 2007 Proc. Natl. Acad. Sci. USA 104:7432-7437; Kharitonenkov et al., 2008 J. Cell Physiol. 215, 1-7). In 3T3-L1 cells and white adipose tissue. FGFR1 is by far the most abundant receptor, and it is therefore most likely that FGF21's main functional receptors in this tissue are the β-klotho-FGFR1c complexes.

Although FGF21 activates FGF receptors and downstream signaling molecules, including FRS2a and extracellular signal-regulated kinase (ERK), direct interaction of FGFRs and FGF21 has not been detected. Furthermore, various non-adipocyte cells do not respond to FGF21, even though they express multiple FGFR isoforms. All of these data suggest that a cofactor must mediate FGF21 signaling through FGFRs. Studies have identified beta-klotho (β-klotho), which is highly expressed in liver, adipocytes and in pancreas, as a determinant of the cellular response to FGF21 (Kurosu, H. et al. (2007) J Biol Chem 282, 26687-95). The β-klotho-FGFR complex, but not FGFR alone, binds to FGF21 in vitro (Kharitonenkov, A., et al. (2008) J Cell Physiol 215, 1-7). FGF21 binds to β-klotho in complex with FGFR1c, 2c, or 3c; but not to β-klotho in complex with FGFR4 (Owen et al., 2015 Trends in Endocrinology 26: 22-29). A similar mechanism has been identified in the FGF23-klotho-FGFR system (Urakawa, I. et al. (2006) Nature 444, 770-4).

The bioactivity of FGF21 was first identified in a mouse 3T3-L1 adipocyte glucose uptake assay (Kharitonenkov, A. et al. (2005) J Clin Invest 115, 1627-35). Subsequently, FGF21 was shown to induce insulin-independent glucose uptake and GLUT1 expression. FGF21 has also been shown to ameliorate hyperglycemia in a range of diabetic rodent models. In addition, transgenic mice over-expressing FGF21 were found to be resistant to diet-induced metabolic abnormalities, including decreased body weight and fat mass, and enhancements in insulin sensitivity (Badman, M. K. et al. (2007) Cell Metab 5, 426-37). Administration of FGF21 to diabetic non-human primates (NHP) caused a decline in fasting plasma glucose, triglycerides, insulin and glucagon levels, and led to significant improvements in lipoprotein profiles including a nearly 80% increase in HDL cholesterol (Kharitonenkov, A. et al. (2007) Endocrinology 148, 774-81). Importantly, hypoglycemia was not observed at any point during this NHP study. Other studies identified FGF21 as an important endocrine hormone that helps to control adaptation to the fasting state. This provides a previously missing link, downstream of PPARα, by which the liver communicates with the rest of the body in regulating the biology of energy homeostasis. The combined observations that FGF21 regulates adipose (lipolysis), liver (fatty acid oxidation and ketogenesis), and brain (torpor) establish it as a major endocrine regulator of the response to fasting (Kharitonenkov, A. & Shanafelt, A. B. (2008) BioDrugs 22, 37-44).

The problem with using FGF21 directly as a biotherapeutic is that its half-life is very short. In mice, the half-life of human FGF21 is 0.5 to 1 hours, and in cynomolgus monkeys, the half-life is 2 to 3 hours. Furthermore, when wild type FGF21 is used in pharmaceutical formulations or preparations, its stability is adversely affected by preservatives e.g., m-cresol.

SUMMARY

The present disclosure relates to FGF21 mimetic antibodies, i.e., monoclonal antibodies that bind to beta-klotho (β-klotho) and activate the human Fibroblast Growth Factor 21 (hereinafter, sometimes referred to as "FGF21") receptor complex and FGF21-mediated signaling (e.g., FGF21-receptor-dependent signaling), antigen-binding fragments thereof, and pharmaceutical compositions and methods of treatment comprising the same.

In specific aspects, antigen-binding fragments (of the FGF21 mimetic, β-klotho-binding antibodies) of the disclosure can be molecules with FGF21-like activity and selectivity but with added therapeutically desirable characteristics such as protein stability, low immunogenicity, ease of production and a desirable in vivo half-life.

The monoclonal FGF21 mimetic antibodies of the present disclosure, antigen-binding fragments thereof, and pharmaceutical compositions comprising the same are useful for the treatment of FGF21-associated disorders, such as obesity, type 2 diabetes mellitus, type 1 diabetes mellitus, pancreatitis, dyslipidemia, nonalcoholic steatohepatitis (NASH), insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, kidney disease, diabetic complications, neuropathy, gastroparesis and other metabolic disorders, and in reducing the mortality and morbidity of critically ill patients.

In particular aspects, isolated FGF21 mimetic antibodies, or antigen-binding fragments, described herein bind β-klotho, with an equilibrium dissociation constant ($K_D$) of less than or equal to 500 pM or 400 pM, for example as determined by BIACORE™ binding assay, and may also activate the cynomolgus monkey FGFR1c_β-klotho receptor complex with an EC50 of less than or equal to 50 nM, for example as measured by extracellular signal-regulated kinase (ERK) phosphorylation (pERK or phospho-ERK) cell assays. In particular aspects, isolated FGF21 mimetic antibodies, or antigen-binding fragments, described herein bind β-klotho, with an equilibrium dissociation constant ($K_D$) of less than or equal to 300 pM or 400 pM, for example as determined by BIACORE™ binding assay, and may also activate the cynomolgus monkey FGFR1c_β-klotho receptor complex with an EC50 of less than or equal to 50 nM, for example as measured by pERK cell assays.

In particular aspects, isolated FGF21 mimetic antibodies, or antigen-binding fragments, described herein bind β-klotho, with an equilibrium dissociation constant ($K_D$) of less than or equal to 100 pM or 50 pM. For example, isolated antibodies or antigen-binding fragments described herein may bind to human β-klotho with a $K_D$ of less than or equal to 100 pM, less than or equal to 50 pM, less than or equal to 45 pM, less than or equal to 40 pM, less than or equal to 35 pM, less than or equal to 25 pM, or less than or equal to 15 pM. More specifically, the isolated antibodies or antigen-binding fragments described herein may also bind human β-klotho with a $K_D$ of less than or equal to 10 pM, as measured by BIACORE™ binding assay or solution equilibrium titration assay (SET); and may also activate the cynomolgus monkey FGFR1c_β-klotho receptor complex with an EC50 of less than or equal to 50 nM, for example as measured by pERK cell assays.

The present disclosure relates to an isolated antibody, or antigen-binding fragments thereof, that binds to human and cynomolgus monkey β-klotho. The present disclosure also relates to an isolated antibody, or antigen-binding fragments thereof, that binds β-klotho and activates the FGF21 receptor complex and FGF21-mediated signaling (e.g., FGF21-receptor-dependent signaling). In particular aspects, an isolated antibody or antigen-binding fragment thereof described herein does not activate human FGFR2c_β-klotho, FGFR3c_β-klotho, or FGFR4_β-klotho receptor complexes.

The present disclosure also relates to an isolated antibody, or antigen-binding fragments thereof, that binds β-klotho and further competes for binding with an antibody as described in Table 1, for example, antibody NOV005 or NOV006. The present disclosure also further relates to an isolated antibody, or antigen-binding fragments thereof, that binds the same epitope as an antibody as described in Table 1, for example, antibody NOV005 or NOV006.

As described here, "competition" between antibodies and/or antigen-binding fragments thereof signifies that both antibodies (or binding fragments thereof) bind to the same β-klotho epitope (e.g., as determined by a competitive binding assay, by any of the methods well known to those of skill in the art). An antibody or antigen-binding fragment thereof also "competes" with a β-klotho antibody or antigen-binding fragment of the present disclosure (e.g., NOV005 or NOV006) if said competing antibody or antigen-binding fragment thereof binds the same β-klotho epitope, or an overlapping β-klotho epitope, as an antibody or antigen-binding fragment of the present disclosure. As used herein, a competing antibody or antigen-binding fragment thereof can also include one which (i) sterically blocks an antibody or antigen-binding fragment of the present disclosure from binding its target (e.g., if said competing antibody binds to a nearby, non-overlapping β-klotho and/or β-klotho epitope and physically prevents an antibody or antigen-binding fragment of the present disclosure from binding its target); and/or (ii) binds to a different, non-overlapping β-klotho epitope and induces a conformational change to the β-klotho protein such that said protein can no longer be bound by a β-klotho antibody or antigen-binding fragment of the present disclosure in a way that would occur absent said conformational change.

The binding affinity of isolated antibodies and antigen-binding fragments described herein can be determined by solution equilibrium titration (SET). Methods for SET are known in the art and are described in further detail below. Alternatively, binding affinity of the isolated antibodies, or fragments, described herein can be determined by Biacore assay. Methods for Biacore kinetic assays are know in the art and are described in further detail below.

The isolated FGF21 mimetic antibodies, or antigen-binding fragments thereof, may be used to increase the activation of the FGF21 receptor complex, and thereby, the FGF21 signaling pathway. In a particular aspect, isolated FGF21 mimetic antibodies, or antigen-binding fragments thereof, may be used to increase the activation of the FGF21 receptor complex, and thereby, the FGF21 signaling pathway, by at least about 15%, 20%, 25%, 30%, 35%, 40%, 45%, 50%, 55%, 60%, 65%, 70%, 75%, 80%, 85%, 90%, or 95%.

The isolated FGF21 mimetic antibodies, or antigen-binding fragments thereof, as described herein can be monoclonal antibodies, human or humanized antibodies, chimeric antibodies, single chain antibodies, Fab fragments, Fv fragments, F(ab')2 fragments, or scFv fragments, and/or IgG isotypes (e.g., IgG1, IgG2, or IgG4).

The isolated FGF21 mimetic antibodies, or antigen-binding fragments thereof, as described herein can also include a framework in which an amino acid has been substituted into the antibody framework from the respective human VH or VL germline sequences.

Another aspect of the present disclosure includes an isolated antibody or antigen-binding fragments thereof having the full heavy and light chain sequences of Fabs described in Table 1, for example, antibody NOV005 or NOV006. More specifically, the isolated antibody or antigen-binding fragments thereof can have the heavy and light chain sequences of Fab NOV005 or NOV006.

A further aspect of the present disclosure includes an isolated antibody or antigen-binding fragments thereof comprising the heavy and light chain variable domain sequences of Fabs described in Table 1, for example NOV005 or NOV006. More specifically, the isolated antibody or antigen-binding fragment thereof comprises the heavy and light chain variable domain sequence of Fab NOV005 or NOV006.

The present disclosure also relates to compositions (e.g., pharmaceutical compositions) comprising an isolated antibody, or antigen-binding fragments thereof, described herein (e.g., NOV005 or NOV006), as well as, antibody compositions in combination with a pharmaceutically acceptable carrier. Specifically, the present disclosure further includes pharmaceutical compositions comprising an antibody or antigen-binding fragments thereof of Table 1, such as, for example antibody NOV005 or NOV006. The present disclosure also relates to pharmaceutical compositions comprising a combination of two or more of the isolated antibodies or antigen-binding fragments thereof of Table 1, for example, antibody NOV005 or NOV006.

The present disclosure also relates to an isolated nucleic acid molecule comprising a nucleic acid sequence encoding the heavy chain variable region comprising the amino acid sequence of SEQ ID NO: 15. In particular aspects, the nucleic acid molecule comprises a sequence that has at least 90% sequence identity to a sequence selected from the group consisting of SEQ ID NOs: 16, 36, or 38. In a further aspect of the present disclosure, a nucleic acid molecule provided herein comprises the nucleic acid sequence of SEQ ID NO: 16, 36, or 38.

The present disclosure also relates to an isolated nucleic acid molecule comprising a nucleic acid sequence encoding a light chain variable region having an amino acid sequence of SEQ ID NO: 26 or 32. In particular aspects, the nucleic acid molecule comprises a sequence that has at least 90% sequence identity to a nucleic acid sequence of SEQ ID NO: 27, 54, 33, or 40. In a further aspect of the present disclosure a nucleic acid molecule provided herein comprises the nucleic acid sequence of SEQ ID NO: 27, 54, 33, or 40.

The present disclosure also relates to a vector that includes one or more of the nucleic acid molecules described herein. In specific aspects, a first vector encodes a heavy chain variable region or heavy chain of an antibody provided herein, such as NOV005 or NOV006, a second vector encodes a light chain variable region or heavy chain of an antibody provided herein, such as NOV005 or NOV006. The first vector and second vector are transduced into a host cell for coexpression to form antibodies comprising such heavy chains and such light chains.

The present disclosure also relates to an isolated host cell that includes a recombinant DNA sequence encoding a heavy chain of the antibody described above, and a second recombinant DNA sequence encoding a light chain of the antibody described above, wherein said DNA sequences are operably linked to a promoter and are capable of being expressed in the host cell. It is contemplated that the antibody can be a human monoclonal antibody. It is also contemplated that the host cell is a non-human mammalian cell, for example a CHO cell or HEK293 cell.

The present disclosure also relates to activating a Fibroblast Growth Factor 21 (FGF21) receptor, and, thereby, FGF21-mediated signaling (e.g., FGF21-receptor-dependent signaling), wherein the method includes the step of contacting a cell with an effective amount of a composition comprising the isolated antibody or antigen-binding fragments thereof described herein.

In one particular aspect, it is contemplated that the cell is a human cell. It is further contemplated that the cell is in a subject. In one embodiment, it is contemplated that the cell is an adipocyte. In other embodiments, the cell may be one or more of hepatocytes, pancreas cells, endothelial cells, muscle, or renal cells. In specific aspects, it is still further contemplated that the subject is human.

The present disclosure also relates to a method of treating, managing, improving, or preventing a FGF21-associated disorder in a subject, wherein the method includes the step of administering to the subject an effective amount of a composition comprising the antibody or antigen-binding fragments thereof described herein (e.g., NOV005 or NOV006). In one aspect, the FGF21-associated disorder is obesity. In one aspect, the FGF21-associated disorder is type 2 diabetes. It is contemplated that the subject is human.

Any of the foregoing isolated antibodies or antigen-binding fragments thereof may be a monoclonal antibody or antigen-binding fragments thereof.

Non-limiting embodiments of the disclosure are described in the following aspects:

1. An isolated antibody or antigen-binding fragment thereof that binds to an epitope of β-klotho, wherein the antibody or antigen-binding fragment thereof comprises:
a heavy chain CDR1 (HCDR1) comprising the amino acid sequence of SEQ ID NO: 6, 9, 10 or 12;
a heavy chain CDR2 (HCDR2) comprising the amino acid sequence of SEQ ID NO: 7, 11 or 13;
a heavy chain CDR3 (HCDR3) comprising the amino acid sequence of SEQ ID NO: 8 or 14;
a light chain CDR1 (LCDR1) comprising the amino acid sequence of SEQ ID NO: 19, 31, 22, or 25;
a light chain CDR2 (LCDR2) comprising the amino acid sequence of SEQ ID NO: 20 or 23; and
a light chain CDR3 (LCDR3) comprising the amino acid sequence of SEQ ID NO: 21 or 24.

2. The isolated antibody or antigen-binding fragment thereof according to aspect 1, wherein the antibody or antigen-binding fragment thereof comprises:
a heavy chain CDR1 (HCDR1) comprising the amino acid sequence of SEQ ID NO: 6, 9, 10 or 12;
a heavy chain CDR2 (HCDR2) comprising the amino acid sequence of SEQ ID NO: 7, 11 or 13;
a heavy chain CDR3 (HCDR3) comprising the amino acid sequence of SEQ ID NO: 8
or 14;
a light chain CDR1 (LCDR1) comprising the amino acid sequence of SEQ ID NO: 31, 22, or 25;
a light chain CDR2 (LCDR2) comprising the amino acid sequence of SEQ ID NO: 20 or 23; and
a light chain CDR3 (LCDR3) comprising the amino acid sequence of SEQ ID NO: 21 or 24.

3. The isolated antibody or antigen-binding fragment thereof according to aspect 1, wherein the antibody or antigen-binding fragment thereof comprises:

a heavy chain CDR1 (HCDR1) comprising the amino acid sequence of SEQ ID NO: 6, 9, 10 or 12;

a heavy chain CDR2 (HCDR2) comprising the amino acid sequence of SEQ ID NO: 7, 11 or 13;

a heavy chain CDR3 (HCDR3) comprising the amino acid sequence of SEQ ID NO: 8 or 14;

a light chain CDR1 (LCDR1) comprising the amino acid sequence of SEQ ID NO: 19, 31, 22, or 25;

a light chain CDR2 (LCDR2) comprising the amino acid sequence of SEQ ID NO: 20 or 23; and a light chain CDR3 (LCDR3) comprising the amino acid sequence of SEQ ID NO: 21 or 24.

4. The isolated antibody or antigen-binding fragment thereof according to aspect 1, wherein the antibody or antigen-binding fragment thereof comprises:

(i) a HCDR1 comprising the amino acid sequence of SEQ ID NO: 6, a HCDR2 comprising the amino acid sequence of SEQ ID NO: 7, a HCDR3 comprising the amino acid sequence of SEQ ID NO: 8, a LCDR1 comprising the amino acid sequence of SEQ ID NO: 31, a LCDR2 comprising the amino acid sequence of SEQ ID NO: 20, and a LCDR3 comprising the amino acid sequence of SEQ ID NO: 21;

(ii) a HCDR1 comprising the amino acid sequence of SEQ ID NO: 9, a HCDR2 comprising the amino acid sequence of SEQ ID NO: 7, a HCDR3 comprising the amino acid sequence of SEQ ID NO: 8, a LCDR1 comprising the amino acid sequence of SEQ ID NO: 31, a LCDR2 comprising the amino acid sequence of SEQ ID NO: 20, and a LCDR3 comprising the amino acid sequence of SEQ ID NO: 21;

(iii) a HCDR1 comprising the amino acid sequence of SEQ ID NO: 10, a HCDR2 comprising the amino acid sequence of SEQ ID NO: 11, a HCDR3 comprising the amino acid sequence of SEQ ID NO: 8, a LCDR1 comprising the amino acid sequence of SEQ ID NO: 22, a LCDR2 comprising the amino acid sequence of SEQ ID NO: 23, and a LCDR3 comprising the amino acid sequence of SEQ ID NO: 24; or (iv) a HCDR1 comprising the amino acid sequence of SEQ ID NO: 12, a HCDR2 comprising the amino acid sequence of SEQ ID NO: 13, a HCDR3 comprising the amino acid sequence of SEQ ID NO: 14, a LCDR1 comprising the amino acid sequence of SEQ ID NO: 25, a LCDR2 comprising the amino acid sequence of SEQ ID NO: 23, and a LCDR3 comprising the amino acid sequence of SEQ ID NO: 21.

5. The isolated antibody or antigen-binding fragment thereof according to aspect 1, wherein the antibody or antigen-binding fragment thereof comprises:

(i) a HCDR1 comprising the amino acid sequence of SEQ ID NO: 6, a HCDR2 comprising the amino acid sequence of SEQ ID NO: 7, a HCDR3 comprising the amino acid sequence of SEQ ID NO: 8, a LCDR1 comprising the amino acid sequence of SEQ ID NO: 19, a LCDR2 comprising the amino acid sequence of SEQ ID NO: 20, and a LCDR3 comprising the amino acid sequence of SEQ ID NO: 21;

(ii) a HCDR1 comprising the amino acid sequence of SEQ ID NO: 9, a HCDR2 comprising the amino acid sequence of SEQ ID NO: 7, a HCDR3 comprising the amino acid sequence of SEQ ID NO: 8, a LCDR1 comprising the amino acid sequence of SEQ ID NO: 19, a LCDR2 comprising the amino acid sequence of SEQ ID NO: 20, and a LCDR3 comprising the amino acid sequence of SEQ ID NO: 21;

(iii) a HCDR1 comprising the amino acid sequence of SEQ ID NO: 10, a HCDR2 comprising the amino acid sequence of SEQ ID NO: 11, a HCDR3 comprising the amino acid sequence of SEQ ID NO: 8, a LCDR1 comprising the amino acid sequence of SEQ ID NO: 22, a LCDR2 comprising the amino acid sequence of SEQ ID NO: 23, and a LCDR3 comprising the amino acid sequence of SEQ ID NO: 24; or (iv) a HCDR1 comprising the amino acid sequence of SEQ ID NO: 12, a HCDR2 comprising the amino acid sequence of SEQ ID NO: 13, a HCDR3 comprising the amino acid sequence of SEQ ID NO: 14, a LCDR1 comprising the amino acid sequence of SEQ ID NO: 25, a LCDR2 comprising the amino acid sequence of SEQ ID NO: 23, and a LCDR3 comprising the amino acid sequence of SEQ ID NO: 21.

6. The isolated antibody or antigen-binding fragment thereof according to aspect 1, wherein the antibody or antigen-binding fragment thereof comprises: a HCDR1 comprising the amino acid sequence of SEQ ID NO: 6, a HCDR2 comprising the amino acid sequence of SEQ ID NO: 7, a HCDR3 comprising the amino acid sequence of SEQ ID NO: 8, a LCDR1 comprising the amino acid sequence of SEQ ID NO: 19 or 31, a LCDR2 comprising the amino acid sequence of SEQ ID NO: 20, and a LCDR3 comprising the amino acid sequence of SEQ ID NO: 21.

7. The isolated antibody or antigen-binding fragment thereof according to aspect 1, wherein the antibody or antigen-binding fragment thereof comprises: a HCDR1 comprising the amino acid sequence of SEQ ID NO: 9, a HCDR2 comprising the amino acid sequence of SEQ ID NO: 7, a HCDR3 comprising the amino acid sequence of SEQ ID NO: 8, a LCDR1 comprising the amino acid sequence of SEQ ID NO: 19 or 31, a LCDR2 comprising the amino acid sequence of SEQ ID NO: 20, and a LCDR3 comprising the amino acid sequence of SEQ ID NO: 21.

8. The isolated antibody or antigen-binding fragment thereof according to aspect 1, wherein the antibody or antigen-binding fragment thereof comprises: a HCDR1 comprising the amino acid sequence of SEQ ID NO: 10, a HCDR2 comprising the amino acid sequence of SEQ ID NO: 11, a HCDR3 comprising the amino acid sequence of SEQ ID NO: 8, a LCDR1 comprising the amino acid sequence of SEQ ID NO: 22, a LCDR2 comprising the amino acid sequence of SEQ ID NO: 23, and a LCDR3 comprising the amino acid sequence of SEQ ID NO: 24.

9. The isolated antibody or antigen-binding fragment thereof according to aspect 1, wherein the antibody or antigen-binding fragment thereof comprises: a HCDR1 comprising the amino acid sequence of SEQ ID NO: 12, a HCDR2 comprising the amino acid sequence of SEQ ID NO: 13, a HCDR3 comprising the amino acid sequence of SEQ ID NO: 14, a LCDR1 comprising the amino acid sequence of SEQ ID NO: 25, a LCDR2 comprising the amino acid sequence of SEQ ID NO: 23, and a LCDR3 comprising the amino acid sequence of SEQ ID NO: 21.

10. The antibody or antigen-binding fragment thereof according to any one of aspects 1-9, wherein said antibody or fragment increases the activity of β-klotho and FGFR1c.

11. The antibody or antigen-binding fragment thereof according to any one of aspect 1-9, which binds to a human β-klotho protein with a $K_D$ of less than or equal to 450 pM, as measured by BIACORE™ binding assay.

12. The isolated antibody or antigen-binding fragment thereof according to any one of aspects 1-9, wherein said epitope comprises, or consists essentially of, (i) one or more amino acids of residues 246-265, 536-550, 834-857 and 959-986 of the β-klotho sequence (SEQ ID NO:52); or (ii) one, two, three, four, five, or more amino acid residues from each of the following stretches of residues 246-265, 536-550, 834-857 and 959-986 of the β-klotho sequence (SEQ ID NO:52).

13. The isolated antibody or antigen-binding fragment thereof according to any one of aspects 1-9, wherein said epitope comprises, or consists essentially of, (i) one or more of amino acids of residues 646-670, 696-700, and 646-689 of the β-klotho sequence (SEQ ID NO:52); or (ii) one, two, three, four, five, or more amino acid residues from each of the following stretches of residues 646-670, 696-700, and 646-689 of the β-klotho sequence (SEQ ID NO:52).

14. The isolated antibody or antigen-binding fragment thereof according to any one of aspects 1-13, which is capable of activating the cynomolgus monkey FGFR1c-β-klotho receptor complex with an EC50 of less than or equal to 50 nM, as measured by pERK cell assays.

15. The isolated antibody or antigen-binding fragment of any one of aspects 1-14, wherein said antibody or fragment does not contact residues 701 (Tyr) or 703 (Arg) of human β-klotho (SEQ ID NO: 52).

16. The isolated antibody or antigen-binding fragment of any one of aspects 1-15, wherein the antibody or fragment comprises a heavy chain variable region (VH) comprising the amino acid sequence of SEQ ID NO: 15 or an amino acid sequence with at least 90% or 95% identity thereof; and a light chain variable region (VL) comprising the amino acid sequence of SEQ ID NO: 26 or 32 or an amino acid sequence with at least 90% or 95% identity thereof.

17. The isolated antibody or antigen-binding fragment of any one of aspects 1-16, wherein the antibody or fragment comprises a VH comprising the amino acid sequence of SEQ ID NO: 15.

18. The isolated antibody or antigen-binding fragment of any one of aspects 1-17, wherein the antibody or fragment comprises a VL comprising the amino acid sequence of SEQ ID NO: 26 or 32.

19. The isolated antibody or antigen-binding fragment of aspect 17, wherein the antibody or fragment comprises a (i) a VH comprising the amino acid sequence of SEQ ID NO: 15 and a VL comprising the amino acid sequence of SEQ ID NO: 26 or (ii) a VH comprising the amino acid sequence of SEQ ID NO: 15 and a VL comprising the amino acid sequence of SEQ ID NO: 32.

20. The isolated antibody or antigen-binding fragment of any one of aspects 1-19, wherein the antibody comprises (i) a heavy chain comprising the amino acid sequence of SEQ ID NO: 17 and a light chain comprising the amino acid sequence of SEQ ID NO: 28, or (ii) a heavy chain comprising the amino acid sequence of SEQ ID NO: 17 and a light chain comprising the amino acid sequence of SEQ ID NO: 34.

21. An isolated antibody or antigen-binding fragment thereof, wherein the antibody or fragment binds to the same epitope as an isolated antibody or fragment according to any one of aspects 1-20, wherein the antibody or antigen-binding fragment does not comprise (i) Combined or Kabat CDRs of antibody NOV004 as set forth in Table 2; and/or (ii) a heavy chain variable domain comprising the amino acid sequence of SEQ ID NO: 43 or 55 and a light chain variable region comprising the amino acid sequence of SEQ ID NO: 47 or 57.

22. An isolated antibody or antigen-binding fragment thereof, wherein the antibody or fragment competes for binding to β-klotho with an isolated antibody or fragment according to any one of aspects 1-20, wherein the antibody or antigen-binding fragment does not comprise (i) Combined or Kabat CDRs of antibody NOV004 as set forth in Table 2; and/or (ii) a heavy chain variable domain comprising the amino acid sequence of SEQ ID NO: 43 or 55 and a light chain variable region comprising the amino acid sequence of SEQ ID NO: 47 or 57.

23. The isolated antibody or antigen-binding fragment of any one of aspects 1-20, wherein the antibody or fragment does not comprise (i) Combined or Kabat CDRs of antibody NOV004 as set forth in Table 2; and/or (ii) a heavy chain variable domain comprising the amino acid sequence of SEQ ID NO: 43 or 55 and a light chain variable region comprising the amino acid sequence of SEQ ID NO: 47 or 57.

24. A pharmaceutical composition comprising an antibody or antigen-binding fragment thereof of one of the above aspects and a pharmaceutically acceptable carrier.

25. A method of treating a metabolic disorder comprising administering to a subject afflicted with a metabolic disorder an effective amount of a pharmaceutical composition comprising an antibody or antigen-binding fragment according to any one of aspects 1-23.

26. The method of aspect 25, wherein the subject is afflicted with one or more of obesity, type 1 and type 2 diabetes mellitus, pancreatitis, dyslipidemia, nonalcoholic steatohepatitis (NASH), insulin resistance, hyperinsulinemia, glucose intolerance, hyperglycemia, hypertriglyceridemia, and metabolic syndrome.

27. The method of aspect 25, wherein the subject is afflicted with one or more of obesity, diabetes, and dyslipidemia.

28. A method of treating a cardiovascular disorder comprising administering to a subject afflicted with a cardiovascular disorder an effective amount of a pharmaceutical composition comprising an antibody or fragment according to any one of the previous aspects.

29. The method of aspect 28, wherein the subject is afflicted with one or more of atherosclerosis, peripheral arterial disease, stroke, heart failure, and coronary heart disease.

30. An antibody or antigen-binding fragment thereof according to any one of aspects 1-23, for use as a medicament.

31. A method of reducing body weight comprising administering to a subject in need thereof an effective amount of a pharmaceutical composition comprising an antibody or antigen-binding fragment according to any one of aspects 1-23.

32. A method of reducing appetite or food intake comprising administering to a subject in need thereof an effective amount of a pharmaceutical composition comprising an antibody or antigen-binding fragment according to any one of aspects 1-23.

33. A method of reducing plasma triglyceride (TG) concentrations or plasma total cholesterol (TC) concentrations in a subject, comprising administering to a subject in need thereof an effective amount of a pharmaceutical composition comprising an antibody or antigen-binding fragment according to any one of aspects 1-23.

34. The method of aspect 31, 32, or 33, wherein the subject is afflicted with a metabolic disorder.

35. The method of aspect 34, wherein the subject is afflicted with one or more of the following: obesity, type 1 and type 2 diabetes mellitus, pancreatitis, dyslipidemia, nonalcoholic steatohepatitis (NASH), insulin resistance, hyperinsulinemia, glucose intolerance, hyperglycemia, and metabolic syndrome.

36. A nucleic acid coding for one or more of the antibodies according to any one of the previous aspects, or for a VL and/or VH of any one of the antibodies.

37. A nucleic acid comprising a sequence with at least 90% identity to the sequences set forth in Table 1.

38. A nucleic acid comprising a sequence with at least 95% identity to the sequences set forth in Table 1.

39. A nucleic acid comprising a sequence set forth in Table 1.

40. A vector comprising the nucleic acid according to aspect 36, 37, 38, or 39.

41. A host cell comprising the vector of aspect 40.

42. A pharmaceutical composition comprising an antibody or antigen-binding fragment according to any one of aspects 1-23 for use in treating a metabolic disorder.

43. A method of making an antibody or antigen-binding fragment thereof which binds β-klotho, comprising the step of culturing the host cell of aspect 41 under conditions suitable for expression of the antibody or a fragment thereof.

44. The pharmaceutical composition of aspect 42, wherein the metabolic disorder is obesity, diabetes, hypertriglyceridemia, or dyslipidemia.

45. A pharmaceutical composition comprising an antibody or antigen-binding fragment according to any one of aspects 1-23 for use in treating a cardiovascular disorder.

46. A pharmaceutical composition comprising an antibody or antigen-binding fragment according to any one of aspects 1-23 for use in a method of reducing body weight, a method of reducing appetite or food intake, a method of reducing plasma triglyceride (TG) concentrations or plasma total cholesterol (TC) concentrations, in a subject.

47. Use of the antibody or antigen-binding fragment thereof according to any one of aspects 1-23 in the preparation of a medicament for treating a metabolic disorder, for treating a cardiovascular disorder, for reducing body weight, for reducing appetite or food intake, for reducing plasma TG concentrations or plasma TC concentrations, in a subject.

BRIEF DESCRIPTION OF THE DRAWINGS

FIG. 2A-FIG. 2C: Profiling of NOV004, NOV005, and NOV006 for pERK activation of human FGFR2c_β-klotho (FIG. 2A), FGFR3c_β-klotho (FIG. 2B), and FGFR4_β-klotho (FIG. 2C) HEK293 cells. FGF21 was used as a positive control for activation of FGFR2c_β-klotho or FGFR3c_β-klotho. FGF19 was used as a positive control for activation of FGFR4_β-klotho.

DETAILED DESCRIPTION

Figure 1:
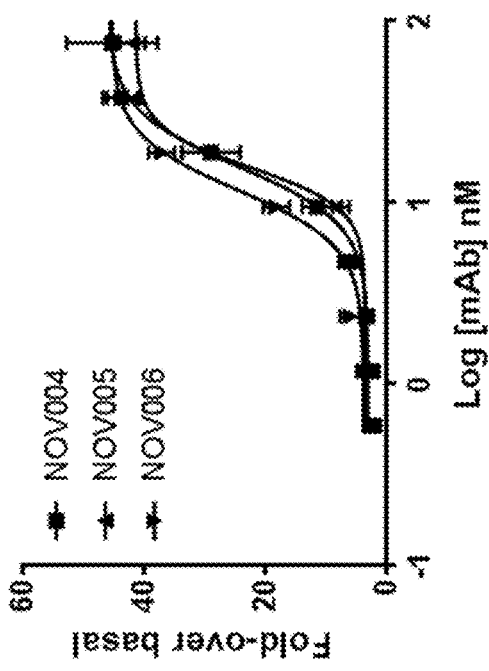
FIG. 1: pERK activation of human (FIG. 1A) and cynomolgus monkey (FIG. 1B) FGFR1c_β-klotho_HEK293 cells by NOV004, NOV005, and NOV006. The pERK activation data indicates that (i) NOV004 activated the human and cynomolgus monkey FGFR1c_β-klotho receptor complex with $EC_{50}$ of about 3 nM and 20 nM, respectively; (ii) NOV005 activated the human and cynomolgus monkey FGFR1c_β-klotho receptor complex with $EC_{50}$ of about 3 nM and 16 nM, respectively; and (iii) NOV006 activated the human and cynomolgus monkey FGFR1c_β-klotho receptor complex with $EC_{50}$ of about 4 nM and 18 nM, respectively.
Figure 1:
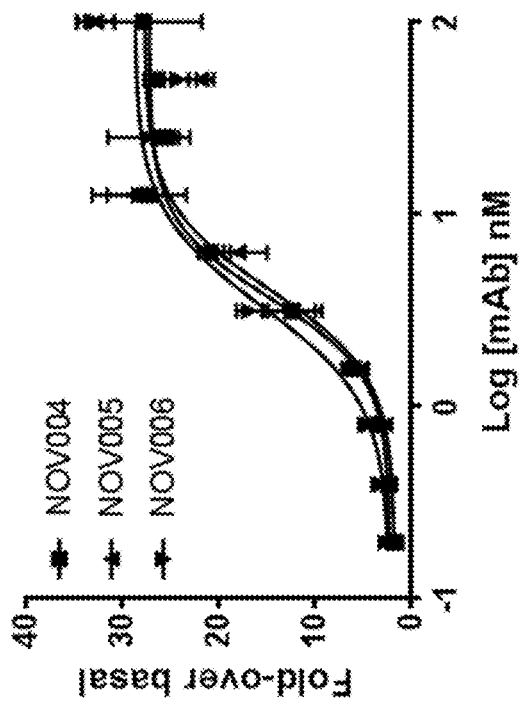

The present disclosure is based, in part, on the discovery of antibody molecules that specifically bind to β-klotho and lead to activation of FGF receptors, e.g., FGFR1c, and the activation of FGF21-mediated signaling (e.g., FGF21-receptor-dependent signaling). The present disclosure relates to both full IgG format antibodies as well as antigen-binding fragments thereof, such as Fab fragments (e.g., antibodies NOV005 or NOV006).

Accordingly, the present disclosure provides antibodies that specifically bind to β-klotho (e.g., human and cynomolgus monkey β-klotho), pharmaceutical compositions, production methods, and methods of use of such antibodies and compositions.

Terminology

Unless defined otherwise, all technical and scientific terms used herein have the same meaning as commonly understood by those of ordinary skill in the art to which this present disclosure pertains.

As used herein, the term "FGF21" refers to a member of the fibroblast growth factor (FGF) protein family. An exemplary amino acid sequence of FGF21 (GenBank Accession No. NP_061986.1) is set forth as SEQ ID NO:1, the corresponding polynucleotide sequence of which is set forth as SEQ ID NO:2 (NCBI reference sequence number NM_019113.2).

As used herein, the term "FGF21 receptor" refers to a receptor for FGF21 (Kharitonenkov, A, et al. (2008) Journal of Cellular Physiology 215:1-7; Kurosu, H, et al. (2007) JBC 282:26687-26695; Ogawa, Y, et al. (2007) PNAS 104:7432-7437).

The term "FGF21 polypeptide" refers to a naturally-occurring polypeptide expressed in humans. For purposes of this disclosure, the term "FGF21 polypeptide" can be used interchangeably to refer to any full-length FGF21 polypeptide, e.g., SEQ ID NO:1, which consists of 209 amino acid residues and which is encoded by the nucleotide sequence of SEQ ID NO:2; any mature form of the polypeptide, which consists of 181 amino acid residues, and in which the 28 amino acid residues at the amino-terminal end of the full-length FGF21 polypeptide (i.e., which constitute the signal peptide) have been removed, and variants thereof.

The term "antibody" as used herein means a whole antibody and any antigen-binding fragment (i.e., "antigen-binding portion") or single chain thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" or "antigen-binding fragment" of an antibody, as used herein, refers to one or more fragments of an intact antibody that retain the ability to specifically bind to a given antigen (e.g., β-klotho). Antigen-binding functions of an antibody can be performed by fragments of an intact antibody. Examples of binding fragments encompassed within the term antigen-binding portion or antigen-binding fragment of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain or a VL domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen-binding portions or fragments of an antibody. These antibody fragments are obtained using conventional techniques known to those of skill in the art, and the fragments are screened for utility in the same manner as are intact antibodies.

Antigen-binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen-binding portions of antibodies can be grafted into scaffolds based on polypeptides such as Fibronectin type III (Fn3) (see U.S. Pat. No. 6,703,199, which describes fibronectin polypeptide monobodies).

Antigen-binding fragments can be incorporated into single chain molecules comprising a pair of tandem Fv segments (VH—CH1-VH—CH1) which, together with complementary light chain polypeptides, form a pair of antigen-binding regions (Zapata et al. (1995) Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody or antigen-binding fragments thereof (e.g., a Fab fragment) generally refers to an antibody, or antigen-binding fragment, having a KD of $10^{-9}$M or less.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant.

The phrase "specifically (or selectively) binds" to an antibody (e.g., a β-klotho-binding antibody) refers to a binding reaction that is determinative of the presence of a cognate antigen (e.g., a human β-klotho or cynomolgus β-klotho) in a heterogeneous population of proteins and other biologics. The phrases "an antibody recognizing an antigen" and "an antibody specific for an antigen" are used interchangeably herein with the term "an antibody which binds specifically to an antigen".

The term "FGF21 mediated" or similar refers to the fact that the FGF21 receptor and/or the antibodies of the present disclosure mediate the cellular response and the FGF21 signaling pathway upon binding to β-klotho, thereby triggering a variety of physiological effects, including but not limited to a reduction in one or more of the following: plasma triglycerides, plasma insulin, plasma glucose, food intake, and body weight.

An "FGF21-associated disorder," "FGF21-associated condition," "disease or condition associated with FGF21," or similar terms as used herein, refer to any number of conditions or diseases for which the prevention, diagnosis, and/or treatment by activation of the FGF21 signaling pathway (e.g., by activation of FGF21 receptor signaling), is sought. These can include conditions, diseases, or disorders characterized by aberrant FGF21 signaling (e.g., aberrant activation of FGF21-mediated signaling and/or FGF21 receptor signaling). These conditions include but are not limited to metabolic, endocrine, and cardiovascular disorders, such as obesity, type 1 and type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, acute myocardial infarction, hypertension, cardiovascular disease, atherosclerosis, peripheral arterial disease, stroke, heart failure, coronary heart disease, kidney disease, diabetic complications, neuropathy, gastroparesis, disorders associated with severe inactivating mutations in the insulin receptor, and other metabolic disorders, and in reducing the mortality and morbidity of critically ill patients.

"Type 2 diabetes mellitus" is a condition characterized by excess glucose production in spite of the availability of insulin, and circulating glucose levels remain excessively high as a result of inadequate glucose clearance.

"Type 1 diabetes mellitus" is a condition characterized by high blood glucose levels caused by total lack of insulin. This occurs when the body's immune system attacks the insulin-producing beta cells in the pancreas and destroys them. The pancreas then produces little or no insulin.

"Pancreatitis" is inflammation of the pancreas.

"Dyslipidemia" is a disorder of lipoprotein metabolism, including lipoprotein overproduction or deficiency. Dyslipidemias may be manifested by elevation of the total cholesterol, low-density lipoprotein (LDL) cholesterol and triglyceride concentrations, and a decrease in high-density lipoprotein (HDL) cholesterol concentration in the blood.

"Nonalcoholic steatohepatitis (NASH)" is a liver disease, not associated with alcohol consumption, characterized by fatty change of hepatocytes, accompanied by intralobular inflammation and fibrosis.

"Glucose intolerance," or Impaired Glucose Tolerance (IGT) is a pre-diabetic state of dysglycemia that is associated with increased risk of cardiovascular pathology. The pre-diabetic condition prevents a subject from moving glucose into cells efficiently and utilizing it as an efficient fuel source, leading to elevated glucose levels in blood and some degree of insulin resistance.

"Hyperglycemia" is defined as an excess of sugar (glucose) in the blood.

"Hypoglycemia", also called low blood sugar, occurs when your blood glucose level drops too low to provide enough energy for your body's activities.

"Hyperinsulinemia" is defined as a higher-than-normal level of insulin in the blood.

"Insulin resistance" is defined as a state in which a normal amount of insulin produces a subnormal biologic response.

"Obesity," in terms of the human subject, can be defined as that body weight over 20 percent above the ideal body weight for a given population (R. H. Williams, Textbook of Endocrinology, 1974, p. 904-916). It can also be defined as a Body Mass Index (BMI, defined as a person's weight in kilograms divided by the square of his height in meters (kg/m2)) as greater than or equal to 30.

"Metabolic syndrome" can be defined as a cluster of at least three of the following signs: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and, blood pressure of 130/85 mmHg or higher.

"Hypertension" or high blood pressure that is a transitory or sustained elevation of systemic arterial blood pressure to a level likely to induce cardiovascular damage or other adverse consequences. Hypertension has been arbitrarily defined as a systolic blood pressure above 140 mmHg or a diastolic blood pressure above 90 mmHg.

"Cardiovascular diseases" are diseases related to the heart or blood vessels.

"Peripheral arterial disease" occurs when plaque builds up in the arteries that carry blood to the head, organs and limbs. Over time, plaque can harden and narrow the arteries which limits the flow of oxygen-rich blood to organs and other parts of the body.

"Atherosclerosis" is a vascular disease characterized by irregularly distributed lipid deposits in the intima of large and medium-sized arteries, causing narrowing of arterial lumens and proceeding eventually to fibrosis and calcification. Lesions are usually focal and progress slowly and intermittently. Limitation of blood flow accounts for most clinical manifestations, which vary with the distribution and severity of lesions.

"Stroke" is any acute clinical event, related to impairment of cerebral circulation, that lasts longer than 24 hours. A stroke involves irreversible brain damage, the type and severity of symptoms depending on the location and extent of brain tissue whose circulation has been compromised.

"Heart failure", also called congestive heart failure, is a condition in which the heart can no longer pump enough blood to the rest of the body.

"Coronary heart disease", also called coronary artery disease, is a narrowing of the small blood vessels that supply blood and oxygen to the heart.

"Kidney disease" or nephropathy is any disease of the kidney. Diabetic nephropathy is a major cause of morbidity and mortality in people with type 1 or type 2 diabetes mellitus.

"Diabetic complications" are problems, caused by high blood glucose levels, with other body functions such as kidneys, nerves (neuropathies), feet (foot ulcers and poor circulation) and eyes (e.g. retinopathies). Diabetes also increases the risk for heart disease and bone and joint disorders. Other long-term complications of diabetes include skin problems, digestive problems, sexual dysfunction and problems with teeth and gums.

"Neuroapathies" are any diseases involving the cranial nerves or the peripheral or autonomic nervous system.

"Gastroparesis" is weakness of gastric peristalsis, which results in delayed emptying of the bowels.

The critically ill patients encompassed by the present disclosure generally experience an unstable hypermetabolic state. This unstable metabolic state is due to changes in substrate metabolism, which may lead to relative deficiencies in some nutrients. Generally there is an increased oxidation of both fat and muscle.

Moreover, critically ill patients are preferably patients that experience systemic inflammatory response syndrome or respiratory distress. A reduction in morbidity means reducing the likelihood that a critically ill patient will develop additional illnesses, conditions, or symptoms or reducing the severity of additional illnesses, conditions, or symptoms. For example reducing morbidity may correspond to a decrease in the incidence of bacteremia or sepsis or complications associated with multiple organ failure.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the present disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the present disclosure may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to Xoma technology disclosed in U.S. Pat. No. 5,766,886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" refers to an antibody that is substantially free of other antibodies having different antigenic specificities (e.g., an isolated antibody that specifically binds β-klotho is substantially free of antibodies that specifically bind antigens other than β-klotho). An isolated antibody that specifically binds β-klotho may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e. $k_d/k_a$) and is expressed as a molar concentration (M). $K_D$ values for antibodies can be determined using methods well established in the art. Methods for determining the $K_D$ of an antibody include measuring surface plasmon resonance using a biosensor system such as a Biacore® system, or measuring affinity in solution by solution equilibrium titration (SET).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res.

19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates (e.g.: mammals and non-mammals) such as, non-human primates (e.g.: cynomolgus monkey), sheep, dog, cow, chickens, amphibians, and reptiles. Except when noted, the terms "patient" or "subject" are used herein interchangeably. As used herein, the terms "cyno" or "cynomolgus" refer to the cynomolgus monkey (*Macaca fascicularis*).

As used herein, the term "treating" or "treatment" of any disease or disorder (e.g., FGF21 associated disorder) refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

"Prevention" as it relates to indications described herein, including, e.g., FGF21 associated disorder, means any action that prevents or slows a worsening in e.g., FGF21 associated disease parameters, as described below, in a patient at risk for said worsening.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

In general, expression vectors of utility in recombinant DNA techniques are often in the form of plasmids. In the present specification, "plasmid" and "vector" may be used interchangeably as the plasmid is the most commonly used form of vector. However, the present disclosure is intended to include such other forms of expression vectors, such as viral vectors (e.g., replication defective retroviruses, adenoviruses and adeno-associated viruses), which serve equivalent functions.

"Modulation of FGF21 activity," as used herein, refers to an increase or decrease in FGF21 activity that can be a result of, for example, interaction of an agent with an FGF21 polynucleotide or polypeptide, activation of the FGF21 signaling pathway and/or activation of FGF21-mediated signaling (e.g., FGF21-receptor-dependent signaling), and the like. For example, modulation of a biological activity refers to an increase or a decrease in a biological activity. FGF21 activity can be assessed by means including, without limitation, assaying blood glucose, insulin, triglyceride, or cholesterol levels in a subject; by assessing polypeptide levels of beta-klotho and/or FGF receptors (e.g., FGFR-1c); or by assessing activation of FGF21-mediated signaling (e.g., of FGF21-receptor-dependent signaling).

Comparisons of FGF21 activity can also be accomplished by, e.g., measuring levels of an FGF21 downstream biomarker, and measuring increases in FGF21 signaling. Activity can also be assessed by measuring: cell signaling; kinase activity; glucose uptake into adipocytes; blood insulin, triglyceride, or cholesterol level fluctuations; liver lipid or liver triglyceride level changes; interactions between FGF21 and/or beta-klotho and an FGF21 receptor; or phosphorylation of an FGF21 receptor. In some embodiments phosphorylation of an FGF21 receptor can be tyrosine phosphorylation. In some embodiments modulation of FGF21 activity can cause modulation of an FGF21-related phenotype.

An "FGF21 downstream biomarker," as used herein, is a gene or gene product, or measurable indicia of a gene or gene product. In some embodiments, a gene or activity that is a downstream marker of FGF21 exhibits an altered level of expression, or in a vascular tissue. In some embodiments, an activity of the downstream marker is altered in the presence of an FGF21 modulator. In some embodiments, the downstream markers exhibit altered levels of expression when FGF21 is perturbed with an FGF21 modulator of the present disclosure. FGF21 downstream markers include, without limitation, glucose or 2-deoxy-glucose uptake, pERK and other phosphorylated or acetylated proteins or NAD levels.

As used herein, the term "up-regulates" refers to an increase, activation or stimulation of an activity or quantity. For example, in the context of the present disclosure, FGF21 modulators may increase the activity of beta-klotho and/or an FGF21 receptor. In one embodiment, FGFR-1c may be upregulated in response to an FGF21 modulator. Upregulation can also refer to an FGF21-related activity, such as e.g., the ability to lower blood glucose, insulin, triglyceride, or cholesterol levels; to reduce liver lipid or triglyceride levels; to reduce body weight; to improve glucose tolerance, energy expenditure, or insulin sensitivity; or to cause phosphorylation of an FGF21 receptor; or to increase an FGF21 downstream marker. The FGF21 receptor can be β-klotho and FGFR-1c. Up-regulation may be at least 25%, at least 50%, at least 75%, at least 100%, at least 150%, at least 200%, at least 250%, at least 400%, or at least 500% as compared to a control.

As used herein, the term "modulator" refers to a composition that modulates one or more physiological or biochemical events associated with an FGF21-associated disorder, such as type 1 or type 2 diabetes mellitus or a metabolic condition like obesity. Said events include but are not limited to the ability to lower blood glucose, insulin, triglyceride, or cholesterol levels; to reduce liver lipid or liver triglyceride levels; to reduce body weight; and to improve glucose tolerance, energy expenditure, or insulin sensitivity.

FGF21 Proteins

The present disclosure provides FGF21 mimetic antibodies (e.g., monoclonal antibodies that bind to beta-klotho (β-klotho)) that can induce FGF21-mediated signaling (e.g., FGF21-receptor-mediated signaling), as defined herein. In vivo, the mature form of FGF21 is the active form of the molecule. An exemplary human FGF21 wild-type sequence has NCBI reference sequence number NP_061986.1, and can be found in such issued patents as, e.g., U.S. Pat. No. 6,716,626 B1 for example, as set forth below (SEQ ID NO:1).

```
Met Asp Ser Asp Glu Thr Gly Phe Glu His Ser Gly Leu Trp Val Ser
 1               5                  10                 15

Val Leu Ala Gly Leu Leu Leu Gly Ala Cys Gln Ala His Pro Ile Pro
                20                  25                 30

Asp Ser Ser Pro Leu Leu Gln Phe Gly Gly Gln Val Arg Gln Arg Tyr
            35                  40                 45

Leu Tyr Thr Asp Asp Ala Gln Gln Thr Glu Ala His Leu Glu Ile Arg
        50                  55                 60

Glu Asp Gly Thr Val Gly Gly Ala Ala Asp Gln Ser Pro Glu Ser Leu
65                  70                  75                 80

Leu Gln Leu Lys Ala Leu Lys Pro Gly Val Ile Gln Ile Leu Gly Val
                85                  90                 95

Lys Thr Ser Arg Phe Leu Cys Gln Arg Pro Asp Gly Ala Leu Tyr Gly
                100                 105                110

Ser Leu His Phe Asp Pro Glu Ala Cys Ser Phe Arg Glu Leu Leu Leu
            115                 120                125

Glu Asp Gly Tyr Asn Val Tyr Gln Ser Glu Ala His Gly Leu Pro Leu
            130                 135                140

His Leu Pro Gly Asn Lys Ser Pro His Arg Asp Pro Ala Pro Arg Gly
145                 150                 155                160

Pro Ala Arg Phe Leu Pro Leu Pro Gly Leu Pro Pro Ala Leu Pro Glu
                165                 170                175
```

-continued

```
Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser
209
```

The corresponding mRNA sequence coding for the full-length FGF21 polypeptide (NCBI reference sequence number NM_019113.2) is shown below (SEQ ID NO:2)

```
  1  ctgtcagctg aggatccagc cgaaagagga gccaggcact
     caggccacct gagtctactc 61  acctggacaa ctggaatctg gcaccaattc taaaccactc
     agcttctccg agctcacacc 121  ccggagatca cctgaggacc cgagccattg atggactcgg
     acgagaccgg gttcgagcac 181  tcaggactgt gggtttctgt gctggctggt cttctgctgg
     gagcctgcca ggcacacccc 241  atccctgact ccagtcctct cctgcaattc ggggggccaag
     tccggcagcg gtacctctac 301  acagatgatg cccagcagac agaagcccac ctggagatca
     gggaggatgg gacggtgggg 361  ggcgctgctg accagagccc cgaaagtctc ctgcagctga
     aagccttgaa gccgggagtt 421  attcaaatct tgggagtcaa gacatccagg ttcctgtgcc
     agcggccaga tggggccctg 481  tatggatcgc tccactttga ccctgaggcc tgcagcttcc
     gggagctgct tcttgaggac 541  ggatacaatg tttaccagtc cgaagcccac ggcctcccgc
     tgcacctgcc agggaacaag
```

```
601  tccccacacc gggaccctgc accccgagga ccagctcgct
     tcctgccact accaggcctg 661  ccccccgcac tcccggagcc accggaatc ctggcccccc
     agccccccga tgtgggctcc 721  tcggaccctc tgagcatggt gggaccttcc cagggccgaa
     gccccagcta cgcttcctga 781  agccagaggc tgtttactat gacatctcct ctttatttat
     taggttattt atcttattta 841  ttttttattt tttcttactt gagataataa agagttccag
     aggagaaaaa aaaaaaaaaa 901  aaaaaaaa aaaaaaaaaa aaaaaaaaaa aaaaaaaaa
```

The mature FGF21 sequence lacks a leader sequence and may also include other modifications of a polypeptide such as proteolytic processing of the amino terminus (with or without a leader sequence) and/or the carboxyl terminus, cleavage of a smaller polypeptide from a larger precursor, N-linked and/or O-linked glycosylation, and other post-translational modifications understood by those with skill in the art. A representative example of a mature FGF21 sequence has the following sequence (SEQ ID NO:53, which represents amino acid positions 29-209 of full length FGF21 protein sequence (NCBI reference sequence number NP_061986.1)):

```
His Pro Ile Pro Asp Ser Ser Pro Leu Leu Gln Phe Gly Gly Gln Val
                5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
            50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160
```

```
Gly Ser Ser Asp Pro Leu Ser Met Val Gly Pro Ser Gln Gly Arg Ser
            165                 170                 175

Pro Ser Tyr Ala Ser
            180
```

The corresponding cDNA sequence coding for a mature FGF21 polypeptide (SEQ ID NO:53) is shown below (SEQ ID NO:63):

```
  1  caccccatcc ctgactccag tcctctcctg caattcgggg
     gccaagtccg gcagcggtac 61  ctctacacag atgatgccca gcagacagaa gcccacctgg
     agatcaggga ggatgggacg 121  gtgggggcg ctgctgacca gagccccgaa agtctcctgc
     agctgaaagc cttgaagccg 181  ggagttattc aaatcttggg agtcaagaca tccaggttcc
     tgtgccagcg gccagatggg 240  gccctgtatg gatcgctcca ctttgaccct gaggcctgca
     gcttccggga gctgcttctt 301  gaggacggat acaatgttta ccagtccgaa gcccacggcc
     tcccgctgca cctgccaggg 360  aacaagtccc cacaccggga ccctgcaccc cgaggaccag
     ctcgcttcct gccactacca 421  ggcctgcccc ccgcactccc ggagccaccc ggaatcctgg
     cccccagcc ccccgatgtg 481  ggctcctcgg accctctgag catggtggga ccttcccagg
     gccgaagccc cagctacgct 541  tcctga
```

FGF21 Mimetic Antibodies & Antigen-binding Fragments

The present disclosure provides antibodies that specifically bind to β-klotho (e.g., human β-klotho). In some embodiments, the present disclosure provides antibodies that specifically bind to human and cynomolgus monkey β-klotho. Antibodies of the present disclosure include, but are not limited to, the human monoclonal antibodies and Fabs, isolated as described in the Examples.

The β-klotho wild-type sequence has NCBI reference sequence number NP_783864.1, and can be found in such literature as Xu, et al. (2007) J Biol Chem. 282(40):29069-72 and Lin, et al. (2007) J Biol Chem. 282(37):27277-84. The full-length cDNA encoding human β-klotho has GenBank Accession number NM_175737). The protein sequence is as follows (SEQ ID NO:52).

```
  1  mkpgcaagsp gnewiffstd eittryrntm sngglqrsvi
     lsalillrav tgfsgdgrai 61  wsknpnftpv nesqlflydt fpknffwgig tgalqvegsw
     kkdgkgpsiw dhfihthlkn 121  vsstngssds yiflekdlsa ldfigvsfyq fsiswprlfp
     dgivtvanak glqyystlld 181  alvlrniepi vtlyhwdlpl alqekyggwk ndtiidifnd
     yatycfqmfg drvkywitih 241  npylvawhgy gtgmhapgek gnlaavytvg hnlikahskv
     whnynthfrp hqkgwlsitl 301  gshwiepnrs entmdifkcq qsmvsvlgwf anpihgdgdy
     pegmrkklfs vlpifseaek
```

```
361  hemrgtadff afsfgpnnfk pintmakmgq nvslnlreal
     nwikleynnp riliaengwf 421  tdsrvktedt taiymmknfl sqvlqairld eirvfgytaw
     slldgfewqd aytirrglfy 481  vdfnskqker kpkssahyyk qiirengfsl kestpdvqgq
     fpcdfswgvt esvlkpesva 541  sspqfsdphl yvwnatgnrl lhrvegvrlk trpaqctdfv
     nikkqlemla rmkvthyrfa 601  ldwasvlptg nlsavnrgal ryyrcvvseg lklgisamvt
     lyypthahlg lpepllhadg 661  wlnpstaeaf qayaglcfge lgdlvklwit inepnrlsdi
     ynrsgndtyg aahnllvaha 721  lawrlydrqf rpsqrgaysl slhadwaepa npyadshwra
     aerflqfeia wfaeplfktg 781  dypaamreyi askhrrglss salprlteae rrllkgtvdf
     calnhfttrf vmheqlagsr 841  ydsdrdiqfl qditrlsspt rlavipwgvr kllrwvrrny
     gdmdiyitas giddqaledd 901  rlrkyylgky lqevlkayli dkvrikgyya fklaeekskp
     rfgfftsdfk akssiqfynk 961  vissrgfpfe nsssrcsqtq entectvclf lvqkkplifl
     gccffstivl llsiaifqrq 1021 krrkfwkakn lqhiplkkgk rvvs
```

The present disclosure provides antibodies and antigen-binding fragments thereof that specifically bind a β-klotho protein (e.g., human and/or cynomolgus monkey β-klotho) and is capable of activating or increasing the activity of a β-klotho/FGFR1c receptor complex, wherein the antibody is described in Table 1, e.g., NOV005 or NOV006. In specific aspects, antibodies and antigen-binding fragments thereof provided herein, that specifically bind a β-klotho protein (e.g., human and/or cynomolgus monkey β-klotho) and is capable of activating or increasing the activity of a β-klotho/FGFR1c receptor complex, is not an antibody described in Table 2, for example, NOV001, NOV002, NOV003, or NOV004. Antibodies described in Table 2 have been described in PCT International Patent Application No. PCT/IB2016/054660 filed on Aug. 2, 2016, which is incorporated by reference herein in its entirety.

The present disclosure provides antibodies that specifically bind a β-klotho protein (e.g., human and/or cynomolgus monkey β-klotho), wherein the antibodies comprise a VH domain having an amino acid sequence of SEQ ID NO: 15. The present disclosure also provides antibodies that specifically bind to a β-klotho protein, wherein the antibodies comprise a VH CDR having an amino acid sequence of any one of the VH CDRs listed in Table 1, infra. In particular, the present disclosure provides antibodies that specifically bind to a β-klotho protein (e.g., human and cynomolgus monkey β-klotho), wherein the antibodies comprise (or alternatively, consist of) one, two, three, or more VH CDRs having an amino acid sequence of any of the VH CDRs listed in Table 1, infra.

The present disclosure provides antibodies that specifically bind to a β-klotho protein, said antibodies comprising a VL domain having an amino acid sequence of SEQ ID NOs: 26 or 32. The present disclosure also provides antibodies that specifically bind to a β-klotho protein (e.g., human and cynomolgus monkey β-klotho), said antibodies comprising a VL CDR having an amino acid sequence of any one of the VL CDRs listed in Table 1, infra. In particular, the present disclosure provides antibodies that specifically bind to a β-klotho protein (e.g., human and cynomolgus monkey β-klotho), said antibodies comprising (or alternatively, consisting of) one, two, three or more VL CDRs having an amino acid sequence of any of the VL CDRs listed in Table 1, infra.

Other antibodies of the present disclosure include amino acids that have been mutated, yet have at least 60, 70, 80, 85, 90 or 95 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

The present disclosure also provides nucleic acid molecules or polynucleotides comprising nucleic acid sequences that encode VH, VL, the full length heavy chain, and the full length light chain of the antibodies that specifically bind to a β-klotho protein (e.g., human and cynomolgus monkey β-klotho). Such nucleic acid sequences can be optimized for expression in mammalian cells (for example, Table 1 shows the optimized nucleic acid sequences for the heavy chain and light chain of antibodies of the present disclosure).

TABLE 1

Examples of FGF21 Mimetic Antibodies and Fabs

| | SEQ ID NO: | Amino acid sequence |
|---|---|---|
| NOV005 | | |
| HCDR1 (Combined) | 6 | GYSITSGYTWH |
| HCDR2 (Combined) | 7 | YIHYSVYTNYNPSLKS |
| HCDR3 (Combined) | 8 | RTTSLERYFDV |
| HCDR1 (Kabat) | 9 | SGYTWH |
| HCDR2 (Kabat) | 7 | YIHYSVYTNYNPSLKS |
| HCDR3 (Kabat) | 8 | RTTSLERYFDV |
| HCDR1 (Chothia) | 10 | GYSITSGY |
| HCDR2 (Chothia) | 11 | HYSVY |
| HCDR3 (Chothia) | 8 | RTTSLERYFDV |
| HCDR1 (IMGT) | 12 | GYSITSGYT |
| HCDR2 (IMGT) | 13 | IHYSVYT |
| HCDR3 (IMGT) | 14 | ARRTTSLERYFDV |
| VH | 15 | QVQLQESGPGLVKPSQTLSLTCTVSGYSITSGYTWHWIRQHPGKG<br>LEWIGYIHYSVYTNYNPSLKSRVTISRDTSKNQFSLKLSSVTAAD<br>TAVYYCARRTTSLERYFDVWGQGTLVTVSS |
| DNA VH (vector 1) | 16 | CAAGTGCAGCTGCAGGAATCTGGCCCTGGCCTGGTCAAGCCTAGC<br>CAGACCCTGTCCCTGACCTGCACCGTGTCCGGCTACTCCATCACC<br>TCCGGCTACACCTGGCACTGGATCCGGCAGCACCCCGGCAAGGGC<br>CTGGAATGGATCGGCTACATCCACTACTCCGTGTACACCAACTAC<br>AACCCCAGCCTGAAGTCCAGAGTGACCATCTCCCGGGACACCTCC<br>AAGAACCAGTTCTCCCTGAAGCTGTCCTCCGTGACCGCCGCTGAC<br>ACCGCCGTGTACTACTGCGCCAGACGGACCACCTCCCTGGAACGG<br>TACTTCGACGTGTGGGGCCAGGGCACCCTGGTCACCGTGTCCTCT |
| DNA VH (vector 2) | 36 | CAAGTCCAGCTGCAAGAATCCGGACCCGGCCTCGTCAAGCCGTCC<br>CAGACTCTGTCTCTCACTTGCACGGTGTCAGGCTACAGCATCACC<br>AGCGGTTACACCTGGCACTGGATCAGGCAGCATCCTGGAAAGGGG<br>CTGGAATGGATTGGGTACATTCACTACTCGGTGTACACCAACTAC<br>AACCCATCGCTCAAGTCGAGAGTCACCATTTCCCGGGACACCTCC<br>AAGAACCAGTTCAGCCTCAAGCTGTCCTCTGTGACCGCCGCTGAT<br>ACTGCCGTGTACTATTGCGCACGCCGGACTACTTCCCTGGAGCGC<br>TACTTCGACGTCTGGGGCCAGGGCACTTTGGTCACCGTCAGCTCC |
| Heavy Chain | 17 | QVQLQESGPGLVKPSQTLSLTCTVSGYSITSGYTWHWIRQHPGKG<br>LEWIGYIHYSVYTNYNPSLKSRVTISRDTSKNQFSLKLSSVTAAD<br>TAVYYCARRTTSLERYFDVWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDK<br>THTCPPCPAPELLGGPSVFLFPPKPKDTLMISRTPEVTCVVVAVS |

TABLE 1-continued

Examples of FGF21 Mimetic Antibodies and Fabs

| | SEQ ID NO: | Amino acid sequence |
|---|---|---|
| | | HEDPEVKFNWYVDGVEVHNAKTKPREEQYNSTYRVVSVLTVLHQD WLNGKEYKCKVSNKALAAPIEKTISKAKGQPREPQVYTLPPSREE MTKNQVSLTCLVKGFYPSDIAVEWESNGQPENNYKTTPPVLDSDG SFFLYSKLTVDKSRWQQGNVFSCSVMHEALHNHYTQKSLSLSPGK |
| DNA Heavy Chain (vector 1) | 18 | CAAGTGCAGCTGCAGGAATCTGGCCCTGGCCTGGTCAAGCCTAGC CAGACCCTGTCCCTGACCTGCACCGTGTCCGGCTACTCCATCACC TCCGGCTACACCTGGCACTGGATCCGGCAGCACCCCGGCAAGGGC CTGGAATGGATCGGCTACATCCACTACTCCGTGTACACCAACTAC AACCCCAGCCTGAAGTCCAGAGTGACCATCTCCCGGGACACCTCC AAGAACCAGTTCTCCCTGAAGCTGTCCTCCGTGACCGCCGCTGAC ACCGCCGTGTACTACTGCGCCAGACGGACCACCTCCCTGGAACGG TACTTCGACGTGTGGGGCCAGGGCACCCTGGTCACCGTGTCCTCT GCTTCCACCAAGGGGCCCTCCGTGTTCCCTCTGGCCCCTTCCAGC AAGTCCACCTCTGGCGGCACCGCCGCTCTGGGCTGCCTCGTGAAG GACTACTTCCCCGAGCCCGTGACCGTGTCCTGGAACTCTGGCGCC CTGACCTCCGGCGTGCACACCTTCCCTGCCGTGCTGCAGTCCTCC GGCCTGTACTCCCTGTCCAGCGTCGTGACCGTGCCCTCCAGCTCT CTGGGCACCCAGACCTACATCTGCAACGTGAACCACAAGCCCTCC AACACCAAAGTGGACAAGCGGGTGGAACCCAAGTCCTGCGACAAG ACCCACACCTGTCCTCCCTGCCCTGCCCCTGAGCTGCTGGGCGGA CCTTCCGTGTTCCTGTTCCCTCCAAAGCCCAAGGACACCCTGATG ATCTCCCGGACCCCTGAAGTGACCTGCGTGGTGGTGGCCGTGTCC CACGAGGATCCCGAAGTGAAGTTCAATTGGTACGTGGACGGCGTG GAAGTGCACAACGCCAAGACCAAGCCCAGAGAGGAACAGTACAAC TCCACCTACCGGGTGGTGTCCGTGCTGACCGTGCTGCACCAGGAC TGGCTGAACGGCAAAGAGTACAAGTGCAAAGTGTCCAACAAGGCC CTGGCCGCTCCCATCGAAAAGACCATCTCCAAGGCCAAGGGCCAG CCCCGCGAGCCCCAAGTGTACACACTGCCTCCCAGCCGGGAAGAG ATGACCAAGAATCAAGTGTCCCTGACATGTCTGGTCAAGGGCTTC TACCCTAGCGATATCGCCGTGGAATGGGAGTCCAACGGCCAGCCT GAGAACAACTACAAGACCACCCCTCCCGTGCTGGACTCCGACGGC TCATTCTTCCTGTACTCCAAGCTGACCGTGGACAAGTCCCGGTGG CAGCAGGGCAACGTGTTCTCCTGCTCCGTGATGCACGAGGCCCTG CACAACCACTACACCCAGAAGTCCCTGAGCCTGTCCCCTGGCAAG |
| DNA Heavy Chain (vector 2) | 37 | CAAGTCCAGCTGCAAGAATCCGGACCCGGCCTCGTCAAGCCGTCC CAGACTCTGTCTCTCACTTGCACGGTGTCAGGCTACAGCATCACC AGCGGTTACACCTGGCACTGGATCAGGCAGCATCCTGGAAAGGGG CTGGAATGGATTGGGTACATTCACTACTCGGTGTACACCAACTAC AACCCCATCCTCAAGTCGAGAGTCACCATTTCCGGGACACCTCC AAGAACCAGTTCAGCCTCAAGCTGTCCTCTGTGACCGCCGCTGAT ACTGCCGTGTACTATTGCGCACGCCGGACTACTTCCCTGGAGCGC TACTTCGACGTCTGGGGCCAGGGCACTTTGGTCACCGTCAGCTCC GCCAGCACTAAGGGCCCCAGCGTGTTTCCGCTGGCCCCCTCCTCC AAAAGCACCTCCGGCGGAACTGCCGCGCTCGGATGTCTCGTGAAG GACTATTTCCCCGAGCCTGTGACAGTGTCATGGAACTCGGGAGCA CTGACCAGCGGAGTGCATACTTTTCCCGCGGTCCTGCAGTCCTCC GGATTGTACAGCCTGTCATCGGTCGTGACCGTGCCGTCCTCATCG CTGGGCACCCAGACCTACATCTGCAACGTGAACCACAAACCTAGC AACACCAAAGTGGATAAGCGGGTGGAACCTAAGTCCTGCGACAAG ACTCACACTTGTCCGCCATGCCCAGCGCCTGAACTCCTGGGTGGT CCTTCGGTGTTCCTGTTCCCGCCAAAGCCGAAGGACACCCTGATG ATCTCCCGGACGCCTGAAGTGACCTGTGTGGTGGTGGCTGTGTCA CATGAGGACCCTGAAGTCAAGTTCAATTGGTACGTGGACGGCGTG GAGGTGCACAACGCCAAGACCAAGCCTAGAGAGGAACAGTACAAC TCCACCTACCGCGTCGTGTCGGTGCTGACCGTGTTGCACCAAGAC TGGCTGAATGGAAAGGAGTATAAGTGCAAAGTGTCCAACAAGGCC CTGGCCGCACCAATTGAGAAAACCATCTCCAAGGCCAAGGGACAG CCGCGCGAACCCCAAGTGTACACCCTTCCCCCGTCCCGGGAGGAA ATGACCAAGAATCAAGTCTCCCTGACTTGCCTTGTGAAGGGTTTC TACCCCTCCGACATCGCCGTGGAGTGGGAGTCAAACGGGCAGCCG GAAAACAACTACAAGACCACACCTCCGGTGCTGGATTCCGACGGC TCCTTCTTCTTGTACTCGAAGCTGACCGTGGATAAGAGCAGGTGG CAGCAGGGAAACGTGTTCTCCTGCTCCGTGATGCACGAAGCTCTG CACAACCACTACACTCAGAAGTCGCTCTCGCTGAGCCCCGGGAAG |
| LCDR1 (Combined) | 19 | QASQDISNYLN |
| LCDR2 (Combined) | 20 | YTSRLQS |
| LCDR3 (Combined) | 21 | QQGNTLPYT |
| LCDR1 (Kabat) | 19 | QASQDISNYLN |

TABLE 1-continued

Examples of FGF21 Mimetic Antibodies and Fabs

| | SEQ ID NO: | Amino acid sequence |
|---|---|---|
| LCDR2 (Kabat) | 20 | YTSRLQS |
| LCDR3 (Kabat) | 21 | QQGNTLPYT |
| LCDR1 (Chothia) | 22 | SQDISNY |
| LCDR2 (Chothia) | 23 | YTS |
| LCDR3 (Chothia) | 24 | GNTLPY |
| LCDR1 (IMGT) | 25 | QDISNY |
| LCDR2 (IMGT) | 23 | YTS |
| LCDR3 (IMGT) | 21 | QQGNTLPYT |
| VL | 26 | DIQMTQSPSSLSASVGDRVTITCQASQDISNYLNWYQQKPGKAPK LLIYYTSRLQSGVPSRFSGSGSGADYTFTISSLQPEDIATYFCQQ GNTLPYTFGQGTKLEIK |
| DNA VL (vector 1) | 54 | GACATCCAGATGACCCAGAGCCCCTCCAGCCTGTCCGCCTCCGTG GGCGACAGAGTGACCATCACCTGTCAGGCCTCCCAGGACATCTCC AACTACCTGAACTGGTATCAGCAGAAGCCCGGCAAGGCCCCTAAG CTGCTGATCTACTACACCTCCCGGCTGCAGTCCGGCGTGCCCTCC AGATTCTCCGGCTCTGGCTCTGGCGCCGACTACACCTTCACCATC TCCAGCCTGCAGCCCGAGGATATCGCTACCTACTTCTGTCAGCAA GGCAACACCCTGCCCTACACCTTCGGCCAGGGCACCAAGCTGGAA ATCAAG |
| DNA VL (vector 2) | 27 | GACATCCAGATGACCCAGAGCCCCGTCGTCCCTCTCCGCTTCCGTG GGAGATAGAGTGACCATCACCTGTCAAGCCAGCCAGGATATTCA AACTACCTGAATTGGTACCAGCAGAAGCCGGGGAAGGCTCCCAAG TTGCTCATCTACTACACATCGAGGCTGCAGTCCGGCGTGCCCAGC CGGTTCTCCGGGTCCGGATCAGGCGCCGACTATACCTTCACCATT TCCTCCCTGCAACCGGAGGACATTGCCACTTACTTCTGCCAACAA GGGAACACCCTGCCCTACACTTTCGGACAAGGAACTAAGCTGGAA ATCAAG |
| Light Chain | 28 | DIQMTQSPSSLSASVGDRVTITCQASQDISNYLNWYQQKPGKAPK LLIYYTSRLQSGVPSRFSGSGSGADYTFTISSLQPEDIATYFCQQ GNTLPYTFGQGTKLEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| DNA Light Chain (vector 1) | 29 | GACATCCAGATGACCCAGAGCCCCTCCAGCCTGTCCGCCTCCGTG GGCGACAGAGTGACCATCACCTGTCAGGCCTCCCAGGACATCTCC AACTACCTGAACTGGTATCAGCAGAAGCCCGGCAAGGCCCCTAAG CTGCTGATCTACTACACCTCCCGGCTGCAGTCCGGCGTGCCCTCC AGATTCTCCGGCTCTGGCTCTGGCGCCGACTACACCTTCACCATC TCCAGCCTGCAGCCCGAGGATATCGCTACCTACTTCTGTCAGCAA GGCAACACCCTGCCCTACACCTTCGGCCAGGGCACCAAGCTGGAA ATCAAGCGTACGGTGGCCGCTCCCTCCGTGTTCATCTTCCCACCC TCCGACGAGCAGCTGAAGTCCGGCACCGCCTCCGTCGTGTGCCTG CTGAACAACTTCTACCCTCGCGAGGCCAAAGTGCAGTGGAAAGTG GACAACGCCCTGCAGAGCGGCAACTCCCAGGAATCCGTCACCGAG CAGGACTCCAAGGACAGCACCTACTCCCTGTCCTCCACCCTGACC CTGTCCAAGGCCGACTACGAGAAGCACAAAGTGTACGCCTGCGAA GTGACCCACCAGGGCCTGTCCAGCCCCGTGACCAAGTCCTTCAAC CGGGGCGAGTGC |
| DNA Light Chain (vector 2) | 51 | GACATCCAGATGACCCAGAGCCCGTCGTCCCTCTCCGCTTCCGTG GGAGATAGAGTGACCATCACCTGTCAAGCCAGCCAGGATATTTCA AACTACCTGAATTGGTACCAGCAGAAGCCGGGGAAGGCTCCCAAG TTGCTCATCTACTACACATCGAGGCTGCAGTCCGGCGTGCCCAGC CGGTTCTCCGGGTCCGGATCAGGCGCCGACTATACCTTCACCATT TCCTCCCTGCAACCGGAGGACATTGCCACTTACTTCTGCCAACAA GGGAACACCCTGCCCTACACTTTCGGACAAGGAACTAAGCTGGAA ATCAAGCGTACGGTGGCCGCGCCGTCCGTGTTCATCTTCCCTCCT TCTGACGAGCAGCTCAAGAGCGGCACCGCGTCGGTGGTCTGCCTG CTGAACAACTTCTACCCACGGGAGGCCAAGGTCCAGTGGAAAGTG GATAACGCATTGCAGTCGGGAAACTCACAGGAGTCGGTGACCGAA CAGGACTCCAAAGACTCAACCTACTCCCTGTCCTCCACTCTTACC CTGTCCAAGGCGGACTACGAAAAGCACAAGGTCTACGCCTGCGAA GTGACCCATCAGGGTCTGAGCAGCCCTGTGACTAAGAGCTTTAAC CGCGGCGAATGC |

TABLE 1-continued

Examples of FGF21 Mimetic Antibodies and Fabs

| | SEQ ID NO: | Amino acid sequence |
|---|---|---|
| NOV006 | | |
| HCDR1 (Combined) | 6 | GYSITSGYTWH |
| HCDR2 (Combined) | 7 | YIHYSVYTNYNPSLKS |
| HCDR3 (Combined) | 8 | RTTSLERYFDV |
| HCDR1 (Kabat) | 9 | SGYTWH |
| HCDR2 (Kabat) | 7 | YIHYSVYTNYNPSLKS |
| HCDR3 (Kabat) | 8 | RTTSLERYFDV |
| HCDR1 (Chothia) | 10 | GYSITSGY |
| HCDR2 (Chothia) | 11 | HYSVY |
| HCDR3 (Chothia) | 8 | RTTSLERYFDV |
| HCDR1 (IMGT) | 12 | GYSITSGYT |
| HCDR2 (IMGT) | 13 | IHYSVYT |
| HCDR3 (IMGT) | 14 | ARRTTSLERYFDV |
| VH | 15 | QVQLQESGPGLVKPSQTLSLTCTVSGYSITSGYTWHWIRQHPGKG<br>LEWIGYIHYSVYTNYNPSLKSRVTISRDTSKNQFSLKLSSVTAAD<br>TAVYYCARRTTSLERYFDVWGQGTLVTVSS |
| DNA VH (vector 1) | 16 | CAAGTGCAGCTGCAGGAATCTGGCCCTGGCCTGGTCAAGCCTAGC<br>CAGACCCTGTCCCTGACCTGCACCGTGTCCGGCTACTCCATCACC<br>TCCGGCTACACCTGGCACTGGATCCGGCAGCACCCCGGCAAGGGC<br>CTGGAATGGATCGGCTACATCCACTACTCCGTGTACACCAACTAC<br>AACCCCAGCCTGAAGTCCAGAGTGACCATCTCCCGGGACACCTCC<br>AAGAACCAGTTCTCCCTGAAGCTGTCCTCCGTGACCGCCGCTGAC<br>ACCGCCGTGTACTACTGCGCCAGACGGACCACCTCCCTGGAACGG<br>TACTTCGACGTGTGGGGCCAGGGCACCCTGGTCACCGTGTCCTCT |
| DNA VH (vector 2) | 38 | CAAGTCCAGCTGCAAGAATCCGGACCCGGCCTCGTCAAGCCGTCC<br>CAGACTCTGTCTCTCACTTGCACGGTGTCAGGCTACAGCATCACC<br>AGCGGTTACACCTGGCACTGGATCAGGCAGCATCCTGGAAAGGGG<br>CTGGAATGGATTGGGTACATTCACTACTCGGTGTACACCAACTAC<br>AACCCCATCGCTCAAGTCGAGAGTCACCATTTCCCGGGACACCTCC<br>AAGAACCAGTTCAGCCTCAAGCTGTCCTCTGTGACCGCCGCTGAT<br>ACTGCCGTGTACTATTGCGCACGCCGGACTACTTCCCTGGAGCGC<br>TACTTCGACGTCTGGGGCCAGGGCACTTTGGTCACCGTCAGCTCC |
| Heavy Chain | 17 | QVQLQESGPGLVKPSQTLSLTCTVSGYSITSGYTWHWIRQHPGKG<br>LEWIGYIHYSVYTNYNPSLKSRVTISRDTSKNQFSLKLSSVTAAD<br>TAVYYCARRTTSLERYFDVWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDK<br>THTCPPCPAPELLGGPSVFLFPPKPKDTLMISRTPEVTCVVVAVS<br>HEDPEVKFNWYVDGVEVHNAKTKPREEQYNSTYRVVSVLTVLHQD<br>WLNGKEYKCKVSNKALAAPIEKTISKAKGQPREPQVYTLPPSREE<br>MTKNQVSLTCLVKGFYPSDIAVEWESNGQPENNYKTTPPVLDSDG<br>SFFLYSKLTVDKSRWQQGNVFSCSVMHEALHNHYTQKSLSLSPGK |
| DNA Heavy Chain (vector 1) | 30 | CAAGTGCAGCTGCAGGAATCTGGCCCTGGCCTGGTCAAGCCTAGC<br>CAGACCCTGTCCCTGACCTGCACCGTGTCCGGCTACTCCATCACC<br>TCCGGCTACACCTGGCACTGGATCCGGCAGCACCCCGGCAAGGGC<br>CTGGAATGGATCGGCTACATCCACTACTCCGTGTACACCAACTAC<br>AACCCCAGCCTGAAGTCCAGAGTGACCATCTCCCGGGACACCTCC<br>AAGAACCAGTTCTCCCTGAAGCTGTCCTCCGTGACCGCCGCTGAC<br>ACCGCCGTGTACTACTGCGCCAGACGGACCACCTCCCTGGAACGG<br>TACTTCGACGTGTGGGGCCAGGGCACCCTGGTCACCGTGTCCTCT<br>GCTTCCACCAAGGGGCCCTCCGTGTTCCCTCTGGCCCCTTCCAGC<br>AAGTCCACCTCTGGCGGCACCGCCGCTCTGGGCTGCCTCGTGAAG<br>GACTACTTCCCCGAGCCCGTGACCGTGTCCTGGAACTCTGGCGCC<br>CTGACCTCCGGCGTGCACACCTTCCCTGCCGTGCTGCAGTCCTCC<br>GGCCTGTACTCCCTGTCCAGCGTCGTGACCGTGCCCTCCAGCTCT<br>CTGGGCACCCAGACCTACATCTGCAACGTGAACCACAAGCCCTCC<br>AACACCAAAGTGGACAAGCGGGTGGAACCCAAGTCCTGCGACAAG |

TABLE 1-continued

Examples of FGF21 Mimetic Antibodies and Fabs

| | SEQ ID NO: | Amino acid sequence |
|---|---|---|
| | | ACCCACACCTGTCCTCCCTGCCCTGCCCCTGAGCTGCTGGGCGGA<br>CCTTCCGTGTTCCTGTTCCCTCCAAAGCCCAAGGACACCCTGATG<br>ATCTCCCGGACCCCTGAAGTGACCTGCGTGGTGGTGGCCGTGTCC<br>CACGAGGATCCCGAAGTGAAGTTCAATTGGTACGTGGACGGCGTG<br>GAAGTGCACAACGCCAAGACCAAGCCCAGAGAGGAACAGTACAAC<br>TCCACCTACCGGGTGGTGTCCGTGCTGACCGTGCTGCACCAGGAC<br>TGGCTGAACGGCAAAGAGTACAAGTGCAAAGTGTCCAACAAGGCC<br>CTGGCCGCTCCCATCGAAAAGACCATCTCCAAGGCCAAGGGCCAG<br>CCCCGCGAGCCCCAAGTGTACACACTGCCTCCCAGCCGGGAAGAG<br>ATGACCAAGAATCAAGTGTCCCTGACATGTCTGGTCAAGGGCTTC<br>TACCCTAGCGATATCGCCGTGGAATGGGAGTCCAACGGCCAGCCT<br>GAGAACAACTACAAGACCACCCCTCCCGTGCTGGACTCCGACGGC<br>TCATTCTTCCTGTACTCCAAGCTGACCGTGGACAAGTCCCGGTGG<br>CAGCAGGGCAACGTGTTCTCCTGCTCCGTGATGCACGAGGCCCTG<br>CACAACCACTACACCCAGAAGTCCCTGAGCCTGTCCCCTGGCAAG |
| DNA Heavy Chain (vector 2) | 39 | CAAGTCCAGCTGCAAGAATCCGGACCCGGCCTCGTCAAGCCGTCC<br>CAGACTCTGTCTCTCACTTGCACGGTGTCAGGCTACAGCATCACC<br>AGCGGTTACACCTGGCACTGGATCAGGCAGCATCCTGGAAAGGGG<br>CTGGAATGGATTGGGTACATTCACTACTCGGTGTACACCAACTAC<br>AACCCATCGCTCAAGTCGAGAGTCACCATTTCCCGGGACACCTCC<br>AAGAACCAGTTCAGCCTCAAGCTGTCCTCTGTGACCGCCGCTGAT<br>ACTGCCGTGTACTATTGCGCACGCCGGACTACTTCCCTGGAGCGC<br>TACTTCGACGTCTGGGGCCAGGGCACTTTGGTCACCGTCAGCTCC<br>GCCAGCACTAAGGGCCCCAGCGTGTTTCCGCTGGCCCCCTCCTCC<br>AAAAGCACCTCCGGCGGAACTGCCGCGCTCGGATGTCTCGTGAAG<br>GACTATTTCCCCGAGCCTGTGACAGTGTCATGGAACTCGGGAGCA<br>CTGACCAGCGGAGTGCATACTTTTCCCGCGGTCCTGCAGTCCTCC<br>GGATTGTACAGCCTGTCATCGGTCGTGACCGTGCCGTCCTCATCG<br>CTGGGCACCCAGACCTACATCTGCAACGTGAACCACAAACCTAGC<br>AACACCAAAGTGGATAAGCGGGTGGAACCTAAGTCCTGCGACAAG<br>ACTCACACTTGTCCGCCATGCCCAGCGCCTGAACTCCTGGGTGGT<br>CCTTCGGTGTTCCTGTTCCCGCCAAAGCCGAAGGACACCCTGATG<br>ATCTCCCGGACGCCTGAAGTGACCTGTGTGGTGGTGGCTGTGTCA<br>CATGAGGACCCTGAAGTCAAGTTCAATTGGTACGTGGACGGCGTG<br>GAGGTGCACAACGCCAAGACCAAGCCTAGAGAGGAACAGTACAAC<br>TCCACCTACCGCGTCGTGTCGGTGCTGACCGTGTTGCACCAAGAC<br>TGGCTGAATGGAAAGGAGTATAAGTGCAAAGTGTCCAACAAGGCC<br>CTGGCCGCACCAATTGAGAAAACCATCTCCAAGGCCAAGGGACAG<br>CCGCGCGAACCCCAAGTGTACACCCTTCCCCCGTCCCGGGAGGAA<br>ATGACCAAGAATCAAGTCTCCCTGACTTGCCTTGTGAAGGGTTTC<br>TACCCCTCCGACATCGCCGTGGAGTGGGAGTCAAACGGGCAGCCG<br>GAAAACAACTACAAGACCACACCTCCGGTGCTGGATTCCGACGGC<br>TCCTTCTTCTTGTACTCGAAGCTGACCGTGGATAAGAGCAGGTGG<br>CAGCAGGGAAACGTGTTCTCCTGCTCCGTGATGCACGAAGCTCTG<br>CACAACCACTACACTCAGAAGTCGCTCTCGCTGAGCCCCGGGAAG |
| LCDR1 (Combined) | 31 | RASQDISNYLN |
| LCDR2 (Combined) | 20 | YTSRLQS |
| LCDR3 (Combined) | 21 | QQGNTLPYT |
| LCDR1 (Kabat) | 31 | RASQDISNYLN |
| LCDR2 (Kabat) | 20 | YTSRLQS |
| LCDR3 (Kabat) | 21 | QQGNTLPYT |
| LCDR1 (Chothia) | 22 | SQDISNY |
| LCDR2 (Chothia) | 23 | YTS |
| LCDR3 (Chothia) | 24 | GNTLPY |
| LCDR1 (IMGT) | 25 | QDISNY |
| LCDR2 (IMGT) | 23 | YTS |
| LCDR3 (IMGT) | 21 | QQGNTLPYT |
| VL | 32 | EIVMTQSPATLSLSPGERATLSCRASQDISNYLNWYQQKPGQAPR<br>LLIYYTSRLQSGIPARFSGSGSGADYTLTISSLQPEDFAVYFCQQ<br>GNTLPYTFGQGTKLEIK |

TABLE 1-continued

Examples of FGF21 Mimetic Antibodies and Fabs

| | SEQ ID NO: | Amino acid sequence |
|---|---|---|
| DNA VL (vector 1) | 33 | GAGATCGTGATGACCCAGTCCCCTGCCACCCTGTCCCTGAGCCCT<br>GGCGAGAGAGCCACCCTGAGCTGCCGGGCCTCCCAGGACATCTCC<br>AACTACCTGAACTGGTATCAGCAGAAGCCCGGCCAGGCCCCTCGG<br>CTGCTGATCTACTACACCTCCCGGCTGCAGTCCGGCATCCCTGCC<br>AGATTCTCCGGCTCTGGCTCTGGCGCCGACTACACCCTGACCATC<br>TCCAGCCTGCAGCCCGAGGACTTCGCCGTGTACTTCTGTCAGCAA<br>GGCAACACCCTGCCCTACACCTTCGGCCAGGGCACCAAGCTGGAA<br>ATCAAG |
| DNA VL (vector 2) | 40 | GAAATCGTGATGACTCAGTCCCCCGCCACTCTCTCCCTGTCCCCT<br>GGCGAACGGGCCACCCTGTCGTGCCGGGCGTCGCAGGACATCTCA<br>AACTATCTGAACTGGTACCAGCAGAAGCCTGGACAGGCACCCAGG<br>CTCCTGATCTACTACACCTCGCGCCTGCAATCCGGAATCCCAGCC<br>CGCTTCTCCGGTTCCGGCTCCGGCGCTGATTACACCCTCACCATT<br>AGCAGCCTGCAGCCGGAGGACTTCGCCGTGTACTTCTGTCAACAA<br>GGAAACACCCTCCCGTACACATTTGGGCAGGGAACCAAGCTGGAG<br>ATTAAG |
| Light Chain | 34 | EIVMTQSPATLSLSPGERATLSCRASQDISNYLNWYQQKPGQAPR<br>LLIYYTSRLQSGIPARFSGSGSGADYTLTISSLQPEDFAVYFCQQ<br>GNTLPYTFGQGTKLEIKRTVAAPSVFIFPPSDEQLKSGTASVVCL<br>LNNFYPREAKVQWKVDNALQSGNSQESVTEQDSKDSTYSLSSTLT<br>LSKADYEKHKVYACEVTHQGLSSPVTKSFNRGEC |
| DNA Light Chain (vector 1) | 35 | GAGATCGTGATGACCCAGTCCCCTGCCACCCTGTCCCTGAGCCCT<br>GGCGAGAGAGCCACCCTGAGCTGCCGGGCCTCCCAGGACATCTCC<br>AACTACCTGAACTGGTATCAGCAGAAGCCCGGCCAGGCCCCTCGG<br>CTGCTGATCTACTACACCTCCCGGCTGCAGTCCGGCATCCCTGCC<br>AGATTCTCCGGCTCTGGCTCTGGCGCCGACTACACCCTGACCATC<br>TCCAGCCTGCAGCCCGAGGACTTCGCCGTGTACTTCTGTCAGCAA<br>GGCAACACCCTGCCCTACACCTTCGGCCAGGGCACCAAGCTGGAA<br>ATCAAGCGTACGGTGGCCGCTCCCTCCGTGTTCATCTTCCCACCC<br>TCCGACGAGCAGCTGAAGTCCGGCACCGCCTCCGTCGTGTGCCTG<br>CTGAACAACTTCTACCCTCGCGAGGCCAAAGTGCAGTGGAAAGTG<br>GACAACGCCCTGCAGAGCGGCAACTCCCAGGAATCCGTCACCGAG<br>CAGGACTCCAAGGACAGCACCTACTCCCTGTCCTCCACCCTGACC<br>CTGTCCAAGGCCGACTACGAGAAGCACAAAGTGTACGCCTGCGAA<br>GTGACCCACCAGGGCCTGTCCAGCCCCGTGACCAAGTCCTTCAAC<br>CGGGGCGAGTGC |
| DNA Light Chain (vector 2) | 41 | GAAATCGTGATGACTCAGTCCCCCGCCACTCTCTCCCTGTCCCCT<br>GGCGAACGGGCCACCCTGTCGTGCCGGGCGTCGCAGGACATCTCA<br>AACTATCTGAACTGGTACCAGCAGAAGCCTGGACAGGCACCCAGG<br>CTCCTGATCTACTACACCTCGCGCCTGCAATCCGGAATCCCAGCC<br>CGCTTCTCCGGTTCCGGCTCCGGCGCTGATTACACCCTCACCATT<br>AGCAGCCTGCAGCCGGAGGACTTCGCCGTGTACTTCTGTCAACAA<br>GGAAACACCCTCCCGTACACATTTGGGCAGGGAACCAAGCTGGAG<br>ATTAAGCGTACGGTGGCCGCGCCGTCCGTGTTCATCTTCCCTCCT<br>TCTGACGAGCAGCTCAAGAGCGGCACCGCGTCGGTGGTCTGCCTG<br>CTGAACAACTTCTACCCACGGGAGGCCAAGGTCCAGTGGAAAGTG<br>GATAACGCATTGCAGTCGGGAAACTCACAGGAGTCGGTGACCGAA<br>CAGGACTCCAAAGACTCAACCTACTCCCTGTCCTCCACTCTTACC<br>CTGTCCAAGGCGGACTACGAAAGCACAAGGTCTACGCCTGCGAA<br>GTGACCCATCAGGGTCTGAGCAGCCCTGTGACTAAGAGCTTTAAC<br>CGCGGCGAATGC |

TABLE 2

FGF21 mimetic antibodies

| | SEQ ID NO: | Amino Acid Sequence |
|---|---|---|
| NOV004 | | |
| HCDR1 (Combined) | 6 | GYSITSGYTWH |
| HCDR2 (Combined) | 42 | YIHYSVYTNYNPSVKG |
| HCDR3 (Combined) | 8 | RTTSLERYFDV |
| HCDR1 (Kabat) | 9 | SGYTWH |

TABLE 2-continued

FGF21 mimetic antibodies

| | SEQ ID NO: | Amino Acid Sequence |
|---|---|---|
| HCDR2 (Kabat) | 42 | YIHYSVYTNYNPSVKG |
| HCDR3 (Kabat) | 8 | RTTSLERYFDV |
| HCDR1 (Chothia) | 10 | GYSITSGY |
| HCDR2 (Chothia) | 11 | HYSVY |
| HCDR3 (Chothia) | 8 | RTTSLERYFDV |
| HCDR1 (IMGT) | 12 | GYSITSGYT |
| HCDR2 (IMGT) | 13 | IHYSVYT |
| HCDR3 (IMGT) | 14 | ARRTTSLERYFDV |
| VH | 43 | EVQLVESGGGLVKPGGSLRLSCAVSGYSITSGYTWHWVRQAPGKG<br>LEWLSYIHYSVYTNYNPSVKGRFTISRDTAKNSFYLQMNSLRAED<br>TAVYYCARRTTSLERYFDVWGQGTLVTVSS |
| DNA VH | 44 | GAAGTCCAACTCGTCGAATCCGGCGGCGGACTGGTCAAGCCGGGA<br>GGATCGCTGAGACTGTCGTGCGCAGTGTCAGGGTACAGCATCACC<br>TCCGGTTACACCTGGCACTGGGTCAGACAGGCGCCGGGAAAAGGC<br>CTGGAATGGCTGTCCTACATTCATTACTCCGTGTACACTAACTAC<br>AACCCCTCAGTGAAGGGGCGGTTCACCATCTCCCGGGACACTGCC<br>AAGAATAGCTTCTATCTGCAAATGAACTCCCTGCGGGCCGAGGAT<br>ACCGCCGTGTACTACTGCGCGAGGCGCACCACGTCCCTGGAGCGC<br>TACTTTGACGTGTGGGGCCAGGGTACCCTCGTGACTGTGTCCTCG |
| Heavy Chain | 45 | EVQLVESGGGLVKPGGSLRLSCAVSGYSITSGYTWHWVRQAPGKG<br>LEWLSYIHYSVYTNYNPSVKGRFTISRDTAKNSFYLQMNSLRAED<br>TAVYYCARRTTSLERYFDVWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDK<br>THTCPPCPAPELLGGPSVFLFPPKPKDTLMISRTPEVICVVVAVS<br>HEDPEVKFNWYVDGVEVHNAKTKPREEQYNSTYRVVSVLTVLHQD<br>WLNGKEYKCKVSNKALAAPIEKTISKAKGQPREPQVYTLPPSREE<br>MTKNQVSLTCLVKGFYPSDIAVEWESNGQPENNYKTTPPVLDSDG<br>SFFLYSKLTVDKSRWQQGNVFSCSVMHEALHNHYTQKSLSLSPGK |
| DNA Heavy Chain | 46 | GAAGTCCAACTCGTCGAATCCGGCGGCGGACTGGTCAAGCCGGGA<br>GGATCGCTGAGACTGTCGTGCGCAGTGTCAGGGTACAGCATCACC<br>TCCGGTTACACCTGGCACTGGGTCAGACAGGCGCCGGGAAAAGGC<br>CTGGAATGGCTGTCCTACATTCATTACTCCGTGTACACTAACTAC<br>AACCCCTCAGTGAAGGGGCGGTTCACCATCTCCCGGGACACTGCC<br>AAGAATAGCTTCTATCTGCAAATGAACTCCCTGCGGGCCGAGGAT<br>ACCGCCGTGTACTACTGCGCGAGGCGCACCACGTCCCTGGAGCGC<br>TACTTTGACGTGTGGGGCCAGGGTACCCTCGTGACTGTGTCCTCG<br>GCTAGCACCAAGGGCCCCTCCGTGTTCCCTCTGGCCCCTTCCAGC<br>AAGTCTACCTCCGGCGGCACAGCTGCTCTGGGCTGCCTGGTCAAG<br>GACTACTTCCCTGAGCCTGTGACAGTGTCCTGGAACTCTGGCGCC<br>CTGACCTCTGGCGTGCACACCTTCCCTGCCGTGCTGCAGTCCTCC<br>GGCCTGTACTCCCTGTCCTCCGTGGTCACAGTGCCTTCAAGCAGC<br>CTGGGCACCCAGACCTATATCTGCAACGTGAACCACAAGCCTTCC<br>AACACCAAGGTGGACAAGCGGGTGGAGCCTAAGTCCTGCGACAAG<br>ACCCACACCTGTCCTCCCTGCCCTGCTCCTGAACTGCTGGGCGGC<br>CCTTCTGTGTTCCTGTTCCCTCCAAAGCCCAAGGACACCCTGATG<br>ATCTCCCGGACCCCTGAAGTGACCTGCGTGGTGGTGGCCGTGTCC<br>CACGAGGATCCTGAAGTGAAGTTCAATTGGTACGTGGACGGCGTG<br>GAGGTGCACAACGCCAAGACCAAGCCTCGGGAGGAACAGTACAAC<br>TCCACCTACCGGGTGGTGTCCGTGCTGACCGTGCTGCACCAGGAC<br>TGGCTGAACGGCAAAGAGTACAAGTGCAAAGTCTCCAACAAGGCC<br>CTGGCCGCCCCTATCGAAAAGACAATCTCCAAGGCCAAGGGCCAG<br>CCTAGGGAACCCCAGGTGTACACCCTGCCACCCAGCCGGGAGGAA<br>ATGACCAAGAACCAGGTGTCCCTGACCTGTCTGGTCAAGGGCTTC<br>TACCCTTCCGATATCGCCGTGGAGTGGGAGTCTAACGGCCAGCCT<br>GAGAACAACTACAAGACCACCCCTCCTGTGCTGGACTCCGACGGC<br>TCCTTCTTCCTGTACTCCAAACTGACCGTGGACAAGTCCCGGTGG<br>CAGCAGGGCAACGTGTTCTCCTGCTCCGTGATGCACGAGGCCCTG<br>CACAACCACTACACCCAGAAGTCCCTGTCCCTGTCTCCCGGCAAG |
| LCDR1 (Combined) | 19 | QASQDISNYLN |
| LCDR2 (Combined) | 20 | YTSRLQS |

TABLE 2-continued

FGF21 mimetic antibodies

| | SEQ ID NO: | Amino Acid Sequence |
|---|---|---|
| LCDR3 (Combined) | 21 | QQGNTLPYT |
| LCDR1 (Kabat) | 19 | QASQDISNYLN |
| LCDR2 (Kabat) | 20 | YTSRLQS |
| LCDR3 (Kabat) | 21 | QQGNTLPYT |
| LCDR1 (Chothia) | 22 | SQDISNY |
| LCDR2 (Chothia) | 23 | YTS |
| LCDR3 (Chothia) | 24 | GNTLPY |
| LCDR1 (IMGT) | 25 | QDISNY |
| LCDR2 (IMGT) | 23 | YTS |
| LCDR3 (IMGT) | 21 | QQGNTLPYT |
| VL | 47 | DIQMTQSPSSLSASVGDRVTITCQASQDISNYLNWYQQKPGKAPK LLIYYTSRLQSGVPSRFTGSGSGADYTFTISSLQPEDIATYFCQQ GNTLPYTFGQGTKLEIK |
| DNA VL | 48 | GATATTCAGATGACTCAGAGCCCCTCCTCGCTCTCCGCCTCCGTG GGGGATCGCGTGACAATCACCTGTCAAGCGTCCCAGGACATCTCA AACTACCTGAACTGGTATCAGCAGAAGCCAGGGAAGGCCCCGAAG CTGCTGATCTACTACACTTCGCGGCTGCAGTCCGGCGTGCCGTCA CGGTTCACTGGCTCGGGCTCCGGAGCAGACTACACCTTCACCATT AGCAGCCTGCAGCCCGAGGACATCGCTACCTACTTTTGCCAACAA GGAAACACCCTGCCTTACACCTTCGGACAGGGTACTAAGCTGGAA ATCAAA |
| Light Chain | 49 | DIQMTQSPSSLSASVGDRVTITCQASQDISNYLNWYQQKPGKAPK LLIYYTSRLQSGVPSRFTGSGSGADYTFTISSLQPEDIATYFCQQ GNTLPYTFGQGTKLEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| DNA Light Chain | 50 | GATATTCAGATGACTCAGAGCCCCTCCTCGCTCTCCGCCTCCGTG GGGGATCGCGTGACAATCACCTGTCAAGCGTCCCAGGACATCTCA AACTACCTGAACTGGTATCAGCAGAAGCCAGGGAAGGCCCCGAAG CTGCTGATCTACTACACTTCGCGGCTGCAGTCCGGCGTGCCGTCA CGGTTCACTGGCTCGGGCTCCGGAGCAGACTACACCTTCACCATT AGCAGCCTGCAGCCCGAGGACATCGCTACCTACTTTTGCCAACAA GGAAACACCCTGCCTTACACCTTCGGACAGGGTACTAAGCTGGAA ATCAAACGTACGGTGGCCGCTCCCAGCGTGTTCATCTTCCCCCCC AGCGACGAGCAGCTGAAGAGCGGCACCGCCAGCGTGGTGTGCCTG CTGAACAACTTCTACCCCCGGGAGGCCAAGGTGCAGTGGAAGGTG GACAACGCCCTGCAGAGCGGCAACAGCCAGGAGAGCGTCACCGAG CAGGACAGCAAGGACTCCACCTACAGCCTGAGCAGCACCCTGACC CTGAGCAAGGCCGACTACGAGAAGCATAAGGTGTACGCCTGCGAG GTGACCCACCAGGGCCTGTCCAGCCCCGTGACCAAGAGCTTCAAC AGGGGCGAGTGC |

NOV001

| | | |
|---|---|---|
| VH | 55 | QVQLVQSGAEVKKPGSSVKVSCKASGYTFTDYYINWVRQAPGQGL EWMGRIHPGSGNTYYNEKFQGRVTLTADKSTSTAYMELSSLRSED TAVYYCAILLLRSYGMDDWGQGTTVTVSS |
| Heavy Chain | 56 | QVQLVQSGAEVKKPGSSVKVSCKASGYTFTDYYINWVRQAPGQGL EWMGRIHPGSGNTYYNEKFQGRVTLTADKSTSTAYMELSSLRSED TAVYYCAILLLRSYGMDDWGQGTTVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKRVEPKSCDKT HTCPPCPAPEAAGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSREEM TKNQVSLTCLVKGFYPSDIAVEWESNGQPENNYKTTPPVLDSDGS FFLYSKLTVDKSRWQQGNVFSCSVMHEALHNHYTQKSLSLSPGK |

TABLE 2-continued

FGF21 mimetic antibodies

| | SEQ ID NO: | Amino Acid Sequence |
|---|---|---|
| VL | 57 | DVVMTQTPLSLSVTPGQPASISCKSSQSIVHSSGNTYLEWYLQKP GQSPQLLIYKVSNRFSGVPDRFSGSGSGTDFTLKISRVEAEDVGV YYCFQGSHIPYTFGQGTKLEIK |
| Light Chain | 58 | DVVMTQTPLSLSVTPGQPASISCKSSQSIVHSSGNTYLEWYLQKP GQSPQLLIYKVSNRFSGVPDRFSGSGSGTDFTLKISRVEAEDVGV YYCFQGSHIPYTFGQGTKLEIKRTVAAPSVFIFPPSDEQLKSGTA SVVCLLNNFYPREAKVQWKVDNALQSGNSQESVTEQDSKDSTYSL SSTLTLSKADYEKHKVYACEVTHQGLSSPVTKSFNRGEC |

NOV002

| | | |
|---|---|---|
| VH | 43 | EVQLVESGGGLVKPGGSLRLSCAVSGYSITSGYTWHWVRQAPGKG LEWLSYIHYSVYTNYNPSVKGRFTISRDTAKNSFYLQMNSLRAED TAVYYCARRTTSLERYFDVWGQGTLVTVSS |
| Heavy Chain | 59 | EVQLVESGGGLVKPGGSLRLSCAVSGYSITSGYTWHWVRQAPGKG LEWLSYIHYSVYTNYNPSVKGRFTISRDTAKNSFYLQMNSLRAED TAVYYCARRTTSLERYFDVWGQGTLVTVSSASTKGPSVFPLAPSS KSTSGGTAALGCLVKDYFPEPVTVSWNSGALTSGVHTFPAVLQSS GLYSLSSVVTVPSSSLGTQTYICNVNHKPSNTKVDKRVEPKSCDK THTCPPCPAPEAAGGPSVFLFPPKPKDTLMISRTPEVTCVVVDVS HEDPEVKFNWYVDGVEVHNAKTKPREEQYNSTYRVVSVLTVLHQD WLNGKEYKCKVSNKALPAPIEKTISKAKGQPREPQVYTLPPSREE MTKNQVSLTCLVKGFYPSDIAVEWESNGQPENNYKTTPPVLDSDG SFFLYSKLTVDKSRWQQGNVFSCSVMHEALHNHYTQKSLSLSPGK |
| VL | 47 | DIQMTQSPSSLSASVGDRVTITCQASQDISNYLNWYQQKPGKAPK LLIYYTSRLQSGVPSRFTGSGSGADYTFTISSLQPEDIATYFCQQ GNTLPYTFGQGTKLEIK |
| Light Chain | 60 | DIQMTQSPSSLSASVGDRVTITCQASQDISNYLNWYQQKPGKAPK LLIYYTSRLQSGVPSRFTGSGSGADYTFTISSLQPEDIATYFCQQ GNTLPYTFGQGTKLEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |

NOV003

| | | |
|---|---|---|
| VH | 55 | QVQLVQSGAEVKKPGSSVKVSCKASGYTFTDYYINWVRQAPGQGL EWMGRIHPGSGNTYYNEKFQGRVTLTADKSTSTAYMELSSLRSED TAVYYCAILLLRSYGMDDWGQGTTVTVSS |
| Heavy Chain | 61 | QVQLVQSGAEVKKPGSSVKVSCKASGYTFTDYYINWVRQAPGQGL EWMGRIHPGSGNTYYNEKFQGRVTLTADKSTSTAYMELSSLRSED TAVYYCAILLLRSYGMDDWGQGTTVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKRVEPKSCDKT HTCPPCPAPELLGGPSVFLFPPKPKDTLMISRTPEVTCVVVAVSH EDPEVKFNWYVDGVEVHNAKTKPREEQYNSTYRVVSVLTVLHQDW LNGKEYKCKVSNKALAAPIEKTISKAKGQPREPQVYTLPPSREEM TKNQVSLTCLVKGFYPSDIAVEWESNGQPENNYKTTPPVLDSDGS FFLYSKLTVDKSRWQQGNVFSCSVMHEALHNHYTQKSLSLSPGK |
| VL | 57 | DVVMTQTPLSLSVTPGQPASISCKSSQSIVHSSGNTYLEWYLQKP GQSPQLLIYKVSNRFSGVPDRFSGSGSGTDFTLKISRVEAEDVGV YYCFQGSHIPYTFGQGTKLEIK |
| Light Chain | 62 | DVVMTQTPLSLSVTPGQPASISCKSSQSIVHSSGNTYLEWYLQKP GQSPQLLIYKVSNRFSGVPDRFSGSGSGTDFTLKISRVEAEDVGV YYCFQGSHIPYTFGQGTKLEIKRTVAAPSVFIFPPSDEQLKSGTA SVVCLLNNFYPREAKVQWKVDNALQSGNSQESVTEQDSKDSTYSL SSTLTLSKADYEKHKVYACEVTHQGLSSPVTKSFNRGEC |

Other antibodies of the present disclosure include those where the amino acids or nucleic acids encoding the amino acids have been mutated, yet have at least 60, 65, 70, 75, 80, 85, 90, or 95 percent identity to the sequences described in Table 1. Some embodiments include mutant amino acid sequences wherein no more than 1, 2, 3, 4 or 5 amino acids have been mutated in the variable regions when compared with the variable regions depicted in the sequence described in Table 1, while retaining substantially the same antigen-binding activity.

Other antibodies of the present disclosure include those where the amino acids or nucleic acids encoding the amino acids have been mutated, yet have at least 60, 65, 70, 75, 80, 85, 90, or 95 percent identity to the sequences described in Table 1. Some embodiments include mutant amino acid sequences wherein no more than 1, 2, 3, 4 or 5 amino acids have been mutated in the variable regions when compared with the variable regions depicted in the sequence described in Table 1, while retaining substantially the same antigen-binding activity.

Since each of these antibodies can bind to β-klotho, the VH, VL, full length light chain, and full length heavy chain sequences (amino acid sequences and the nucleotide sequences encoding the amino acid sequences) can be "mixed and matched" to create other β-klotho-binding antibodies of the present disclosure. Such "mixed and matched"-β-klotho binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

Accordingly, in one aspect, the present disclosure provides an isolated antibody (e.g., monoclonal antibody) or antigen-binding region thereof having: a heavy chain variable domain comprising an amino acid sequence of SEQ ID NO: 15, and a light chain variable domain comprising an amino acid sequence of SEQ ID NO: 26 or 32, wherein the antibody specifically binds to β-klotho (e.g., human and cynomolgus monkey β-klotho).

In another aspect, the present disclosure provides (i) an isolated antibody having: a full length heavy chain comprising an amino acid sequence, that has been optimized for expression in a mammalian cell, of SEQ ID NO: 17, and a full length light chain comprising an amino acid sequence, that has been optimized for expression in a mammalian cell, of SEQ ID NO: 28 or 34; or (ii) a functional protein comprising an antigen-binding portion thereof. More specifically, in certain aspects, the present disclosure provides an isolated antibody or antigen-binding region thereof comprising a heavy chain and a light chain comprising amino acid sequences selected from SEQ ID NOs: 17 and 28; or 17 and 34, respectively.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or fragment comprises a heavy chain variable region (VH) comprising the amino acid sequence of SEQ ID NO: 15 or an amino acid sequence with at least 90% or 95% identity thereof; and a light chain variable region (VL) comprising the amino acid sequence of SEQ ID NO: 26 or 32 or an amino acid sequence with at least 90% or 95% identity thereof.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or fragment comprises a VH comprising the amino acid sequence of SEQ ID NO: 15.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or fragment comprises a VL comprising the amino acid sequence of SEQ ID NO: 26 or 32.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or fragment comprises a (i) a VH comprising the amino acid sequence of SEQ ID NO: 15 and a VL comprising the amino acid sequence of SEQ ID NO: 26 or (ii) a VH comprising the amino acid sequence of SEQ ID NO: 15 and a VL comprising the amino acid sequence of SEQ ID NO: 32.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody comprises (i) a heavy chain comprising the amino acid sequence of SEQ ID NO: 17 and a light chain comprising the amino acid sequence of SEQ ID NO: 28, or (ii) a heavy chain comprising the amino acid sequence of SEQ ID NO: 17 and a light chain comprising the amino acid sequence of SEQ ID NO: 34.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment does not comprise Combined or Kabat CDRs of antibody NOV004 as set forth in Table 2.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (CDR1), 51-57 (CDR2)

and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align. By combining the CDR definitions of both Kabat and Chothia, the "Combined" CDRs may consist of amino acid residues 26-35 (HCDR1), 50-65 (HCDR2), and 99-108 (HCDR3) in human VH and amino acid residues 24-39 (LCDR1), 55-61 (LCDR2), and 94-102 (LCDR3) in human VL.

In another aspect, the present disclosure provides β-klotho binding antibodies that comprise the heavy chain and light chain CDR1s, CDR2s, and CDR3s as described in Table 1, or combinations thereof. In specific aspects, these CDRs are delineated using the Kabat system. In another specific aspects, these CDRs are delineated using the Combined system.

Given that each of these antibodies can bind to β-klotho and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody preferably contains a VH CDR1, 2 and 3 and a VL CDR1, 2 and 3 to create other β-klotho binding molecules of the present disclosure. Such "mixed and matched" β-klotho binding antibodies can be tested using the binding assays known in the art and those described in the Examples (e.g., ELISAs, SET, Biacore® binding assays). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present disclosure. In addition to the foregoing, in one embodiment, the antigen-binding fragments of the antibodies described herein can comprise a VH CDR1, 2, and 3, or a VL CDR 1, 2, and 3, wherein the fragment binds to β-klotho as a single variable domain.

In certain embodiments of the present disclosure, the antibodies or antigen-binding fragments thereof may have the heavy and light chain sequences of the Fabs described in Table 1. More specifically, the antibody or antigen-binding fragments thereof may have the heavy and light sequence of Fab NOV005 or NOV006.

In certain embodiments of the present disclosure, the antibody or antigen-binding fragment that specifically hinds β-klotho comprises heavy chain variable region CDR1, CDR2, and CDR3 of Fab NOV005 or NOV006, and light chain variable region CDR1, CDR2, and CDR3 of Fab NOV005 or NOV006, for example, as set forth in Table 1.

In other embodiments of the present disclosure the antibody or antigen-binding fragment in that specifically binds β-klotho comprises a heavy chain variable region CDR1, a heavy chain variable region CDR2, a heavy chain variable region CDR3, a light chain variable region CDR1, a light chain variable region CDR2, and a light chain variable region CDR3 as defined by Kabat and described in Table 1. In still other embodiments of the present disclosure the antibody or antigen-binding fragment in that specifically binds β-klotho comprises a heavy chain variable region CDR1, a heavy chain variable region CDR2, a heavy chain variable region CDR3, a light chain variable region CDR1, a light chain variable region CDR2, and a light chain variable region CDR3 as defined by Chothia and described in Table 1. In still other embodiments of the present disclosure the antibody or antigen-binding fragment in that specifically binds β-klotho comprises a heavy chain variable region CDR1, a heavy chain variable region CDR2, a heavy chain variable region CDR3, a light chain variable region CDR1, a light chain variable region CDR2, and a light chain variable region CDR3 as defined by Combined Kabat and Chothia and described in Table 1. In still other embodiments of the present disclosure the antibody or antigen-binding fragment in that specifically binds β-klotho comprises a heavy chain variable region CDR1, a heavy chain variable region CDR2, a heavy chain variable region CDR3, a light chain variable region CDR1, a light chain variable region CDR2, and a light chain variable region CDR3 as defined by IMGT and described in Table 1.

In certain embodiments, the present disclosure includes antibodies or antigen-binding fragments that specifically bind to β-klotho as described in Table 1, e.g., antibody NOV005 or NOV006. In a preferred embodiment, the antibody, or antigen-binding fragment, that binds β-klotho and activates the FGF21 receptor complex is Fab NOV005 or NOV006.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment thereof comprises:

(i) a heavy chain CDR1 (HCDR1) comprising the amino acid sequence of SEQ ID NO: 6, 9, 10 or 12;

(ii) a heavy chain CDR2 (HCDR2) comprising the amino acid sequence of SEQ ID NO: 7, 11 or 13;

(iii) a heavy chain CDR3 (HCDR3) comprising the amino acid sequence of SEQ ID NO: 8, or 14;

(iv) a light chain CDR1 (LCDR1) comprising the amino acid sequence of SEQ ID NO: 19, 31, 22, or 25;

(v) a light chain CDR2 (LCDR2) comprising the amino acid sequence of SEQ ID NO: 20 or 23; and (vi) a light chain CDR3 (LCDR3) comprising the amino acid sequence of SEQ ID NO: 21 or 24.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment thereof comprises:

(i) a heavy chain CDR1 (HCDR1) comprising the amino acid sequence of SEQ ID NO: 6, 9, 10 or 12;

(ii) a heavy chain CDR2 (HCDR2) comprising the amino acid sequence of SEQ ID NO: 7, 11 or 13;

(iii) a heavy chain CDR3 (HCDR3) comprising the amino acid sequence of SEQ ID NO: 8, or 14;

(iv) a light chain CDR1 (LCDR1) comprising the amino acid sequence of SEQ ID NO: 31, 22, or 25;

(v) a light chain CDR2 (LCDR2) comprising the amino acid sequence of SEQ ID NO: 20 or 23; and (vi) a light chain CDR3 (LCDR3) comprising the amino acid sequence of SEQ ID NO: 21 or 24.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β- klotho receptor complex, wherein the antibody or antigen-binding fragment thereof comprises:
(i) a heavy chain CDR1 (HCDR1) comprising the amino acid sequence of SEQ ID NO: 6, 9, 10 or 12;
(ii) a heavy chain CDR2 (HCDR2) comprising the amino acid sequence of SEQ ID NO: 7, 11 or 13;
(iii) a heavy chain CDR3 (HCDR3) comprising the amino acid sequence of SEQ ID NO: 8, or 14;
(iv) a light chain CDR1 (LCDR1) comprising the amino acid sequence of SEQ ID NO: 19, 31, 22, or 25;
(v) a light chain CDR2 (LCDR2) comprising the amino acid sequence of SEQ ID NO: 20 or 23; and
(vi) a light chain CDR3 (LCDR3) comprising the amino acid sequence of SEQ ID NO: 21 or 24.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment thereof comprises a VH comprising HCDR1, HCDR2, and HCDR3, and a VL comprising LCDR1, LCDR2, and LCDR3, wherein:
the HCDR1 comprises the amino acid sequence of SEQ ID NO: 6, the HCDR2 comprises the amino acid sequence of SEQ ID NO: 7, the HCDR3 comprises the amino acid sequence of SEQ ID NO: 8, the LCDR1 comprises the amino acid sequence of SEQ ID NO: 31, the LCDR2 comprises the amino acid sequence of SEQ ID NO: 20, and the LCDR3 comprises the amino acid sequence of SEQ ID NO: 21.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment thereof comprises a VH comprising HCDR1, HCDR2, and HCDR3, and a VL comprising LCDR1, LCDR2, and LCDR3, wherein:
the HCDR1 comprises the amino acid sequence of SEQ ID NO: 9, the HCDR2 comprises the amino acid sequence of SEQ ID NO: 7, the HCDR3 comprises the amino acid sequence of SEQ ID NO: 8, the LCDR1 comprises the amino acid sequence of SEQ ID NO: 31, the LCDR2 comprises the amino acid sequence of SEQ ID NO: 20, and the LCDR3 comprises the amino acid sequence of SEQ ID NO: 21.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment thereof comprises a VH comprising HCDR1, HCDR2, and HCDR3, and a VL comprising LCDR1, LCDR2, and LCDR3, wherein:
the HCDR1 comprises the amino acid sequence of SEQ ID NO: 10, the HCDR2 comprises the amino acid sequence of SEQ ID NO: 11, the HCDR3 comprises the amino acid sequence of SEQ ID NO: 8, the LCDR1 comprises the amino acid sequence of SEQ ID NO: 22, the LCDR2 comprises the amino acid sequence of SEQ ID NO: 23, and the LCDR3 comprises the amino acid sequence of SEQ ID NO: 24.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment thereof comprises a VH comprising HCDR1, HCDR2, and HCDR3, and a VL comprising LCDR1, LCDR2, and LCDR3, wherein:
the HCDR1 comprises the amino acid sequence of SEQ ID NO: 12, the HCDR2 comprises the amino acid sequence of SEQ ID NO: 13, the HCDR3 comprises the amino acid sequence of SEQ ID NO: 14, the LCDR1 comprises the amino acid sequence of SEQ ID NO: 25, the LCDR2 comprises the amino acid sequence of SEQ ID NO: 23, and the LCDR3 comprises the amino acid sequence of SEQ ID NO: 21.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment thereof comprises a VH comprising HCDR1, HCDR2, and HCDR3, and a VL comprising LCDR1, LCDR2, and LCDR3, wherein:
(i) the HCDR1 comprises the amino acid sequence of SEQ ID NO: 6, the HCDR2 comprises the amino acid sequence of SEQ ID NO: 7, the HCDR3 comprises the amino acid sequence of SEQ ID NO: 8, the LCDR1 comprises the amino acid sequence of SEQ ID NO: 19, the LCDR2 comprises the amino acid sequence of SEQ ID NO: 20, and the LCDR3 comprises the amino acid sequence of SEQ ID NO: 21; or
(ii) the HCDR1 comprises the amino acid sequence of SEQ ID NO: 9, the HCDR2 comprises the amino acid sequence of SEQ ID NO: 7, the HCDR3 comprises the amino acid sequence of SEQ ID NO: 8, the LCDR1 comprises the amino acid sequence of SEQ ID NO: 19, the LCDR2 comprises the amino acid sequence of SEQ ID NO: 20, and the LCDR3 comprises the amino acid sequence of SEQ ID NO: 21.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment thereof comprises a VH comprising HCDR1, HCDR2, and HCDR3, and a VL comprising LCDR1, LCDR2, and LCDR3, wherein:
the HCDR1 comprises the amino acid sequence of SEQ ID NO: 10, the HCDR2 comprises the amino acid sequence of SEQ ID NO: 11, the HCDR3 comprises the amino acid sequence of SEQ ID NO: 8, the LCDR1 comprises the amino acid sequence of SEQ ID NO: 22, the LCDR2 comprises the amino acid sequence of SEQ ID NO: 23, and the LCDR3 comprises the amino acid sequence of SEQ ID NO: 24.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment thereof comprises a VH comprising HCDR1, HCDR2, and HCDR3, and a VL comprising LCDR1, LCDR2, and LCDR3, wherein:
the HCDR1 comprising the amino acid sequence of SEQ ID NO: 12, the HCDR2 comprises the amino acid sequence of SEQ ID NO: 13, the HCDR3 comprises the amino acid sequence of SEQ ID NO: 14, the LCDR1 comprises the amino acid sequence of SEQ ID NO: 25, the LCDR2 comprises the amino acid sequence of SEQ ID NO: 23, and the LCDR3 comprises the amino acid sequence of SEQ ID NO: 21.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment thereof comprises a VH comprising CDRs HCDR1, HCDR2 and HCDR3 and a VL comprising CDRs LCDR1, LCDR2, and LCDR3, wherein the antibody or antigen-binding fragment thereof comprises: a HCDR1 comprising the amino acid sequence of SEQ ID NO: 6, a HCDR2 comprising the amino acid sequence of SEQ ID NO: 7, a HCDR3 comprising the amino acid sequence of SEQ ID NO: 8, a LCDR1 comprising the amino acid sequence of SEQ ID NO: 19 or 31, a LCDR2 comprising the amino acid sequence of SEQ ID NO: 20, and a LCDR3 comprising the amino acid sequence of SEQ ID NO: 21.

In a specific aspect, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment thereof comprises a VH comprising CDRs HCDR1, HCDR2 and HCDR3 and a VL comprising CDRs LCDR1, LCDR2, and LCDR3, wherein the antibody or antigen-binding fragment thereof comprises: a HCDR1 comprising the amino acid sequence of SEQ ID NO: 9, a HCDR2 comprising the amino acid sequence of SEQ ID NO: 7, a HCDR3 comprising the amino acid sequence of SEQ ID NO: 8, a LCDR1 comprising the amino acid sequence of SEQ ID NO: 19 or 31, a LCDR2 comprising the amino acid sequence of SEQ ID NO: 20, and a LCDR3 comprising the amino acid sequence of SEQ ID NO: 21.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said antibody or fragment increases the activity of β-klotho and/or FGFR1c. In specific aspects, said antibody or fragment thereof increases the activity of β-klotho and/or FGFR1c, for example as determined by phospho-ERK activity, by at least about 10% or 20%. In specific aspects, said antibody or fragment thereof increases the activity of β-klotho and/or FGFR1c, for example as determined by phospho-ERK activity, by at least about 30% or 40%. In specific aspects, said antibody or fragment thereof increases the activity of β-klotho and/or FGFR1c, for example as determined by phospho-ERK activity, by at least about 50% or 60%. In specific aspects, said antibody or fragment thereof increases the activity of β-klotho and/or FGFR1c, for example as determined by phospho-ERK activity, by at least about 70% or 80%. In specific aspects, said antibody or fragment thereof increases the activity of β-klotho and/or FGFR1c, for example as determined by phospho-ERK activity, by at least about 90% or 95%.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment binds to a human β-klotho protein with a $K_D$ of less than or equal to 500 pM or 450 pM, for example as determined by BIACORE™ binding assays. In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment binds to a human β-klotho protein with a $K_D$ of less than or equal to 450 pM or 400 pM, for example as determined by BIACORE™ binding assays.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein the antibody or antigen-binding fragment binds to a human β-klotho protein with a $K_D$ of less than or equal to 10 pM or 20 pM, for example as determined by BIACORE™ binding assays.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said epitope of β-klotho comprises one or more amino acids of residues 246-265, 536-550, 834-857 and 959-986 of the β-klotho sequence (SEQ ID NO:52).

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said epitopes comprises one or more of amino acids of residues 646-670, 696-700, and 646-689 of the β-klotho sequence (SEQ ID NO:52).

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said antibody or antigen-binding fragment protects one or more amino acids of residues 246-265, 536-550, 834-857 and 959-986 of human β-klotho (SEQ ID NO:52), as determined by hydrogen-deuterium exchange (HDx).

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said antibody or antigen-binding fragment protects one or more amino acids of residues 646-670, 696-700, and 646-689 of the β-klotho sequence (SEQ ID NO:52).

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said antibody or fragment does not contact residues 701 (Tyr) or 703 (Arg) of human β-klotho (SEQ ID NO: 52).

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said antibody or antigen-binding fragment thereof is capable of activating the human FGFR1c_β-klotho receptor complex, for example, with an EC50 of less than or equal to 50 nM, as measured by pERK cell assays.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said antibody or antigen-binding fragment thereof is capable of activating the human FGFR1c_β-klotho receptor complex, for example, with an EC50 of less than or equal to 100 nM, as measured by pERK cell assays.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said antibody or antigen-binding fragment thereof is capable of activating the human FGFR1c_β-klotho receptor complex, for example, with an EC50 of less than or equal to 40 nM or 30 nM, as measured by pERK cell assays.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said antibody or antigen-binding fragment thereof is capable of activating a human FGFR1c_β-klotho receptor complex, for example, with an EC50 of less than or equal to 50 nM, as measured by pERK cell assays, and wherein the antibody or antigen-binding fragment thereof is not capable of activating an FGFR2c-β-klotho receptor complex, an FGFR3c-β-klotho receptor complex, and/or FGFR4-β-klotho receptor complex.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said antibody or antigen-binding fragment thereof is capable of activating the cynomolgus monkey FGFR1c_β-klotho receptor complex with an EC50 of less than or equal to 50 nM, as measured by pERK cell assays.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said antibody or antigen-binding fragment thereof is capable of activating the cynomolgus monkey FGFR1c_β-klotho receptor complex with an EC50 of less than or equal to 40 nM or 30 nM, as measured by pERK cell assays.

In specific aspects, provided herein is an isolated antibody (e.g., monoclonal antibody) or antigen-binding fragment thereof that binds to an epitope of β-klotho and induces activity of an FGF21 receptor complex, e.g., FGFR1c-β-klotho receptor complex, wherein said antibody or antigen-binding fragment thereof is capable of activating the cynomolgus monkey FGFR1c_β-klotho receptor complex with an EC50 of less than or equal to 20 nM, as measured by pERK cell assays. As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene.

Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Examples of human germline immunoglobulin genes include, but are not limited to the variable domain germline fragments described below, as well as DP47 and DPK9.

Homologous Antibodies

In yet another embodiment, the present disclosure provides an antibody, or an antigen-binding fragment thereof, comprising amino acid sequences that are homologous to the sequences described in Table 1, and the antibody binds to a β-klotho protein (e.g., human and cynomolgus monkey β-klotho), and retains the desired functional properties (e.g., activating or increasing the activity of a β-klotho/FGFR1c receptor complex and/or one or more activities of FGF21) of those antibodies described in Table 1.

For example, the present disclosure provides an isolated antibody (e.g., antibody capable of activating or increasing the activity of a β-klotho/FGFR1c receptor complex), or a functional antigen-binding fragment thereof, comprising a heavy chain variable domain and a light chain variable domain, wherein the heavy chain variable domain comprises an amino acid sequence that is at least 80%, at least 90%, 95%, 96%, 97%, 98%, or at least 99% identical to an amino acid sequence of SEQ ID NO: 15; the light chain variable domain comprises an amino acid sequence that is at least 80%, at least 90%, 95%, 96%, 97%, 98%, or at least 99% identical to an amino acid sequence of SEQ ID NO: 26 or 32; wherein the antibody specifically binds to β-klotho (e.g., human and cynomolgus monkey β-klotho) and induces activity of β-klotho, and wherein the heavy chain variable domain does not comprise an amino acid sequence set forth in Table 2, e.g., the amino acid sequence of SEQ ID NO: 43 or 55 and the light chain variable region does not comprise an amino acid sequence set forth in Table 2, e.g., the amino acid sequence of SEQ ID NO: 47 or 57. In certain aspects of the present disclosure the heavy and light chain sequences further comprise HCDR1, HCDR2, HCDR3, LCDR1, LCDR2, and LCDR3 sequences as defined by Kabat, for example as set forth in Table 1. In certain other aspects of the present disclosure the heavy and light chain sequences further comprise HCDR1, HCDR2, HCDR3, LCDR1, LCDR2, and LCDR3 sequences as defined by Chothia, for example as set forth in Table 1, respectively. In certain other aspects of the present disclosure the heavy and light chain sequences further comprise HCDR1, HCDR2, HCDR3, LCDR1, LCDR2, and LCDR3 sequences as defined by Combined, for example as set forth in Table 1, respectively. In certain other aspects of the present disclosure the heavy and light chain sequences further comprise HCDR1, HCDR2, HCDR3, LCDR1, LCDR2, and LCDR3 sequences as defined by IMGT, for example as set forth in Table 1, respectively.

For example, the present disclosure provides an isolated antibody (e.g., antibody capable of activating or increasing the activity of a β-klotho/FGFR1c receptor complex), or a functional antigen-binding fragment thereof, comprising a heavy chain variable domain and a light chain variable domain, wherein the heavy chain variable domain comprises an amino acid sequence that is at least 80%, at least 90%, 95%, 96%, 97%, 98%, or at least 99% identical to an amino acid sequence of SEQ ID NOs: 15; the light chain variable domain comprises an amino acid sequence that is at least 80%, at least 90%, 95%, 96%, 97%, 98%, or at least 99% identical to an amino acid sequence of SEQ ID NOs: 26 or 32; wherein the antibody specifically binds to β-klotho (e.g., human and cynomolgus monkey β-klotho), and wherein the heavy chain variable domain does not comprise an amino acid sequence set forth in Table 2, e.g., the amino acid sequence of SEQ ID NO: 43 or 55 and the light chain variable region does not comprise an amino acid sequence set forth in Table 2, e.g., the amino acid sequence of SEQ ID NO: 47 or 57. In certain aspects of the present disclosure the heavy and light chain sequences further comprise HCDR1, HCDR2, HCDR3, LCDR1, LCDR2, and LCDR3 sequences as defined by Kabat, for example as set forth in Table 1. In certain other aspects of the present disclosure the heavy and light chain sequences further comprise HCDR1, HCDR2, HCDR3, LCDR1, LCDR2, and LCDR3 sequences as defined by Chothia, for example as set forth in Table 1. In certain other aspects of the present disclosure the heavy and light chain sequences further comprise HCDR1, HCDR2, HCDR3, LCDR1, LCDR2, and LCDR3 sequences as defined by Combined, for example as set forth in Table 1. In certain other aspects of the present disclosure the heavy and light chain sequences further comprise HCDR1, HCDR2, HCDR3, LCDR1, LCDR2, and LCDR3 sequences as defined by IMGT, for example as set forth in Table 1.

In other embodiments, the VH and/or VL amino acid sequences may be 50%, 60%, 70%, 80%, 90%, 95%, 96%, 97%, 98% or 99% identical to the sequences set forth in Table 1, wherein the heavy chain variable domain does not comprise an amino acid sequence set forth in Table 2, e.g., the amino acid sequence of SEQ ID NO: 43 or 55 and the light chain variable region does not comprise an amino acid sequence set forth in Table 2, e.g., the amino acid sequence of SEQ ID NO: 47 or 57. In other embodiments, the VH and/or VL amino acid sequences may be identical except for an amino acid substitution in no more than 1, 2, 3, 4 or 5 amino acid positions. An antibody having VH and VL regions having high (i.e., 80% or greater) identity to the VH and VL regions of those described in Table 1 can be obtained by mutagenesis (e.g., site-directed or PCR-mediated mutagenesis) of nucleic acid molecules encoding SEQ ID NOs: 10, 30, 50, or 70 and SEQ ID NOs: 20, 40, 60, or 80, respectively, followed by testing of the encoded altered antibody for retained function using the functional assays described herein, wherein the heavy chain variable domain does not comprise an amino acid sequence set forth in Table 2, e.g., the amino acid sequence of SEQ ID NO: 43 or 55 and the light chain variable region does not comprise an amino acid sequence set forth in Table 2, e.g., the amino acid sequence of SEQ ID NO: 47 or 57.

In other embodiments, the full length heavy chain and/or full length light chain amino acid sequences may be 50% 60%, 70%, 80%, 90%, 95%, 96%, 97%, 98% or 99% identical to the sequences set forth in Table 1, wherein the heavy chain does not comprise a heavy chain amino acid sequence set forth in Table 2, e.g., the amino acid sequence of SEQ ID NO: 45, 56, 59, or 61, and the light chain does not comprise a light chain amino acid sequence set forth in Table 2, e.g., the amino acid sequence of SEQ ID NO: 49, 58, 60, or 62. An antibody having a full length heavy chain and full length light chain having high (i.e., 80% or greater) identity to the full length heavy chain of SEQ ID NO: 17, and full length light chain of SEQ ID NO: 28 or 34, can be obtained by mutagenesis (e.g., site-directed or PCR-mediated mutagenesis) of nucleic acid molecules encoding such polypeptides, followed by testing of the encoded altered antibody for retained function using the functional assays described herein, wherein the heavy chain does not comprise a heavy chain amino acid sequence set forth in Table 2, e.g., the amino acid sequence of SEQ ID NO: 45, 56, 59, or 61, and the light chain does not comprise a light chain amino acid sequence set forth in Table 2, e.g., the amino acid sequence of SEQ ID NO: 49, 58, 60, or 62. An antibody having a full length heavy chain and full length light chain having high (i.e., 80% or greater) identity to the full length heavy chain of SEQ ID NO: 17, and full length light chain of SEQ ID NO: 28 or 34, can be obtained by mutagenesis (e.g., site-directed or PCR-mediated mutagenesis) of nucleic acid molecules encoding such polypeptides, followed by testing of the encoded altered antibody for retained function using the functional assays described herein, wherein the heavy chain does not comprise a heavy chain amino acid sequence set forth in Table 2, e.g., the amino acid sequence of SEQ ID NO: 45, 56, 59, or 61, and the light chain does not comprise a light chain amino acid sequence set forth in Table 2, e.g., the amino acid sequence of SEQ ID NO: 49, 58, 60, or 62.

In other embodiments, the full length heavy chain and/or full length light chain nucleotide sequences may be 60%, 70%, 80%, 90%, 95%, 96%, 97%, 98% or 99% identical to the sequences set forth in Table 1, wherein the heavy chain does not comprise a heavy chain amino acid sequence set forth in Table 2, e.g., the amino acid sequence of SEQ ID NO: 45, 56, 59, or 61, and the light chain does not comprise a light chain amino acid sequence set forth in Table 2, e.g., the amino acid sequence of SEQ ID NO: 49, 58, 60, or 62.

In other embodiments, the variable regions of heavy chain and/or the variable regions of light chain nucleotide sequences may be 60%, 70%, 80%, 90%, 95%, 96%, 97%, 98% or 99% identical to the sequences set forth in Table 1, wherein the heavy chain does not comprise a heavy chain amino acid sequence set forth in Table 2, e.g., the amino acid sequence of SEQ ID NO: 45, 56, 59, or 61, and the light chain does not comprise a light chain amino acid sequence set forth in Table 2, e.g., the amino acid sequence of SEQ ID NO: 49, 58, 60, or 62.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present disclosure can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In certain embodiments, an antibody of the present disclosure has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the β-klotho-binding antibodies of the present disclosure.

Accordingly, the present disclosure provides an isolated antibody (e.g., antibody capable of activating or increasing the activity of a β-klotho/FGFR1c receptor complex), or a antigen-binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NO: 6, and conservative modifications thereof; the heavy chain variable region CDR2 amino acid sequences are selected from the group consisting of SEQ ID NO: 7, and conservative modifications thereof; the heavy chain variable region CDR3 amino acid sequences are selected from the group consisting of SEQ ID NO: 8, and conservative modifications thereof; the light chain variable regions CDR1 amino acid sequences are selected from the group consisting of SEQ ID NOs: 19 and 31, and conservative modifications thereof; the light chain variable regions CDR2 amino acid sequences are selected from the group consisting of SEQ ID NO: 20, and conservative modifications thereof; the light chain variable regions of CDR3 amino acid sequences are selected from the group consisting of SEQ ID NO: 21, and conservative modifications thereof; and the antibody or antigen-binding fragments thereof specifically binds to β-klotho.

Accordingly, the present disclosure provides an isolated antibody (e.g., antibody capable of activating or increasing the activity of a β-klotho/FGFR1c receptor complex), or a antigen-binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 6, 9, 10, and 12, and conservative modifications thereof; the heavy chain variable region CDR2 amino acid sequences are selected from the group consisting of SEQ ID NOs: 7, 11, and 13, and conservative modifications thereof; the heavy chain variable region CDR3 amino acid sequences are selected from the group consisting of SEQ ID NOs: 8 and 14, and conservative modifications thereof; the light chain variable regions CDR1 amino acid sequences are selected from the group consisting of SEQ ID NOs: 19, 31, 22, and 25, and conservative modifications thereof; the light chain variable regions CDR2 amino acid sequences are selected from the group consisting of SEQ ID NOs: 20 and 23, and conservative modifications thereof; the light chain variable regions of CDR3 amino acid sequences are selected from the group consisting of SEQ ID NOs: 21 or 24, and conservative modifications thereof; and the antibody or antigen-binding fragments thereof specifically binds to β-klotho.

In one aspect, the present disclosure provides an isolated antibody optimized for expression in a mammalian cell comprising a heavy chain variable region and a light chain variable region wherein the heavy chain variable region has amino acid sequences selected from the group of SEQ ID NO: 15, and conservative modifications thereof; and the full length light chain has amino acid sequences selected from the group of SEQ ID NOs: 26 and 32, and conservative modifications thereof; and the antibody specifically binds to β-klotho (e.g., human and cynomolgus monkey β-klotho), and wherein the heavy chain variable region does not comprise a heavy chain variable region amino acid sequence set forth in Table 2, e.g., the amino acid sequence of SEQ ID NO: 43 or 55 and the light chain variable region does not comprise a light chain variable region amino acid sequence set forth in Table 2, e.g., the amino acid sequence of SEQ ID NO: 47 or 57.

In other embodiments, the antibody of the present disclosure is optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the β-klotho binding antibodies of the present disclosure. Accordingly, the present disclosure provides an isolated antibody optimized for expression in a mammalian cell consisting of a full length heavy chain and a full length light chain wherein the full length heavy chain has amino acid sequences selected from the group of SEQ ID NO: 17, and conservative modifications thereof; and the full length light chain has amino acid sequences selected from the group of SEQ ID NOs: 28 and 34, and conservative modifications thereof; and the antibody specifically binds to β-klotho (e.g., human and cynomolgus monkey β-klotho), and wherein the heavy chain does not comprise a heavy chain amino acid sequence set forth in Table 2, e.g., the amino acid sequence of SEQ ID NO: 45, 56, 59, or 61, and the light chain does not comprise a light chain amino acid sequence set forth in Table 2, e.g., the amino acid sequence of SEQ ID NO: 49, 58, 60, or 62.

Antibodies that Bind to the Same Epitope(s) or that Compete for Binding to the Same Epitope(s)

The present disclosure provides antibodies (e.g., antibodies capable of activating or increasing the activity of a β-klotho/FGFR1c receptor complex) that bind to the same epitope as the β-klotho binding antibodies described in Table 1 (e.g., NOV005 or NOV006). In a particular aspect, such antibodies and antigen-binding fragments are capable of increasing the activity of β-klotho and FGFR1c. Additional antibodies can therefore be identified based on their ability to compete (e.g., to competitively inhibit the binding of, in a statistically significant manner) with other antibodies of the present disclosure in β-klotho binding assays (such as those described in the Examples). The ability of a test antibody to inhibit the binding of antibodies of the present disclosure to a β-klotho protein demonstrates that the test antibody can compete with that antibody for binding to β-klotho: such an antibody may, according to non-limiting theory, bind to the same or a related (e.g., a structurally similar or spatially proximal) epitope on the β-klotho protein as the antibody with which it competes. In a certain embodiment, the antibody that binds to the same epitope on β-klotho as the antibodies of the present disclosure is a human monoclonal antibody. Such human monoclonal antibodies can be prepared and isolated as described herein. As used herein, an antibody "competes" for binding when the competing antibody inhibits β-klotho binding of an antibody or antigen-binding fragment of the present disclosure by more than 50% (for example, 80%, 85%, 90%, 95%, 98% or 99%) in the presence of an equimolar concentration of competing antibody. In a certain embodiment, the antibody that binds to the same epitope on β-klotho as the antibodies of the present disclosure is a humanized monoclonal antibody. Such humanized monoclonal antibodies can be prepared and isolated as described herein.

In a particular aspect, the present disclosure provides antibodies (e.g., antibody capable of activating or increasing the activity of a β-klotho/FGFR1c receptor complex) that bind to the same epitope as β-klotho binding antibody NOV005 or NOV006.

In a particular aspect, the present disclosure provides antibodies (e.g., antibody capable of activating or increasing the activity of a β-klotho/FGFR1c receptor complex) that bind to the same epitope as a β-klotho binding antibody which comprises a heavy chain variable region (VH) comprising the amino acid sequence of SEQ ID NO: 15 and a light chain variable region (VL) comprising the amino acid sequence of SEQ ID NO: 26 or 32.

In a particular aspect, the present disclosure provides antibodies (e.g., antibody capable of activating or increasing the activity of a β-klotho/FGFR1c receptor complex) that bind to the same epitope as a β-klotho binding antibody which comprises a heavy chain variable region (VH) comprising the amino acid sequence of SEQ ID NO: 15 and a light chain variable region (VL) comprising the amino acid sequence of SEQ ID NO: 26.

In a particular aspect, the present disclosure provides antibodies that bind to the same epitope as a β-klotho binding antibody which comprises a heavy chain variable region (VH) comprising the amino acid sequence of SEQ ID NO: 15 and a light chain variable region (VL) comprising the amino acid sequence of SEQ ID NO: 32.

In a particular aspect, the present disclosure provides antibodies (e.g., antibody capable of activating or increasing the activity of a β-klotho/FGFR1c receptor complex) that bind to an overlapping epitope as β-klotho binding antibody NOV005 or NOV006.

In a particular aspect, the present disclosure provides antibodies (e.g., antibody capable of activating or increasing the activity of a β-klotho/FGFR1c receptor complex) that bind to an overlapping epitope as a β-klotho binding antibody which comprises a heavy chain variable region (VH) comprising the amino acid sequence of SEQ ID NO: 15 and a light chain variable region (VL) comprising the amino acid sequence of SEQ ID NO: 26 or 32.

In a particular aspect, the present disclosure provides antibodies (e.g., antibody capable of activating or increasing the activity of a β-klotho/FGFR1c receptor complex) that bind to an overlapping epitope as a β-klotho binding antibody which comprises a heavy chain variable region (VH) comprising the amino acid sequence of SEQ ID NO: 15 and a light chain variable region (VL) comprising the amino acid sequence of SEQ ID NO: 26.

In a particular aspect, the present disclosure provides antibodies (e.g., antibody capable of activating or increasing the activity of a β-klotho/FGFR1c receptor complex) that bind to an overlapping epitope as a β-klotho binding antibody which comprises a heavy chain variable region (VH) comprising the amino acid sequence of SEQ ID NO: 15 and a light chain variable region (VL) comprising the amino acid sequence of SEQ ID NO: 32.

In a particular aspect, provided herein is an isolated antibody (e.g., antibody capable of activating or increasing the activity of a β-klotho/FGFR1c receptor complex) or antigen-binding fragment thereof that binds to an epitope of β-klotho, wherein said epitope comprises one or more amino acids of residues 246-265 of the β-klotho sequence (SEQ ID NO: 52). In a particular aspect, provided herein is an isolated antibody (e.g., antibody capable of activating or increasing the activity of a β-klotho/FGFR1c receptor complex) or antigen-binding fragment thereof that binds to an epitope of β-klotho, wherein said epitope comprises one or more amino acids of residues 536-550 of the β-klotho sequence (SEQ ID NO:52). In a particular aspect, provided herein is an isolated antibody (e.g., antibody capable of activating or increasing the activity of a β-klotho/FGFR1c receptor complex) or antigen-binding fragment thereof that binds to an epitope of β-klotho, wherein said epitope comprises one or more amino acids of residues 834-857 of the β-klotho sequence (SEQ ID NO:52). In a particular aspect, provided herein is an isolated antibody (e.g., antibody capable of activating or increasing the activity of a β-klotho/FGFR1c receptor complex) or antigen-binding fragment thereof that binds to an epitope of β-klotho, wherein said epitope comprises one or more amino acids of residues 959-986 of the β-klotho sequence (SEQ ID NO:52).

In a particular aspect, provided herein is an isolated antibody (e.g., antibody capable of activating or increasing the activity of a β-klotho/FGFR1c receptor complex) or antigen-binding fragment thereof that binds to an epitope of β-klotho, wherein said epitope comprises one or more amino acids of residues 246-265, 536-550, 834-857 and 959-986 of the β-klotho sequence (SEQ ID NO:52). In specific aspects, provided herein is an isolated antibody (e.g., antibody capable of activating or increasing the activity of a β-klotho/FGFR1c receptor complex) or antigen-binding fragment thereof that binds to an epitope of β-klotho, wherein said epitope comprises two or more amino acids of residues 246-265, 536-550, 834-857 and 959-986 of the β-klotho sequence (SEQ ID NO:52). In specific aspects, provided herein is an isolated antibody (e.g., antibody capable of activating or increasing the activity of a β-klotho/FGFR1c receptor complex) or antigen-binding fragment thereof that binds to an epitope of β-klotho, wherein said epitope comprises three or more amino acids of residues 246-265, 536-550, 834-857 and 959-986 of the β-klotho sequence (SEQ ID NO:52). In specific aspects, provided herein is an isolated antibody (e.g., antibody capable of activating or increasing the activity of a β-klotho/FGFR1c receptor complex) or antigen-binding fragment thereof that binds to an epitope of β-klotho, wherein said epitope comprises amino acids of residues 246-265, 536-550, 834-857 and 959-986 of the β-klotho sequence (SEQ ID NO:52). In specific aspects, provided herein is an isolated antibody (e.g., antibody capable of activating or increasing the activity of a β-klotho/FGFR1c receptor complex) or antigen-binding fragment thereof that binds to an epitope of β-klotho, wherein said epitope comprises at least one amino acid residue from each of the following stretches of amino acid residues: 246-265, 536-550, 834-857 and 959-986 of the β-klotho sequence (SEQ ID NO:52).

In a particular aspect, provided herein is an isolated antibody (e.g., antibody capable of activating or increasing the activity of a β-klotho/FGFR1c receptor complex) or antigen-binding fragment thereof that binds to one or more epitopes of β-klotho, wherein said epitopes comprises one or more of amino acids of residues 646-670 of the β-klotho sequence (SEQ ID NO:52). In a particular aspect, provided herein is an isolated antibody (e.g., antibody capable of activating or increasing the activity of a β-klotho/FGFR1c receptor complex) or antigen-binding fragment thereof that binds to one or more epitopes of β-klotho, wherein said epitopes comprises one or more of amino acids of residues 696-700 of the β-klotho sequence (SEQ ID NO:52). In a particular aspect, provided herein is an isolated antibody (e.g., antibody capable of activating or increasing the activity of a β-klotho/FGFR1c receptor complex) or antigen-binding fragment thereof that binds to one or more epitopes of β-klotho, wherein said epitopes comprises one or more of amino acids of residues 646-689 of the β-klotho sequence (SEQ ID NO:52).

In a particular aspect, provided herein is an isolated antibody (e.g., antibody capable of activating or increasing the activity of a β-klotho/FGFR1c receptor complex) or antigen-binding fragment thereof that binds to one or more epitopes (e.g., discontinuous epitopes) of β-klotho, wherein said epitopes comprises one, or two, or three, or four, or five, or more of amino acids of residues 646-670, 696-700, and 646-689 of the β-klotho sequence (SEQ ID NO:52). In a certain aspect, provided herein is an isolated antibody (e.g., antibody capable of activating or increasing the activity of a β-klotho/FGFR1c receptor complex) or antigen-binding fragment thereof that binds to two or more epitopes (e.g., discontinuous epitopes) of β-klotho, wherein said epitopes comprises one or more of amino acids of residues 646-670, 696-700, and 646-689 of the β-klotho sequence (SEQ ID NO:52). In a specific aspect, provided herein is an isolated antibody (e.g., antibody capable of activating or increasing the activity of a β-klotho/FGFR1c receptor complex) or antigen-binding fragment thereof that binds to three or more epitopes (e.g., discontinuous epitopes) of β-klotho, wherein said epitopes comprises one or more of amino acids of residues 646-670, 696-700, and 646-689 of the β-klotho sequence (SEQ ID NO:52). In a specific aspect, provided herein is an isolated antibody (e.g., antibody capable of activating or increasing the activity of a β-klotho/FGFR1c receptor complex) or antigen-binding fragment thereof that binds to three or more epitopes (e.g., discontinuous epitopes) of β-klotho, wherein said epitopes comprises amino acids of residues 646-670, 696-700, and 646-689 of the β-klotho sequence (SEQ ID NO:52). In a specific aspect, provided herein is an isolated antibody (e.g., antibody capable of activating or increasing the activity of a β-klotho/FGFR1c receptor complex) or antigen-binding fragment thereof that binds to three or more epitopes (e.g., discontinuous epitopes) of β-klotho, wherein said epitopes comprises amino acid residues from each of the following ranges of amino acid residues: 646-670, 696-700, and 646-689 of the β-klotho sequence (SEQ ID NO:52).

In a particular aspect, provided herein is an isolated antibody (e.g., antibody capable of activating or increasing the activity of a β-klotho/FGFR1c receptor complex) or antigen-binding fragment thereof that protects, as determined by hydrogen-deuterium exchange (HDx), one, two, three, four, five, or more of the following peptides of β-klotho (SEQ ID NO: 52): amino acid residues 245-266, 246-265, 343-349, 344-349, 421-429, 488-498, 509-524, 536-550, 568-576, 646-669, 646-670, 696-700, 773-804, 834-857, and 959-986.

In a particular aspect, provided herein is an isolated antibody (e.g., antibody capable of activating or increasing the activity of a β-klotho/FGFR1c receptor complex) or antigen-binding fragment thereof that protects, as determined by hydrogen-deuterium exchange (HDx), the following peptides of β-klotho (SEQ ID NO: 52): amino acid residues 246-265, 536-550, 834-857 and 959-986.

In a particular aspect, provided herein is an isolated antibody (e.g., antibody capable of activating or increasing the activity of a β-klotho/FGFR1c receptor complex) or antigen-binding fragment thereof that protects, as determined by hydrogen-deuterium exchange (HDx), the following peptides of β-klotho (SEQ ID NO: 52): amino acid residues 245-266, 246-265, 343-349, 344-349, 421-429, 488-498, 509-524, 536-550, 568-576, 646-669, 646-670, 696-700, 773-804, 834-857, and 959-986.

In certain aspects, provided herein is isolated antibody (e.g., antibody capable of activating or increasing the activity of a β-klotho/FGFR1c receptor complex) or antigen-binding fragment thereof, which increases the activity of β-klotho and FGFR1c, wherein the antibody or antigen-binding fragment thereof does not contact residues 701 (Tyr) or 703 (Arg) of human β-klotho (SEQ ID NO: 52).

In a particular aspect, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts one or more amino acids of residues 246-265 of the β-klotho sequence (SEQ ID NO: 52), for example as determined by x-ray crystallography, hydrogen-deuterium exchange assay, or scanning mutagenesis. In a particular aspect, provided herein is an isolated antibody (e.g., antibody capable of activating or increasing the activity of a β-klotho/FGFR1c receptor complex) or antigen-binding fragment thereof that hinds to β-klotho, wherein said antibody (e.g., antibody capable of activating or increasing the activity of a β-klotho/FGFR1c receptor complex) or antigen-binding fragment thereof contacts one or more amino acids of residues 536-550 of the β-klotho sequence (SEQ ID NO:52), for example as determined by x-ray crystallography, hydrogen-deuterium exchange assay, or scanning mutagenesis. In a particular aspect, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts one or more amino acids of residues 834-857 of the β-klotho sequence (SEQ ID NO:52), for example as determined by x-ray crystallography, hydrogen-deuterium exchange assay, or scanning mutagenesis. In a particular aspect, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts one or more amino acids of residues 959-986 of the β-klotho sequence (SEQ ID NO:52), for example as determined by x-ray crystallography, hydrogen-deuterium exchange assay, or scanning mutagenesis.

In a particular aspect, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts one or more amino acids of residues 246-265, 536-550, 834-857 and 959-986 of the β-klotho sequence (SEQ ID NO:52), for example as determined by x-ray crystallography, hydrogen-deuterium exchange assay, or scanning mutagenesis. In specific aspects, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts two or more amino acids of residues 246-265, 536-550, 834-857 and 959-986 of the β-klotho sequence (SEQ ID NO:52), for example as determined by x-ray crystallography, hydrogen-deuterium exchange assay, or scanning mutagenesis. In specific aspects, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts three or more amino acids of residues 246-265, 536-550, 834-857 and 959-986 of the β-klotho sequence (SEQ ID NO:52), for example as determined by x-ray crystallography, hydrogen-deuterium exchange assay, or scanning mutagenesis. In specific aspects, provided herein is an isolated antibody (e.g., antibody capable of activating or increasing the activity of a β-klotho/FGFR1c receptor complex) or antigen-binding fragment thereof that binds β-klotho, wherein said antibody or antigen-binding fragment thereof contacts amino acids of residues 246-265, 536-550, 834-857 and 959-986 of the β-klotho sequence (SEQ ID NO:52), for example as determined by x-ray crystallography, hydrogen-deuterium exchange assay, or scanning mutagenesis. In specific aspects, provided herein is an isolated antibody (e.g., antibody capable of activating or increasing the activity of a β-klotho/FGFR1c receptor complex) or antigen-binding fragment thereof that binds β-klotho, wherein said antibody or antigen-binding fragment thereof contacts at least one amino acid residue from each of the following stretches of amino acid residues: 246-265, 536-550, 834-857 and 959-986 of the β-klotho sequence (SEQ ID NO:52), for example as determined by x-ray crystallography, hydrogen-deuterium exchange assay, or scanning mutagenesis.

In a particular aspect, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts one or more of amino acids of residues 646-670 of the β-klotho sequence (SEQ ID NO:52), for example as determined by x-ray crystallography, hydrogen-deuterium exchange assay, or scanning mutagenesis. In a particular aspect, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts one or more of amino acids of residues 696-700 of the β-klotho sequence (SEQ ID NO:52), for example as determined by x-ray crystallography, hydrogen-deuterium exchange assay, or scanning mutagenesis. In a particular aspect, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts one or more of amino acids of residues 646-689 of the β-klotho sequence (SEQ ID NO:52), for example as determined by x-ray crystallography, hydrogen-deuterium exchange assay, or scanning mutagenesis.

In a particular aspect, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts one, or two, or three, or four, or five, or more of amino acids of residues 646-670, 696-700, and 646-689 of the β-klotho sequence (SEQ ID NO:52), for example as determined by x-ray crystallography, hydrogen-deuterium exchange assay, or scanning mutagenesis. In a certain aspect, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts one or more of the amino acid residues from each of the following stretches of amino acid residues 646-670, 696-700, and 646-689 of the β-klotho sequence (SEQ ID NO:52), for example as determined by x-ray crystallography, hydrogen-deuterium exchange assay, or scanning mutagenesis. In a specific aspect, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts one or more of the amino acid residues from each of the following stetches of amino acid residues 646-670, 696-700, and 646-689 of the β-klotho sequence (SEQ ID NO:52), for example as determined by x-ray crystallography, hydrogen-deuterium exchange assay, or scanning mutagenesis. In a specific aspect, provided herein is an isolated antibody (e.g., antibody capable of activating or increasing the activity of a β-klotho/FGFR1c receptor complex) or antigen-binding fragment thereof that binds to β-klotho, wherein said antibody or antigen-binding fragment thereof contacts amino acid residues 646-670, 696-700, and 646-689 of the β-klotho sequence (SEQ ID NO:52), for example as determined by x-ray crystallography, hydrogen-deuterium exchange assay, or scanning mutagenesis.

In a particular aspect, the present disclosure provides antibodies (e.g., antibody capable of activating or increasing the activity of a β-klotho/FGFR1c receptor complex) that compete with antibody NOV005 or NOV006 for binding to β-klotho.

In a particular aspect, the present disclosure provides antibodies (e.g., antibody capable of activating or increasing the activity of a β-klotho/FGFR1c receptor complex) that compete for binding to β-klotho with a β-klotho binding antibody which comprises a heavy chain variable region (VH) comprising the amino acid sequence of SEQ ID NO: 15 and a light chain variable region (VL) comprising the amino acid sequence of SEQ ID NO: 26 or 32.

In a particular aspect, the present disclosure provides antibodies (e.g., antibody capable of activating or increasing the activity of a β-klotho/FGFR1c receptor complex) that compete for binding to β-klotho with a β-klotho binding antibody which comprises a heavy chain variable region (VH) comprising the amino acid sequence of SEQ ID NO: 15 and a light chain variable region (VL) comprising the amino acid sequence of SEQ ID NO: 26.

In a particular aspect, the present disclosure provides antibodies (e.g., antibody capable of activating or increasing the activity of a β-klotho/FGFR1c receptor complex) that compete for binding to β-klotho with a β-klotho binding antibody which comprises a heavy chain variable region (VH) comprising the amino acid sequence of SEQ ID NO: 15 and a light chain variable region (VL) comprising the amino acid sequence of SEQ ID NO: 32.

Engineered and Modified Antibodies

An antibody (e.g., NOV005 or NOV006) of the present disclosure further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.).

Accordingly, another embodiment of the present disclosure pertains to an isolated antibody, or an antigen-binding fragment thereof, comprising a heavy chain variable region comprising CDR1 sequences having an amino acid sequence selected from the HCDR1 sequences set forth in Table 1; CDR2 sequences having an amino acid sequence selected from the HCDR2 sequences set forth in Table 1; CDR3 sequences having an amino acid sequence selected from the HCDR3 sequences set forth in table 1; and a light chain variable region having CDR1 sequences having an amino acid sequence selected from the LCDR1 sequences set forth in Table 1; CDR2 sequences having an amino acid sequence selected from the LCDR2 sequences set forth in Table 1; and CDR3 sequences consisting of an amino acid sequence selected from the LCDR3 sequences set forth in Table 1. Thus, such antibodies contain the VH and VL CDR sequences of monoclonal antibodies, yet may contain different framework sequences from these antibodies.

Accordingly, another embodiment of the present disclosure pertains to an isolated antibody, or an antigen-binding fragment thereof, comprising a heavy chain variable region comprising CDR1 sequences comprising an amino acid sequence selected from the group consisting of SEQ ID NOs: 6 and 9; CDR2 sequences comprising an amino acid sequence of SEQ ID NO: 7; CDR3 sequences comprising an amino acid sequence of SEQ ID NO: 8; and a light chain variable region having CDR1 sequences comprising an amino acid sequence selected from the group consisting of SEQ ID NOs: 19 and 31; CDR2 sequences comprising an amino acid sequence of SEQ ID NO: 20; and CDR3 sequences consisting of an amino acid sequence of SEQ ID NO: 21. Thus, such antibodies contain the VH and VL CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in the antibodies of the present disclosure are those that are structurally similar to the framework sequences used by selected antibodies of the present disclosure, e.g., consensus sequences and/or framework sequences used by monoclonal antibodies of the present disclosure. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen-binding ability of the antibody (see e.g., U.S. Pat. Nos. 5,530,101; 5,585,089; 5,693,762 and 6,180,370 to Queen et al). Frameworks that can be utilized as scaffolds on which to build the antibodies and antigen-binding fragments described herein include, but are not limited to VH1A, VH1B, VH3, Vk1, V12, and Vk2. Additional frameworks are known in the art and may be found, for example, in the vBase data base on the world wide web at vbase.mrc-cpe.cam.ac.uk/index.php?&MMN_position=1:1.

Accordingly, an embodiment of the present disclosure relates to isolated β-klotho binding antibodies, or antigen-binding fragments thereof, comprising a heavy chain variable region comprising an amino acid sequence of SEQ ID NOs: 15, or an amino acid sequence having one, two, three, four or five amino acid substitutions, deletions or additions in the framework region of such sequences, and further comprising a light chain variable region having an amino acid sequence selected from the group consisting of SEQ ID NOs: 26 or 32, or an amino acid sequence having one, two, three, four or five amino acid substitutions, deletions or additions in the framework region of such sequences, wherein the heavy chain variable region does not comprise a heavy chain variable region amino acid sequence set forth in Table 2, e.g., the amino acid sequence of SEQ ID NO: 43 or 55 and the light chain variable region does not comprise a light chain variable region amino acid sequence set forth in Table 2, e.g., the amino acid sequence of SEQ ID NO: 47 or 57.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Certain amino acid sequence motifs are known to undergo post-translational modification (PTM) such as glycosylation (i.e. NxS/T, x any but P), oxidation of free cysteines, deamidation (e.g. NG) or isomerization (e.g. DG). If present in the CDR regions, those motifs are ideally removed by site-directed mutagenesis in order to increase product homogeneity.

The process of affinity maturation is well described in the art. Among many display systems, phage display (Smith G P (1985) Science 228:1315-1317) and display on eukaryotic cells such as yeast (Boder E T and Wittrup K D (1997) Nature Biotechnology 15: 553-557) seem to be the most commonly applied systems to select for antibody-antigen interaction. Advantages of those display systems are that they are suitable for a wide range of antigens and that the selection stringency can be easily adjusted. In phage display, scFv or Fab fragments can be displayed and in yeast display full-length IgG in addition. Those commonly applied methods allow selection of a desired antibody variants from larger libraries with diversities of more than 10E7. Libraries with smaller diversity, e.g. 10E3, may be screen by microexpression and ELISA.

Non-targeted or random antibody variant libraries can be generated for example by error-prone PCR (Cadwell R C and Joyce G F (1994) Mutagenic PCR. PCR Methods Appl. 3: S136-S140) and provide a very simple, but sometimes limited approach. Another strategy is the CDR directed diversification of an antibody candidate. One or more positions in one or more CDRs can be targeted specifically using for example degenerated oligos (Thompson J et al. (1996) J. Mol. Biol. 256: 77-88) trinucloetide mutagenesis (TRIM) (Kayushin A L et al. (1996) Nucleic Acids Res. 24: 3748-3755) or any other approach known to the art.

Accordingly, in another embodiment, the present disclosure provides isolated β-klotho-binding antibodies, or antigen-binding fragments thereof, consisting of a heavy chain variable region having a VH CDR1 region consisting of an amino acid sequence selected from the group having SEQ ID NOs: 6 and 9 or an amino acid sequence having one, two, three, four or five amino acid substitutions, deletions or additions as compared to SEQ ID NOs: 6 and 9; a VH CDR2 region having an amino acid sequence of SEQ ID NO: 7 or an amino acid sequence having one, two, three, four or five amino acid substitutions, deletions or additions as compared to SEQ ID NO: 7; a VH CDR3 region having an amino acid sequence of SEQ ID NO: 8, or an amino acid sequence having one, two, three, four or five amino acid substitutions, deletions or additions as compared to SEQ ID NO: 8; a VL CDR1 region having an amino acid sequence selected from the group consisting of SEQ ID NOs: 19 or 31, or an amino acid sequence having one, two, three, four or five amino acid substitutions, deletions or additions as compared to SEQ ID NOs: 19 or 31; a VL CDR2 region having an amino acid sequence of SEQ ID NO: 20, or an amino acid sequence having one, two, three, four or five amino acid substitutions, deletions or additions as compared to SEQ ID NO: 20; and a VL CDR3 region having an amino acid sequence of SEQ ID NO: 21, or an amino acid sequence having one, two, three, four or five amino acid substitutions, deletions or additions as compared to SEQ ID NO: 21.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to β-klotho. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the present disclosure pertains to generating non-immunoglobulin based antibodies using non-immunoglobulin scaffolds onto which CDRs of the present disclosure can be grafted. Known or future non-immunoglobulin frameworks and scaffolds may be employed, as long as they comprise a binding region specific for the target β-klotho protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen-binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the present disclosure using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012).

Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The present disclosure provides fully human antibodies that specifically bind to a β-klotho protein. In certain aspects, compared to the chimeric or humanized antibodies, the human β-klotho-binding antibodies of the present disclosure have further reduced antigenicity when administered to human subjects.

Camelid Antibodies

Antibody proteins obtained from members of the camel and dromedary (*Camelus bactrianus* and *Calelus dromaderius*) family including new world members such as llama species (*Lama paccos*, *Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present disclosure is a camelid antibody or nanobody having specific affinity for β-klotho (e.g., human β-klotho). In certain embodiments herein, the camelid antibody or nanobody is naturally produced in the camelid animal, i.e., is produced by the camelid following immunization with β-klotho or a peptide fragment thereof, using techniques described herein for other antibodies. Alternatively, the β-klotho-binding camelid nanobody is engineered, i.e., produced by selection for example from a library of phage displaying appropriately mutagenized camelid nanobody proteins using panning procedures with β-klotho as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the present disclosure into nanobody or single domain antibody framework sequences, as described for example in PCT/EP93/02214.

Bispecific Molecules and Multivalent Antibodies

In another aspect, the present disclosure features bispecific or multispecific molecules comprising a β-klotho-binding antibody, or a fragment thereof, of the present disclosure, for example, antibody NOV005 or NOV006. An antibody of the present disclosure, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the present disclosure may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the present disclosure, an antibody of the present disclosure can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for β-klotho and a second binding specificity for a second target epitope. For example, the second target epitope is another epitope of β-klotho different from the first target epitope.

Additionally, for the present disclosure in which the bispecific molecule is multi-specific, the molecule can further include a third binding specificity, in addition to the first and second target epitope.

In one aspect, the bispecific molecules of the present disclosure comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen-binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules of the present disclosure are murine, chimeric and humanized monoclonal antibodies.

Bispecific molecules can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78,118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand×Fab fusion protein. A bispecific molecule of the present disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present disclosure provides multivalent compounds comprising at least two identical or different antigen-binding portions of the antibodies of the present disclosure binding to β-klotho. The antigen-binding portions can be linked together via protein fusion or covalent or non covalent linkage. Alternatively, methods of linkage have been described for the bispecfic molecules. Tetravalent compounds can be obtained for example by cross-linking antibodies of the antibodies of the present disclosure with an antibody that binds to the constant regions of the antibodies of the present disclosure, for example the Fc or hinge region.

Trimerizing domain are described for example in Borean patent EP 1 012 280B1. Pentamerizing modules are described for example in PCT/EP97/05897.

Antibodies with Extended Half Life

The present disclosure provides for antibodies (e.g., NOV005 or NOV006) that specifically bind to β-klotho protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dendritic cells). A variety of strategies can be used to extend the half life of the antibodies of the present disclosure. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the present disclosure. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialyion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body.

It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin (e.g., human serum albumin; HSA) in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622. In addition, in the context of a bispecific antibody as described above, the specificities of the antibody can be designed such that one binding domain of the antibody binds to FGF21 while a second binding domain of the antibody binds to serum albumin, preferably HSA.

The strategies for increasing half life is especially useful in nanobodies, fibronectin-based binders, and other antibodies or proteins for which increased in vivo half life is desired.

Antibody Conjugates

The present disclosure provides antibodies or fragments thereof that specifically bind to a β-klotho protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the present disclosure provides fusion proteins comprising an antigen-binding fragment (e.g., a Fab fragment, Fd fragment, Fv fragment, F(ab)2 fragment, a VH domain, a VH CDR, a VL domain or a VL CDR) of an antibody described herein, for example, NOV005 or NOV006, and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the present disclosure or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a β-klotho protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide (SEQ ID NO: 64), such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine (SEQ ID NO: 64) provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present disclosure or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidinlbiotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and noradioactive paramagnetic metal ions.

The present disclosure further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alph-emiters such as 213Bi or macrocyclic chelators useful for conjugating radiometal ions, including but not limited to, 131In, 131LU, 131Y, 131Ho, 131Sm, to polypeptides. In certain embodiments, the macrocyclic chelator is 1,4,7,10-tetraazacyclododecane-N,N',N",N'"-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc, 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies

Nucleic Acids Encoding the Antibodies The present disclosure provides substantially purified nucleic acid molecules which encode polypeptides comprising segments or domains of the β-klotho-binding antibody chains described above. Some of the nucleic acids of the present disclosure comprise the nucleotide sequence encoding the heavy chain variable region shown in SEQ ID NO: 15, and/or the nucleotide sequence encoding the light chain variable region shown in SEQ ID NO: 26 or 32. In a specific aspect, nucleic acid molecules provided herein are those identified in Table 1, for example, nucleic acid molecules comprising the sequence of SEQ ID NO: 16, 36, or 38 encoding a VH, or nucleic acid molecules comprising the sequence of SEQ ID NO: 27, 54, 33 or 40 encoding a VL. Some other nucleic acid molecules of the present disclosure comprise nucleotide sequences that are substantially identical (e.g., at least 65, 80%, 95%, or 99%) to the nucleotide sequences of those identified in Table 1, for example, nucleic acid molecules comprising the sequence of SEQ ID NO: 16, 36, or 38 encoding a VH, or nucleic acid molecules comprising the sequence of SEQ ID NO: 27, 54, 33 or 40 encoding a VL. When expressed from appropriate expression vectors, polypeptides encoded by these polynucleotides are capable of exhibiting FGF21 antigen-binding capacity.

Also provided in the present disclosure are polynucleotides which encode all or substantially all of the variable region sequence of a heavy chain and/or a light chain of the β-klotho-binding antibody set forth herein, for example, those set forth in Table 1. In specific aspects, the present disclosure provides polynucleotides which encode all or substantially all of the VH and/or VL of a β-klotho-binding antibody NOV005. In specific aspects, the present disclosure provides polynucleotides which encode all or substantially all of the heavy chain and/or light chain of a β-klotho-binding antibody NOV005. In specific aspects, the present disclosure provides polynucleotides which encode all or substantially all of the VH and/or VL of a β-klotho-binding antibody NOV006. In specific aspects, the present disclosure provides polynucleotides which encode all or substantially all of the heavy chain and/or light chain of a β-klotho-binding antibody NOV006.

Because of the degeneracy of the code, a variety of nucleic acid sequences will encode each of the immunoglobulin amino acid sequences. For example, SEQ ID NOs: 16 and 36 are two nucleic acid sequences which encode for a VH of NOV005 and SEQ ID NOs: 27 and 54 are two nucleic acid sequences which encode for a VL of NOV005.

The nucleic acid molecules of the present disclosure can encode both a variable region and a constant region of the antibody. Some of nucleic acid sequences of the present disclosure comprise nucleotides encoding a heavy chain sequence that is substantially identical (e.g., at least 80%, 90%, or 99%) to the heavy chain sequence set forth in SEQ ID NO: 17. Some other nucleic acid sequences comprising nucleotide encoding a light chain sequence that is substantially identical (e.g., at least 80%, 90%, or 99%) to the light chain sequence set forth in SEQ ID NO: 28 or 34. In a specific aspects, nucleic acid molecules provided herein are those identified in Table 1, for example, nucleic acid molecules comprising the sequence of SEQ ID NO: 18, 37, 30, or 39 encoding a heavy chain, or nucleic acid molecules comprising the sequence of SEQ ID NO: 29, 51, 35, or 41 encoding a light chain.

In a specific aspect, provided herein is a polynucleotide comprising the nucleic acid sequence of SEQ ID NO: 16 encoding a VH. In a specific aspect, provided herein is a polynucleotide comprising the nucleic acid sequence of SEQ ID NO: 36 encoding a VH. In a specific aspect, provided herein is a polynucleotide comprising the nucleic acid sequence of SEQ ID NO: 38 encoding a VH. In a specific aspect, provided herein is a polynucleotide comprising the nucleic acid sequence of SEQ ID NO: 27 encoding a VL. In a specific aspect, provided herein is a polynucleotide comprising the nucleic acid sequence of SEQ ID NO: 54 encoding a VL. In a specific aspect, provided herein is a polynucleotide comprising the nucleic acid sequence of SEQ ID NO: 29 encoding a VL. In a specific aspect, provided herein is a polynucleotide comprising the nucleic acid sequence of SEQ ID NO: 51 encoding a VL.

In a specific aspect, provided herein is a polynucleotide comprising the nucleic acid sequence of SEQ ID NO: 18 encoding a heavy chain. In a specific aspect, provided herein is a polynucleotide comprising the nucleic acid sequence of SEQ ID NO: 37 encoding a heavy chain. In a specific aspect, provided herein is a polynucleotide comprising the nucleic acid sequence of SEQ ID NO: 30 encoding a heavy chain. In a specific aspect, provided herein is a polynucleotide comprising the nucleic acid sequence of SEQ ID NO: 39 encoding a heavy chain.

In a specific aspect, provided herein is a polynucleotide comprising the nucleic acid sequence of SEQ ID NO: 29 encoding a light chain. In a specific aspect, provided herein is a polynucleotide comprising the nucleic acid sequence of SEQ ID NO: 51 encoding a light chain. In a specific aspect, provided herein is a polynucleotide comprising the nucleic acid sequence of SEQ ID NO: 35 encoding a light chain. In a specific aspect, provided herein is a polynucleotide comprising the nucleic acid sequence of SEQ ID NO: 41 encoding a light chain.

The polynucleotide sequences can be produced by de novo solid-phase DNA synthesis or by PCR mutagenesis of an existing sequence (e.g., sequences as described in the Examples below) encoding a β-klotho-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the present disclosure are expression vectors and host cells for producing the β-klotho-binding antibodies described herein, e.g., NOV005 or NOV006. Various expression vectors can be employed to express the polynucleotides encoding the β-klotho-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the FGF21-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a β-klotho-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a β-klotho-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted FGF21-binding antibody sequences. More often, the inserted β-klotho-binding antibody sequences are linked to a signal sequences before inclusion in the vector. Vectors to be used to receive sequences encoding β-klotho-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the β-klotho-binding antibody chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express FGF21-binding polypeptides of the present disclosure. Insect cells in combination with baculovirus vectors can also be used.

In some preferred embodiments, mammalian host cells are used to express and produce the β-klotho-binding polypeptides of the present disclosure. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express β-klotho-binding antibody chains or binding fragments can be prepared using expression vectors of the present disclosure which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Generation of Monoclonal Antibodies

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

Animal systems for preparing hybridomas include the murine, rat and rabbit systems. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies of the present disclosure are human monoclonal antibodies. Such human monoclonal antibodies directed against β-klotho can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N. Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et at., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the present disclosure can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise β-klotho-binding antibodies of the present disclosure. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise β-klotho-binding antibodies of the present disclosure. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise FGF21-binding antibodies of the present disclosure.

Human monoclonal antibodies of the present disclosure can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the present disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Framework or Fc Engineering

Engineered antibodies of the present disclosure include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the present disclosure.

Another type of framework modification involves mutating one or more residues within the framework region, or even within one or more CDR regions, to remove T cell— epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the present disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the present disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present disclosure to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the β-klotho-binding antibodies having VH and VL sequences or full length heavy and light chain sequences shown herein can be used to create new β-klotho-binding antibodies by modifying full length heavy chain and/or light chain sequences, VH and/or VL sequences, or the constant region(s) attached thereto. Thus, in another aspect of the present disclosure, the structural features of a β-klotho-binding antibody of the present disclosure are used to create structurally related β-klotho-binding antibodies that retain at least one functional property of the antibodies of the present disclosure, such as binding to human β-klotho and also activating one or more functional properties of the FGF21-receptor complex (e.g., activating FGF21-receptor signaling).

For example, one or more CDR regions of the antibodies of the present disclosure, or mutations thereof, can be combined recombinantly with known framework regions and/or other CDRs to create additional, recombinantly-engineered, β-klotho-binding antibodies of the present disclosure, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the present disclosure provides a method for preparing a β-klotho-binding antibody (e.g., NOV005 or NOV006) comprising of a heavy chain variable region antibody sequence having a CDR1 sequence of SEQ ID NO: 6 or 9, a CDR2 sequence of SEQ ID NO: 7, and/or a CDR3 sequence of SEQ ID NO: 8; and a light chain variable region antibody sequence having a CDR1 sequence of SEQ ID NO: 19 or 31, a CDR2 sequence of SEQ ID NO: 20, and/or a CDR3 sequence of SEQ ID NO: 21; optionally, altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the present disclosure provides a method for preparing a β-klotho-binding antibody optimized for expression in a mammalian cell consisting of: a full length heavy chain antibody sequence comprising a sequence of SEQ ID NO: 17; and a full length light chain antibody sequence comprising a sequence of SEQ ID NO: 28 or 34; optionally, altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US2005/0255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the β-klotho-binding antibodies described herein, which functional properties include, but are not limited to, specifically binding to human, cynomolgus, rat, and/or mouse β-klotho; and the antibody activates FGF21-mediated signaling, e.g., FGF21-receptor-dependent signaling, in a FGFR1c_β-klotho_HEK293 pERK cell assay.

In certain embodiments of the methods of engineering antibodies of the present disclosure, mutations can be introduced randomly or selectively along all or part of a β-klotho-binding antibody coding sequence and the resulting modified β-klotho-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies. In certain embodiments of the present disclosure antibodies have been engineered to remove sites of deamidation. Deamidation is known to cause structural and functional changes in a peptide or protein. Deamindation can result in decreased bioactivity, as well as alterations in pharmacokinetics and antigenicity of the protein pharmaceutical. (Anal Chem. 2005 Mar. 1; 77(5):1432-9).

In certain embodiments of the present disclosure the antibodies have been engineered to increase pI and improve their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the anti-β-klotho antibodies, or Fabs, of the present disclosure improved their solubility, enabling the antibodies to be formulated at higher concentrations (>100 mg/ml). Formulation of the antibodies at high concentrations (e.g. >100 mg/ml) offers the advantage of being able to administer higher doses of the antibodies into eyes of patients via intravitreal injections, which in turn may enable reduced dosing frequency, a significant advantage for treatment of chronic diseases including cardiovascular disorders. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pI resulting in longer shelf-life and bioactivity in vivo. Preferably, the pI is greater than or equal to 8.2.

The functional properties of the altered antibodies can be assessed using standard assays available in the art and/or described herein, such as those set forth in the Examples (e.g., ELISAs).

Prophylactic and Therapeutic Uses

Antibodies that bind β-klotho as described herein (e.g., NOV005 or NOV006) and antigen-binding fragments thereof, can be used at a therapeutically useful concentration for the treatment of a disease or disorder associated with aberrant FGF21 signaling (e.g., aberrant activation of FGF21-mediated signaling and/or FGF21 receptor signaling), by administering to a subject in need thereof an effective amount of the antibodies or antigen-binding fragments of the present disclosure, e.g., NOV005 or NOV006. The present disclosure provides a method of treating FGF21-associated metabolic disorders by administering to a subject in need thereof an effective amount of the antibodies of the present disclosure, e.g., NOV005 or NOV006. The present disclosure provides a method of treating FGF21-associated cardiovascular disorders by administering to a subject in need thereof an effective amount of the antibodies of the present disclosure, e.g., NOV005 or NOV006.

The antibodies of the present disclosure (e.g., NOV005 or NOV006) can be used, inter alia, to prevent treat, prevent, and improve FGF21 associated conditions or disorders, including but not limited to metabolic, endocrine, and cardiovascular disorders, such as obesity, type 1 and type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, hypertriglyceridemia, metabolic syndrome, acute myocardial infarction, hypertension, cardiovascular disease, atherosclerosis, peripheral arterial disease, stroke, heart failure, coronary heart disease, kidney disease, diabetic complications, neuropathy, gastroparesis, disorders associated with severe inactivating mutations in the insulin receptor, and other metabolic disorders, and in reducing the mortality and morbidity of critically ill patients.

The antibodies of the present disclosure (e.g., NOV005 or NOV006) can be used, inter alia, to treat, diagnose, ameliorate, improve, or prevent a number of diseases, disorders, or conditions, including, but not limited to metabolic diseases associated with insulin resistance, such as type 2 diabetes mellitus, type 1 diabetes mellitus, insulin receptor mutation disorders (INSR disorders, e.g., Type B insulin resistance), nonalcoholic fatty liver disease (NAFLD) and various forms of partial lipodystrophy including familial partial lipodystrophy and HIV-highly active antiretroviral therapy (HIV-HAART) induced partial lipodystrophy as well as diseases associated with insulin production (e.g., type 1 diabetes mellitus), and in reducing the mortality and morbidity of critically ill patients.

Multiple inactivating mutations of the INSR have been described with varying phenotypes. Patients typically present with severe resistance to the action of insulin which advances to hyperglycemia at the time of puberty. The current standard of care is treatment with very high doses of insulin when subjects become hyperglycemic, which typically is inadequate in controlling hyperglycemia.

In particular aspects, the antibodies of the present disclosure (e.g., NOV005 or NOV006) can be used, inter alia, to treat or manage type 1 diabetes mellitus, dyslipidemial, hyperglycemia, hypoglycemia, glucose intolerance, hypertriglyceridemia, or HIV-HAART Induced Partial Lipodystrophy.

The antibodies of the present disclosure can also be used in combination with other agents for the prevention, treatment, or improvement of FGF21 associated disorders. For example, statin therapies may be used in combination with the FGF21 mimetic antibodies and antigen-binding fragments of the present disclosure for the treatment of patients with cardiovascular or metabolic disorders.

In particular aspects, provided herein is a method of reducing body weight (e.g., by at least 4%, at least 5%, at least 6%, at least 7%, at least 8%, at least 9%, at least 10%, at least 12%, at least 15%, or at least 20%) in a subject, comprising administering to a subject in need thereof an effective amount of a pharmaceutical composition comprising an antibody or antigen-binding fragment described herein (e.g., NOV005 or NOV006) which binds β-klotho and is capable of increasing the activity of β-klotho/FGFR1c receptor complex.

In particular aspects, provided herein is a method of reducing appetite or food intake (e.g., by at least 4%, at least 5%, at least 6%, at least 7%, at least 8%, at least 9%, at least 10%, at least 12%, at least 15%, or at least 20%) in a subject, comprising administering to a subject in need thereof an effective amount of a pharmaceutical composition comprising an antibody or antigen-binding fragment described herein (e.g., NOV005 or NOV006) which binds β-klotho and is capable of increasing the activity of β-klotho/FGFR1c receptor complex.

In particular aspects, provided herein is a method of reducing (e.g., by at least 4%, at least 5%, at least 6%, at least 7%, at least 8%, at least 9%, at least 10%, at least 12%, at least 15%, at least 20%, at least 30%, at least 40%, at least 50%, at least 60%, at least 70%, at least 80%, or at least 90%) plasma triglyceride (TG) concentrations or plasma total cholesterol (TC) concentrations in a subject, comprising administering to a subject in need thereof an effective amount of a pharmaceutical composition comprising an antibody or antigen-binding fragment described herein (e.g., NOV005 or NOV006) which binds β-klotho and is capable of increasing the activity of β-klotho/FGFR1c receptor complex.

In specific aspects of the methods provided herein, the subject is afflicted with a metabolic disorder, such as obesity, type 1 and type 2 diabetes mellitus, pancreatitis, dyslipidemia, nonalcoholic steatohepatitis (NASH), insulin resistance, hyperinsulinemia, glucose intolerance, hyperglycemia, hypertriglyceridemia, and metabolic syndrome. In specific aspects of the methods provided herein, the subject is afflicted with a cardiovascular disorder. In particular aspects, the subject is a human.

In certain aspects, provided herein is a method of treating or managing obesity in a subject, comprising administering to a subject in need thereof an effective amount of a pharmaceutical composition comprising an antibody or antigen-binding fragment described herein (e.g., NOV005 or NOV006) which binds β-klotho and is capable of increasing the activity of β-klotho/FGFR1c receptor complex.

In certain aspects, provided herein is a method of treating or managing type 2 diabetes in a subject, comprising administering to a subject in need thereof an effective amount of a pharmaceutical composition comprising an antibody or antigen-binding fragment described herein (e.g., NOV005 or NOV006) which binds β-klotho and is capable of increasing the activity of β-klotho/FGFR1c receptor complex.

In certain aspects, provided herein is a method of treating or managing type 1 diabetes in a subject, comprising administering to a subject in need thereof an effective amount of a pharmaceutical composition comprising an antibody or antigen-binding fragment described herein (e.g., NOV005 or NOV006) which binds β-klotho and is capable of increasing the activity of β-klotho/FGFR1c receptor complex.

In certain aspects, provided herein is a method of treating or managing lipodystropy, such as HIV-HAART induced partial lipodystrophy, in a subject, comprising administering to a subject in need thereof an effective amount of a pharmaceutical composition comprising an antibody or antigen-binding fragment described herein (e.g., NOV005 or NOV006) which binds β-klotho and is capable of increasing the activity of β-klotho/FGFR1c receptor complex.

In certain aspects, provided herein is a method of treating or managing NASH in a subject, comprising administering to a subject in need thereof an effective amount of a pharmaceutical composition comprising an antibody or antigen-binding fragment described herein (e.g., NOV005 or NOV006) which binds β-klotho and is capable of increasing the activity of β-klotho/FGFR1c receptor complex.

In certain aspects, provided herein is a method of treating or managing an insulin receptor mutation disorder in a subject, comprising administering to a subject in need thereof an effective amount of a pharmaceutical composition comprising an antibody or antigen-binding fragment described herein (e.g., NOV005 or NOV006) which binds β-klotho and is capable of increasing the activity of β-klotho/FGFR1c receptor complex.

Pharmaceutical Compositions

The present disclosure provides pharmaceutical compositions comprising the β-klotho-binding antibodies (intact or binding fragments) formulated together with a pharmaceutically acceptable carrier. The compositions can additionally contain one or more other therapeutic agents that are suitable for treating or preventing, for example, cardiovascular disorders. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present disclosure can be administered by a variety of methods known in the art. The route and/or mode of administration vary depending upon the desired results. It is preferred that administration be intravitreal, intravenous, intramuscular, intraperitoneal, or subcutaneous, or administered proximal to the site of the target. The pharmaceutically acceptable carrier should be suitable for intravitreal, intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound. In a specific aspect, a pharmaceutical composition comprising a β-klotho-binding antibody described herein, such as antibody NOV005 or NOV006, for use in the methods provided herein, is administered subcutaneously. In a specific aspect, a pharmaceutical composition comprising a β-klotho-binding antibody described herein, such as antibody NOV005 or NOV006, for use in the methods provided herein, is administered intravenously.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the present disclosure can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the β-klotho-binding antibody is employed in the pharmaceutical compositions of the present disclosure. The β-klotho-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being toxic to the patient. The selected dosage level depends upon a variety of factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the present disclosure employed in the pharmaceutical composition at levels lower than that required to achieve the desired therapeutic effect and gradually increase the dosage until the desired effect is achieved. In general, effective doses of the compositions of the present disclosure, for the treatment of a cardiovascular disorders described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. In a particular embodiment, for systemic administration with an antibody, the dosage ranges from about 0.0001 to 100 mg/kg, or from 0.01 to 15 mg/kg, of the host body weight. An exemplary treatment regime entails systemic administration once per every two weeks or once a month or once every 3 to 6 months. An exemplary treatment regime entails systemic administration once per every two weeks or once a month or once every 3 to 6 months, or as needed (PRN).

Antibody is usually administered on multiple occasions. Intervals between single dosages can be weekly, monthly or yearly. Intervals can also be irregular as indicated by measuring blood levels of β-klotho-binding antibody in the patient. In addition alternative dosing intervals can be determined by a physician and administered monthly or as necessary to be efficacious. In some methods of systemic administration, dosage is adjusted to achieve a plasma antibody concentration of 1-1000 μg/ml and in some methods 25-500 μg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the invention but not to limit its scope. Other variants of the invention will be readily apparent to one of ordinary skill in the art and are encompassed by the appended claims.

Example 1: Antibody Screening and Production

Preparation of Human FGFR1c β-Klotho 300.19 Cells for Use as an Antigen 300.19 cells which stably expressed the human FGFR1c (1-386 aa) and β-klotho were generated for use as a whole cell antigen. The full-length cDNA encoding human β-klotho (GenBank Accession number NM_175737) was cloned into the EcoRI and EcoRV sites of pEF1/Myc-His B (Invitrogen Cat. #V92120). The cDNA encoding amino acids 1-386 of human FGFR1c (GenBank Accession number NM_023106) was cloned into the BarnHI and NotI sites of pEF6/Myc-His B (Invitrogen, Cat. number V96220). In both constructs a Kozak sequence (CACC) was included immediately before the start codon and a stop codon was added before the Myc-His tag in the vector. Murine pre-B 300-19 cells were co-transfected with β-klotho and FGFR1c plasmids by electroporation using the Amaxa Nucleofector device and Nucleofector kit (Lonza, Cat #VCA-1003). Stable clones were selected using 1 mg/ml Geneticin (Invitrogen, Cat #10131) and 8 µg/ml Blasticidin (Invitrogen, Cat #46-1120) for 3 weeks.

Preparation of FGFR/β-Klotho-Expressing HEK293 Cells for Use in Cell Assays

To test the binding specificity, functional activity, or ortholog cross-reactivity of β-klotho antibodies, HEK293 cells stably expressing human FGFR1c_β-klotho, human FGFR2c_β-klotho, human FGFR3c_β-klotho, human FGFR4_β-klotho, or cynomolgus monkey FGFR1c_β-klotho were generated using standard Lipofectamine 2000 transfection and cell clone selection methods.

The following mammalian expression plasmids encoding full-length human β-klotho (NM_175737), human FGFR1c (NM_023106), human FGFR2c (NP_001138387), human FGFR3c (NP_000133), or human FGFR4 (NP_998812) cDNAs were used: for cynomolgus monkey β-klotho, the full-length sequence was PCR amplified from cynomolgus monkey adipose tissue cDNA (BioChain, Cat. #C1534003-Cy) with primers based on the human and rhesus monkey β-klotho sequences, and cloned. The cynomolgus monkey FGFR1c cDNA was cloned from cynomolgus monkey adipose tissue cDNA (BioChain, Cat. #C1534003-Cy) using primers based on the human FGFR1c sequence (#NM_023106) and was shown to be 100% identical at the amino acid level to human FGFR1c. Hence, the human FGFR1c cDNA construct described above was used to make HEK293 cells which stably expressed cynomolgus monkey β-klotho and human FGFR1c (#NM_023106) since the human and cynomolgus monkey FGFR1c amino acid sequences are identical.

Determining the Binding Affinity of Antibodies to β-Klotho

Binding affinities of antibodies were determined using Biacore kinetic analysis. A Series S Sensor Chip CM5 (GE Healthcare, Cat. No. BR-1005-30) was equilibrated to ambient temperature for approximately 30 minutes The system was primed with 1× HBS-EP+ buffer (10× soln, GE Healthcare, Cat. No. BR-1006-69) and the chip was loaded into the Biacore instrument. The chip was normalized using BIAnormalizing (GE Healthcare, Cat. No. BR-1006-51) solution and the chip was conditioned with 50 mM NaOH using a flow rate of 60 µL/minute for all flow paths. The 30 second injection was repeated three times with a wait time of 60 seconds. 10 mM sodium acetate pH 5.0 was injected at 60 µL/minute for 120 seconds and repeated twice. After a new cycle was started for immobilizing the anti-human IgG Fc using the Human Antibody Capture Kit (GE Healthcare, Cat. No. BR-1008-39). The anti-human Fc Ab was diluted to 50 µg/mL in immobilization buffer (10 mM sodium acetate pH 5.0). The amine coupling reagents were mixed 1:1 (EDC and NHS) and injected for 7 minutes at 10 µL/minute. Then anti-human Fc Ab was injected for 6 minutes at 10 µL/minute. Lastly ethanolamine was injected for 7 minutes at 10 µL/minute with a wait time of 60 seconds. This should result in immobilization of approximately 8000-10000 RU. Then we performed test injections for an Rmax of 10 RUs (capture levels=~28 RUs) for NOV004, NOV005 and NOV006. This was done using a flow rate of 10 uL/mL and a 3 M MgCl$_2$ regeneration buffer. Each flow cell was evaluated each time due to changes in chip surface, affinity of IgGs, IgG protein quality and differences in dilutions. We started with an IgG concentration of 0.5 ug/mL and increased (or decreased) the concentration depending on the results from the sample injections. For example, if 100 RU was observed in 15 seconds, then we diluted the Ab solution to 0.25 ug/mL and repeated the injections. After capturing parameters were determined for each antibody in each flow cell, human β-klotho at various concentrations was passed over the chip and ka (1/Ms), kd (1/s), KD (M), and Rmax (RU) were calculated by Biacore kinetics.

Determining if Different Antibodies Bind Competitively to β-Klotho

Forte Bio was used to determine if antibodies competitively bound to human β-klotho. All samples and reagents were diluted in 10× kinetics buffer (Forte Bio cat #18-1092) with PBS buffer with a 1/10 (v/v) ratio. Human β-klotho (R and D Systems 5889-KB-050) was diluted with kinetic buffer to the desired concentration (5 ug/ml). Human β-klotho was loaded onto an anti-his sensor (Forte Bio, cat #18-5114) for 20 seconds, then antibody 1 was loaded for 400 seconds onto the sensor until saturation conditions were reached (200 nM). Lastly the competing antibody was loaded onto the sensor for 100 seconds at 200 nM in the presence of 200 nM antibody 1. The absence of a second binding signal indicates that the antibodies compete for binding to human β-klotho.

Measuring FGFR β-Klotho Receptor Activation Using a pERK Cell Assay

Standard techniques were used for cell culture and to measure phospho-ERK 1/2 (pERK) levels. Briefly, HEK293 cells stably expressing human FGFR1c_β-klotho, human FGFR2c_β-klotho, human FGFR3c_β-klotho, human FGFR4_β-klotho, or cynomolgus monkey FGFR1c_β-klotho were maintained in DMEM medium (Invitrogen, 11995) containing 10% FBS (Hyclone, SH30071), blasticidin (Invitrogen, A1113902), and Geneticin (Invitrogen, 10131035) at 37° C. in 5% CO$_2$. Cells were plated into 384-well poly-D-lysine-coated plates (BD Biosciences, 354663) and incubated overnight at 37° C. in 5% CO$_2$, followed by scrum-starvation.

Hybridoma supernatants or β-klotho antibodies were diluted in Freestyle 293 media and various concentrations of the antibodies were added to the plate. Following incubation, the cells were washed, then lysed with lysis buffer. Cell lysates were transferred to a 384-well assay plate (PerkinElmer, Cat. #6008280) and the AlphaScreen SureFire™ pERK 1/2 Kit (Perkin Elmer, TGRES10K) was used to measure phospho-ERK 1/2 levels. Plates were read on the EnVision 2104 multi-label reader (Perkin Elmer) using standard AlphaScreen settings. Dose-response data was graphed as pERK activity fold over basal versus protein concentration to determine $EC_{50}$ values using the equation $Y=Bottom+(Top-Bottom)/(1+10^{\wedge}((Log\ EC_{50}-X)\times Hill-Slope))$ and GraphPad Prism 5 Software.

Preparation of Monoclonal Antibodies

Anti-human-β-klotho antibodies were generated in Balb/c (Jackson Laboratory strain: BALB/cJ) or Bcl2 22 wehi (Jackson Laboratory strain: C.Cg-Tg(BCL2)22Wehi/J) mice by whole cell immunizations essentially as described in Dreyer et al (2010) (Dreyer A M et. al. (2010) BMC Biotechnology 10:87).

Briefly, $1\times10^7$ human FGFR1c_β-klotho_300.19 cells were injected into Balb/c mice six times at 10 to 30 day intervals. The first whole cell injections were done with Freund's Complete Adjuvant (Sigma-Aldrich F5881). Cells and adjuvant were not mixed, but injected separately in two close, but distinct subcutaneous sites. These were followed later by intraperitoneal injections of the same cells with either Sigma Adjuvant System (Sigma-Aldrich 56322) or without adjuvant.

Using Bcl2 22 wehi mice, $1\times10^7$ human FGFR1c_β-klotho_300.19 cells were injected into these animals four times at seven day intervals. The first injections were done with Freund's Complete Adjuvant (Sigma-Aldrich F5881). Cells and adjuvant were injected separately in two sets of two close, but distinct subcutaneous sites Subsequent injections of cells were done subcutaneously without adjuvant.

Immune responses in the immunized mice were measured by a fluorescence-activated cell sorting (FACS) assay. Serum from the immunized mice diluted 1,000- or 10,000-fold was used to stain human FGFR1c_β-klotho_HEK and human FGFR1c_β-klotho_300.19 cells, followed by an allophycocyanin (APC) secondary anti-murine IgG detection antibody (Jackson ImmunoResearch Cat #115-136-071). Fluorescence was read on a Becton Dickinson LSRII or Foressa flow cytometer. Four mice with the highest titer were chosen for electrofusions.

Hybridoma Screening, Subcloning, and Selection $2\times10^8$ spleenoctyes and $5\times10^7$ fusion partner FO cells (ATCC, CRL-1646) were washed in Cytofusion Medium (LCM-C, Cyto Pulse Sciences) and fused using a Hybrimune Waveform Generator (Cyto Pulse Sciences, model CEEF-50B) according to manufacturer's specification with a peak pulse of 600 volts. Cells were plated into 384 well plates at a calculated density of 3,000 FO cells per well and cultured in HAT selection media (Sigma-Aldrich Cat. H0262).

The primary screen was performed using a high throughput FACS platform (Anderson, Paul. Automated Hybridoma Screening, Expansion, Archiving and Antibody Purification. In: 3rd Annual 2014 SLAS Conference. Jan. 18-22, 2014, San Diego, Calif.). Briefly, hybridoma supernatants were incubated with human FGFR1c_β-klotho stably expressing and non-expressing cell lines and antibody binding was determined with an anti-murine IgG-APC secondary antibody (Jackson ImmunoReseach Cat #115-136-071).

Antibodies from each hybridoma supernatant were tested for binding simultaneously against four barcoded cell lines: 300.19 parental cells, human_FGFR1c_β-klotho_300.19 cells, parental HEK 293 cells, and human FGFR1c-β-klotho_HEK 293 cells. 348 hits were chosen in the primary screen. Primary hits were expanded in 96-well plates and binding was confirmed again on human FGFR1c_β-klotho_HEK 293 cells by FACS, yielding 122 confirmed hits. HAT (hypoxanthine-aminopterin-thymidine) media-containing supernatants of 115 FACS binding reconfirmed hits were profiled for cell activation of the human FGFR1c_β-klotho receptor complex using the phospho-ERK 1/2 assay described herein.

Hybridomas with the highest phospho-ERK 1/2 cell activity in there supernatants were expanded and IgGs were purified from their supernatants. Purified IgGs from 74 hybridomas were profiled for cell activation of the human FGFR1c_β-klotho receptor complex using the phospho-ERK 1/2 assay described in Example 2. IgGs from hybridomas with the best potency for phospho-ERK 1/2 activation of the human FGFR1c_β-klotho receptor complex were profiled for ortholog cross-reactivity to the cynomolgus monkey FGFR1c_β-klotho receptor complex and selectivity for the human FGFR2c_β-klotho and human FGFR3c_β-klotho receptor complexes using the phospho-ERK 1/2 assay described in Example 2. On the basis of these profiling results, a few hybridoma clones, e.g., 127F19, were selected for further profiling. In particular, the most potent, purified IgGs, such as clone 127F19, were profiled for cross-reactivity and shown to activate cynomolgus monkey FGFR1c_β-Klotho; but not human FGFR2c_β-Klotho, FGFR3c_β-Klotho. FGFR4_β-Klotho or Klotho_FGFR. The selected IgGs, for example clone 127F19, bound to 13-Klotho or FGFR1c_β-Klotho expressing cells, and not FGFR1c alone expressing cells.

To evaluate 127F19 signalling in cells expressing α-klotho, HEK293 cells were transfected with α-klotho, Egr1-luciferase and Renilla luciferase. Briefly, HEK293 cells were cultured in DMEM, 10% FBS and plated at 30000 cells/well and transfected with Klotho, Egr-1-luc and TK-Rennila using Lipofectamine 2000. Next day, FGF23, FGF21, and 127F19 were diluted to the indicated concentration in DMEM supplemented with 0.1% FBS and added to transfected cells overnight. Luciferase activities were detected by Dual-Glo luciferase assay kit (Promega, E2920) according to manufacturer's instruction. As expected, FGF23, which requires α-klotho expression for its signaling, showed strong luciferase expression. However, neither FGF21 or 127F19 showed any significant luciferase expression, suggesting that α-klotho does not act as co-receptor for FGF21 or these FGF21 mimetic antibodies.

Humanization and Affinity-Maturation of Monoclonal Antibodies Humanization

The process of humanization is well described in the art (Jones P T et al. (1986) Nature 321: 522-525; Queen C et al. (1989) PNAS USA 86: 10029-10033; Riechmann L et al. (1988) Nature 33:323-327; Verhoeyen M et al. (1988) Science 239: 1534-1536). The term humanization describes the transfer of the antigen-binding site of a non-human antibody, e.g. a murine derived antibody, to a human acceptor framework, e.g. a human germline sequence (Retter I et al. (2005). Nucleic Acids Res. 33:D671-D674).

The main rationale for humanizing an antibody is seen in minimizing the risk of developing an immunogenic response to the antibody in humans (Rebello P R et al. (1999) Transplantation 68: 1417-1420). The antigen-binding site comprises the complementary determining regions (CDRs)

(Chothia C and Lesk A M (1987) Journal of Molecular Biology 196: 901-917; Kabat E et al. (1991) Anon. 5th Edition ed; NIH Publication No. 91: 3242) and positions outside the CDR. i.e. in the framework region of the variable domains (VL and VH) that directly or indirectly affect binding. Framework residues that may directly affect binding can, for example, be found in the so called "outer" loop region located between CDR2 and CDR3. Residues that indirectly affect binding are for example found at so called Vernier Zones (Foote J, Winter G. (1992) Journal of Molecular Biology 224:4 87-499). They are thought to support CDR conformation. Those positions outside the CDRs are taken into account when choosing a suitable acceptor framework to minimize the number of deviations of the final humanized antibody to the human germline acceptor sequence in the framework regions.

Multiple human germline acceptor frameworks were tested for humanization of both light chain and heavy chain. For example, human frameworks VBase_VH4_4-30.1 and VBase_VH3_3-21 were tested for humanization of the heavy chain, and human frameworks VBase_VK1_018 and VBase_VK3_L25 were tested for humanization of the light chain.

Sequence Optimization Affinity Maturation

Certain amino acid sequence motifs are known to undergo post-translational modification (PTM) such as glycosylation (i.e. NxS/T, x any but P), oxidation of free cysteines, deamidation (e.g. NG) or isomerization (e.g. DG). If present in the CDR regions, those motifs are ideally removed by site-directed mutagenesis in order to increase product homogeneity.

The process of affinity maturation is well described in the art. Among many display systems, phage display (Smith G P, 1985, Filamentous fusion phage: novel expression vectors that display cloned antigens on the virion surface. Science 228:1315-1317) and display on eukaryotic cells such as yeast (Boder E T and Wittrup K D, 1997, Yeast surface display for screening combinatorial polypeptide libraries. Nature Biotechnology 15: 553-557) seem to be the most commonly applied systems to select for antibody-antigen interaction. Advantages of those display systems are that they are suitable for a wide range of antigens and that the selection stringency can be easily adjusted. In phage display, scFv or Fab fragments can be displayed and in yeast display full-length IgG in addition. Those commonly applied methods allow selection of a desired antibody variants from larger libraries with diversities of more than 10E7. Libraries with smaller diversity, e.g. 10E3, may be screen by micro-expression and ELISA. Non-targeted or random antibody variant libraries can be generated for example by error-prone PCR (Cadwell R C and Joyce G F, 1994, Mutagenic PCR. PCR Methods Appl. 3: S136-S140) and provide a very simple, but sometimes limited approach. Another strategy is the CDR directed diversification of an antibody candidate. One or more positions in one or more CDRs can be targeted specifically using for example degenerated oligos (Thompson J et al., 1996, Affinity maturation of a high-affinity human monoclonal antibody against the third hypervariable loop of human immunodeficiency virus: use of phage display to improve affinity and broaden strain reactivity. J. Mol. Biol. 256: 77-88) trinucloetide mutagenesis (TRIM) (Kayushin A L et al., 1996, A convenient approach to the synthesis of trinucleotide phosphoramidites—synthons for the generation of oligonucleotide/peptide libraries. Nucleic Acids Res. 24: 3748-3755) or any other approach known to the art. Amino acid modifications were made to humanization candidates to remove PTM.

Generation of Expression Plasmids

DNA sequences coding for humanized VL and VH domains were ordered at GeneArt™ (Life Technologies Inc. Regensburg, Germany) including codon optimization for homosapiens. Sequences coding for VL and VH domains were subcloned by cut and paste from the GeneArt derived vectors into expression vectors suitable for secretion in mammalian cells. The heavy and light chains were cloned into individual expression vectors to allow co-transfection. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and zeocin marker).

Expression and Purification of Humanized Antibody Candidates

Human Embryonic Kidney cells constitutively expressing the SV40 large T antigen (HEK293-T ATCC11268) are one of the commonly used host cell lines for transient expression of humanized and/or optimized IgG proteins. Transfections were performed using PEI (Polyethylenimine, MW 25.000 linear, Polysciences, USA Cat. No. 23966) as transfection reagent.

A first purification was performed by affinity on a HiTrap ProtA MabSelect®SuRe column. The eluate was tested for aggregation (SEC-MALS) and purity (SDS-PAGE, LAL and MS). If needed, pools from the first purification were loaded a SPX (Hi Load 16/60 Superdex 200 grade 120 mL (GE-Helthcare). NOV004, NOV005, and NOV006 are humanized mAbs derived from the mouse hybridoma 127F19. The IgG1 L234A/L235A (LALA) or IgG1κ D265A/P329A (DAPA) isotypes were selected as preventative measures to reduce the antibody's ability to promote antibody-dependent cell-mediated cytotoxicity (ADCC) and complement-dependent cytotoxicity (CDC) (see, e.g., Hezareh M et al. (2001) Journal of Virology 75: 12161-12168). Humanization candidates NOV004, NOV005, and NOV006, which are IgG1 (DAPA) isotypes, were expressed and purified as described.

Example 2: In Vitro Charactionization of Monoclonal Antibodies

Figure 2A:
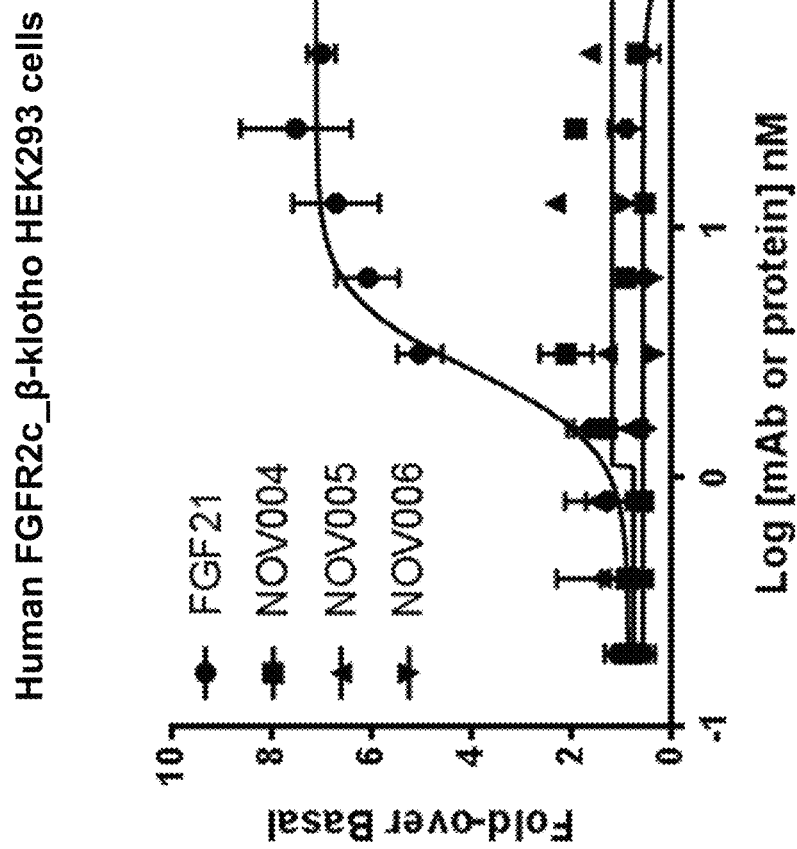
Figure 2B:
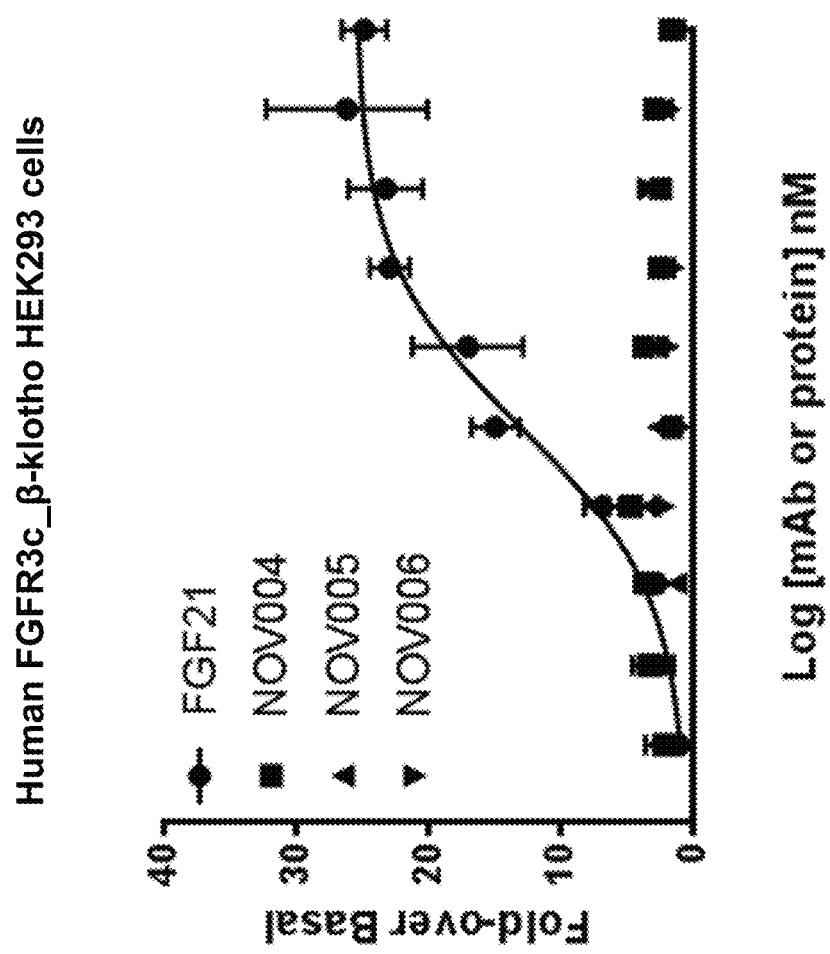
Figure 3:
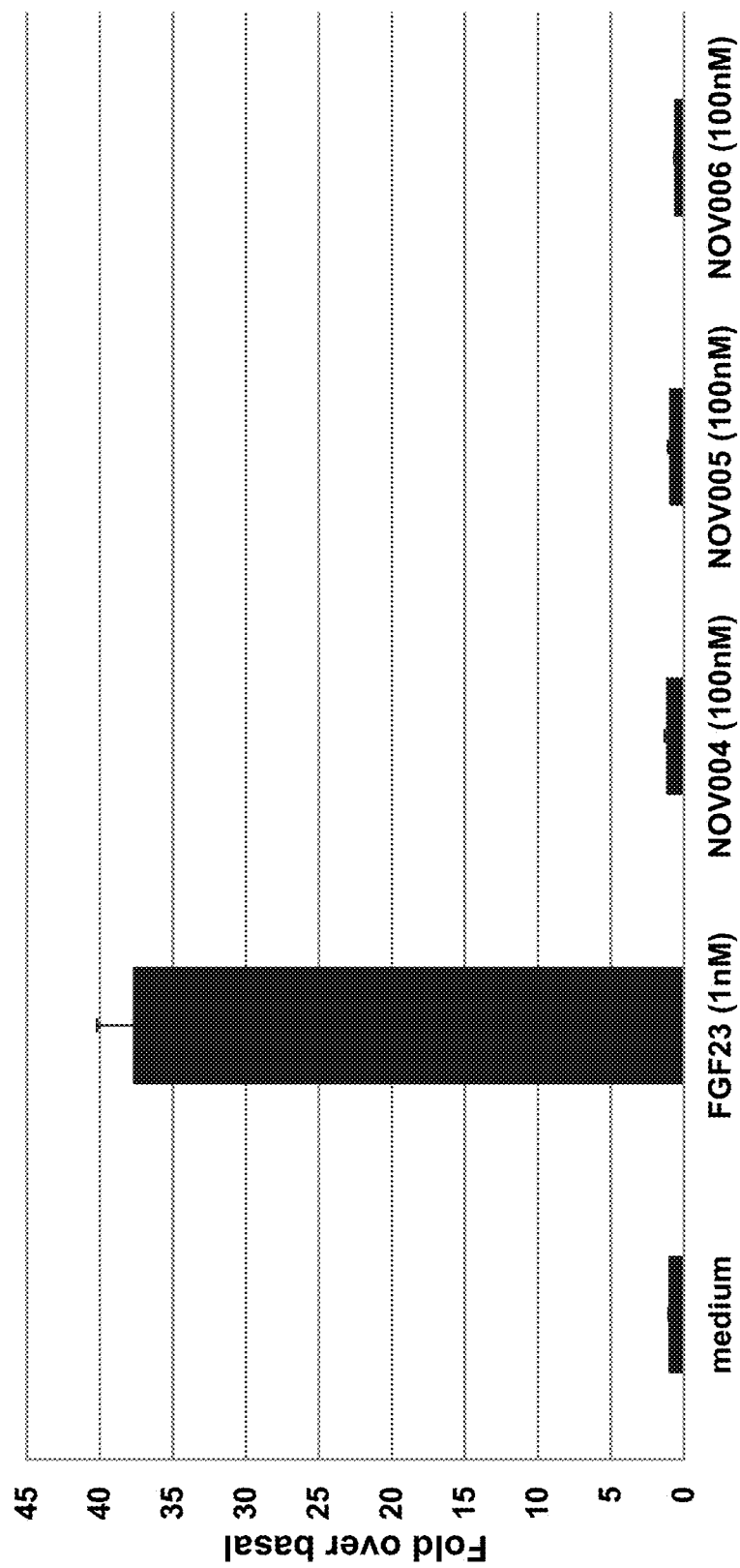
FIG. 3: Profiling of NOV004, NOV005, and NOV006 for FGF23 activity using HEK293 cells transfected with α-klotho, Egr1-luciferase and Renilla luciferase. FGF23 was used as positive control.
Figure 4:
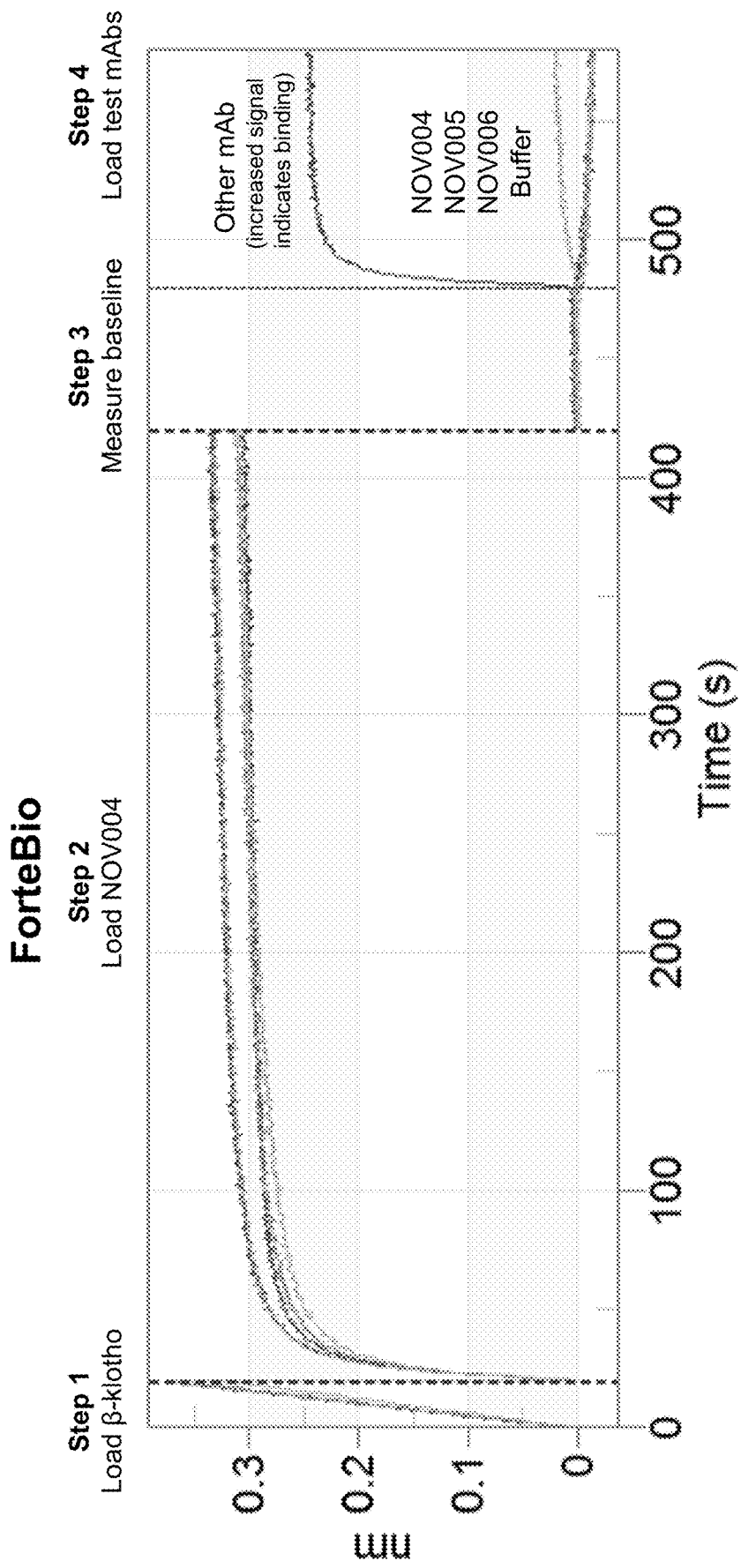
FIG. 4: Competitive binding activity of NOV005 and NOV006 against NOV004 for human β-klotho. Forte Bio® Biosensor system was used to determine competitive binding activity to human β-klotho. In step 1, recombinant human β-klotho was loaded onto the senor, followed by loading of NOV004 until saturation in step 2. Then NOV005 or NOV006 were loaded and competitive binding activity against NOV004 were detected. The absence of a second binding signal indicates that the antibodies compete for binding to human β-klotho. An unrelated antibody was used as a negative control, and NOV004 was used as a positive control for self-competition.

In vitro work was done to show the binding and cell activity properties of NOV004, NOV005, and NOV006. Biacore as described in Example 1 was used to estimate the $K_D$s of the mAbs to human β-klotho. NOV004, NOV005, and NOV006 have $K_D$s calculated to be about 3×E-10M, 3×E-10M, and 4×E-10M, respectively. The pERK assay as described in Example 1 was used to profile mAbs for FGFR_β-klotho receptor activity. NOV004 activated the human and cynomolgus monkey FGFR1c_β-klotho receptor complex with $EC_{50}$s calculated to be about 3 nM and 20 nM, respectively (FIG. 1). NOV005 activated the human and cynomolgus monkey FGFR1c_β-klotho receptor complex with an $EC_{50}$s calculated to be about 3 nM and 16 nM, respectively (FIG. 1). NOV006 activated the human and cynomolgus monkey FGFR1c_β-klotho receptor complex with an $EC_{50}$s calculated to be about 4 nM and 18 nM, respectively (FIG. 1). NOV005, NOV006, and NOV004 did not activate human FGFR2c_β-klotho, FGFR3c_β-klotho, or FGFR4_β-klotho receptor complexes (FIG. 2). The mAbs were profiled for FGF23 activity as described in Example 1. NOV005. NOV006, and NOV004 did not exhibit FGF23 activity (FIG. 3). Forte Bio data shows that NOV005 and NOV006 compete with NOV004 for binding to human β-klotho (FIG. 4).

Epitope mapping studies by hydrogen deuterium exchange of human β-klotho extracellular domain with a version of NOV004 that has a human IgG1-LALA isotype show that the following peptides are significantly protected in the mAb-β-klotho ECD complex: 246-265, 343-349, 421-429, 488-498, 509-524, 536-550, 568-576, 646-669, 773-804, 834-857, and 959-986 aa; and that the following regions are most strongly protected: 246-265, 536-550, 834-857 and 959-986 aa (data not shown; see PCT International Application Publication No. WO 2017/021893, which is hereby incorporated by reference in its entirety). These studies, in combination with the binding, activity and competition data, indicate that NOV005 and NOV006 would also significantly protect such β-klotho ECD regions.

Example 3: Pharmacokinetic Profiles of Monoclonal Antibodies in Rat

Animals and Maintenance Conditions

Animal care and husbandry were provided according to the Guide for the Care and Use of Laboratory Animals (Institute of Laboratory Animal Resources, National Research Council). All procedures were governed by the standards set forth by the US Department of Health and Human Services and performed according to protocol approved by the Novartis Institutes for BioMedical Research (NIBR) Animal Care and Use Committee. Male, Sprague-Dawley rats (n=3/group) were housed in solid-bottom cages on a rack equipped to automatically provide water ad libitum, maintained on a 12 hr light/dark cycle (6 am to 6 pm), and given free access to standard rodent chow (Harlan-Teklad; Frederick, Md.; cat #8604). The vivarium was maintained between 68 and 76° F. with 30 to 70% humidity.
NOV004, NOV005. Or NOV006 Preparation and Dosing Stock solutions of NOV004, NOV005, and NOV006 in 10 mM His/His-HCl, 220 mM sucrose were thawed under refrigeration prior to use. On the morning of dosing, all three antibodies were diluted to approximately 3 mg/mL in PBS and appropriate volumes were drawn into dosing syringes (3 mL/kg) and kept at room temperature until administration. Animals were placed in tube restrainers and administered either NOV004, NOV005, or NOV006 via intravenous (IV) injection into the tail vein (10 mg/kg).
Blood Sample Collection Blood samples were collected on day −3 (Baseline), day 0 (1 and 6 h post-dose), and days 1, 2, 3, 4, 8, 16 and 28 post-dose. All time points were timed from the end of administration of the dose given on day 0. At each timepoint, approximately 70 µl (70 µL) of blood was collected into BD Microtainer collection/separator tubes with EDTA (Becton, Dickinson, and Company; Franklin Lakes, N.J.; cat #365973). Pressure was applied with gauze to stop the bleeding. Samples were centrifuged for 10 min at 20,817×g, and then ~30 µL plasma was transferred to 0.2 mL Thermo-strip tube (Thermo-Scientific; Pittsburgh, Pa.; cat #AB-0451) and frozen at 80° C. Rats were returned to their home cage after each collection.
Measurement of Plasma Total NOV004, NOV005, or NOV006 Concentrations Human IgG (i.e. NOV004, NOV005, or NOV006) in rat plasma was quantified using a custom sandwich immunoassay with a Goat anti-Human Fc-gamma antibody (KPL #109-005-098) as capture antibody and a goat anti-human-IgG with an HRP label as detection antibody. The capture antibody (2 µg/mL in PBS, 30 µL/well) was coated on 384-well, white, microtiter plates (Greiner Bio-One; Monroe, N.C.; cat no. 781074). The plates were incubated overnight at room temperature (RT) without shaking. After aspirating the coating solution without washing, 90 µL of 1× Milk Diluent/Blocking solution (KPL; Gaithersburg, Md.; cat no. 50-82-01) was added to each well and the plates were incubated for 2 h at RT. At the end of the incubation, the solution was aspirated and the plates were stored in foil pouches with desiccant at −80° C.

On the day of the assay, sixteen NOV004, NOV005, and NOV006 standard concentrations, ranging from 0.244-4000 pM, were prepared by serial dilution in Casein buffer, including a buffer negative control. All study samples were diluted 1:50 manually in Casein buffer and then serially diluted 5-fold using a Biomek Fx for a total of three dilutions. The plates were incubated for 2 h at RT and then washed 3 times with phosphate wash buffer (90 µL/well). HRP-labeled goat anti-human-IgG (400 ng/mL in Casein buffer, 30 µL/well) was added to each plate and the plates were incubated for 1 h at RT. The plates were washed 3 times with phosphate wash buffer (90 µL/well), and then KPL LumiGLO Chemiluminescent Substrate was added (30 µL/well; cat no. 54-61-00). Chemiluminescence was read immediately on a SpectraMax M5 plate reader (Molecular Devices) at all wavelengths with 50 ms integration time. Human Fc concentrations (pM) in plasma samples were interpolated from the NOV004, NOV005, or NOV006 standard curves, multiplied by dilution factors, and converted to nM concentrations.

Figure 5A:
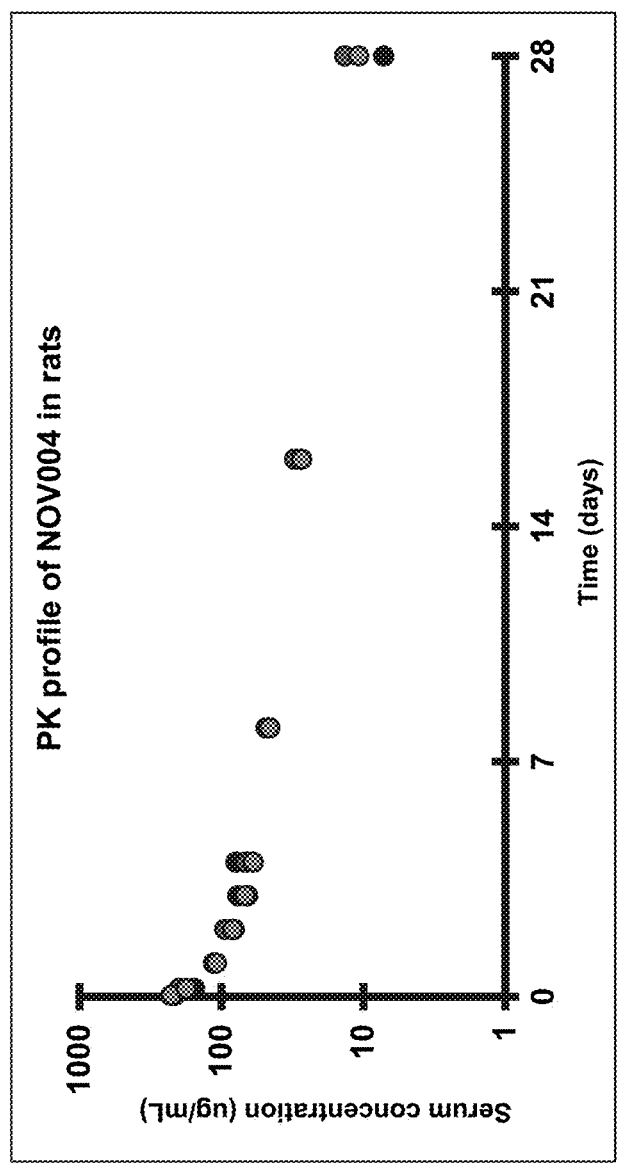
FIG. 5A-FIG. 5C: NOV004, NOV005, and NOV006 concentration-time profiles following IV injection in rats. Animals exhibited mean $C_{max}$ of approximately 200 µg/mL at 1 h after IV administration of NOV004 (FIG. 5A), NOV005 (FIG. 5B), or NOV006 (FIG. 5C), with all three antibodies showing comparable PK profiles.
Figure 5B:
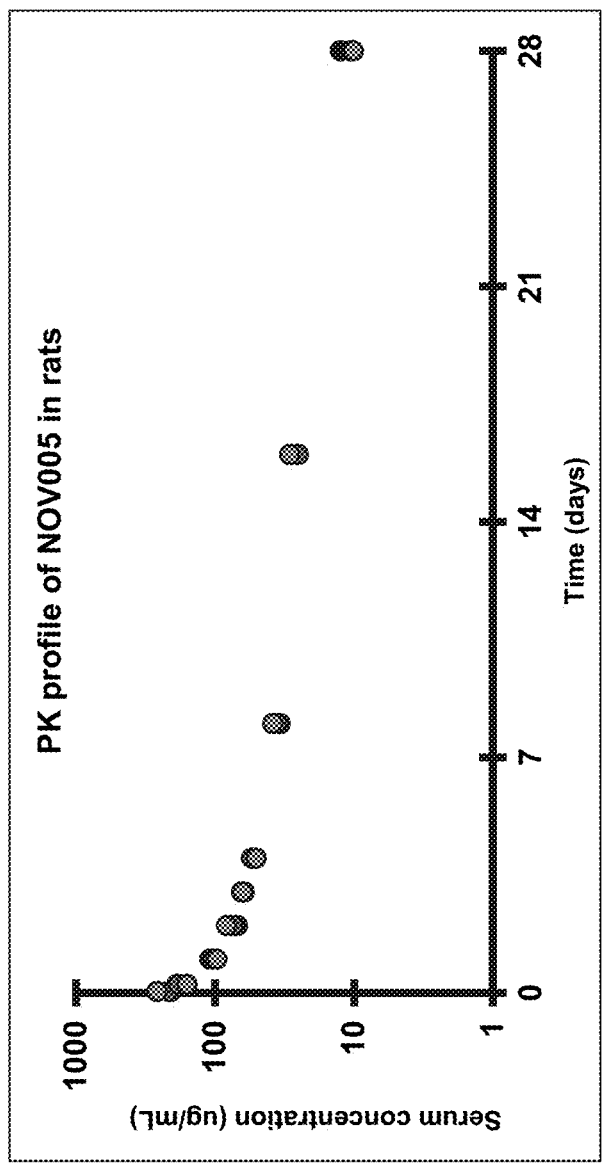
Figure 5C:
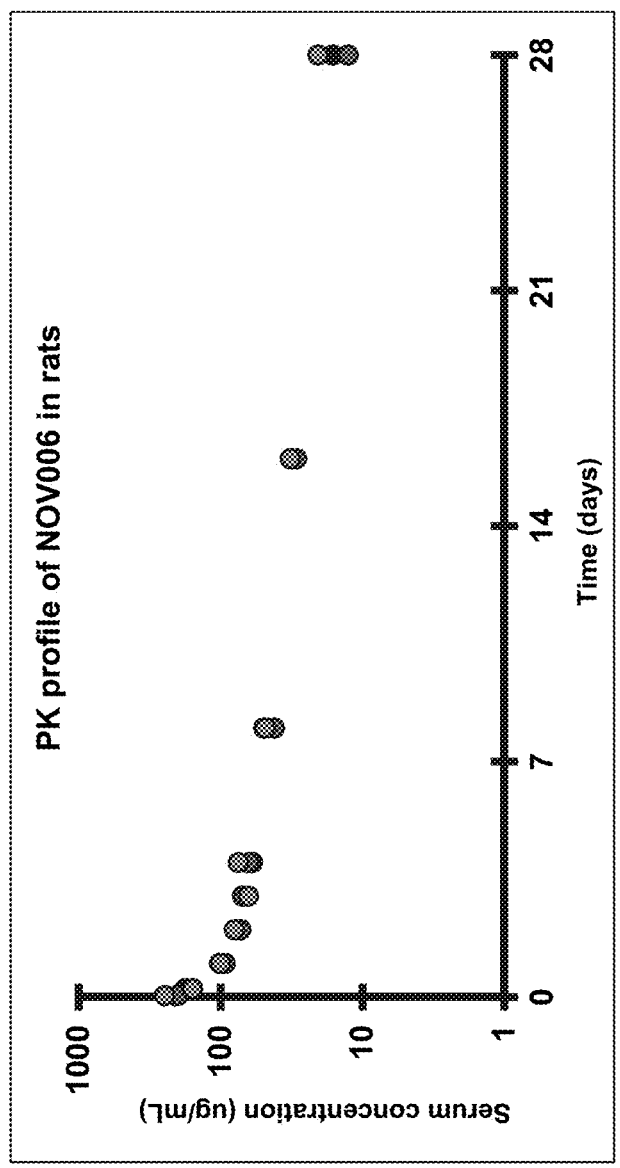

Animals exhibited mean $C_{max}$, of approximately 200 µg/mL at 1 h after IV administration of NOV004, NOV005, or NOV006. NOV004. NOV005, and NOV006 exhibited equivalent PK profiles in Sprague-Dawley rats (FIG. 5).

Example 4: Developability and Formulation Assessments

Production process and formulation studies for antibodies NOV004, NOV005, and NOV006 were carried out. The observed formation of high molecular weight species (HMW) during previous assessments of NOV004 suggested a high degree of aggregation in solution and prompted the development and assessment of other FGF21 mimetic antibodies which have comparable functional activities but better production and formulation profiles, e.g., none to little (e.g., less than 20%, less than 15%, less than 10%, or less than 5%) observed formation of HMW.

DNA sequences coding for antibodies NOV005 and NOV006, including codon optimization for homosapiens, were ordered at GeneArt™ (Life Technologies Inc. Regensburg, Germany) and ATUM (Menlo Park, Calif.). Vectors expressing NOV004, NOV005 and NOV006 were linearized and transfected into a CHO cell line. Pools were selected using 10 nM methotrexate (MTX) until recovered to >95% viability. One pool for each molecule was selected for wave production and scaled up appropriately. Culture supernatant from the wave production were harvested after 13 days and filtered.

The wave harvest material of NOV005 and NOV006 was processed using two column chromatography purification process for standard antibodies—captured using affinity chromatography (resin—GE Healthcare MabSelect SuRe) and polish using cation exchange chromatography (CEC) (resin—Fractogel EMD SO3-). The captured material was subject to Viral Inactivation (adjustment of pH to 3.5, incubation at this pH at room temperature for 70 min followed by adjustment of pH to 5.0) and sterile filtration before processing through CEC. After CEC, the material was diafiltered to buffer exchange into 10 mM Histidine/Histidine-HCl, pH 5.0 using tangential flow filtration. Subsequently, the material was concentrated to about 200 mg/mL to provide material for formulation studies. For example, the antibodies were assessed in formulation buffers, and certain parameters were determined, in particular, formation of HMW after 4 weeks at 40° C. Table 3 below summarizes data from an exemplary experiment assessing the formation of HMW observed in samples of NOV004, NOV005, and NOV006 after 4 weeks at 40° C.

TABLE 3

High molecular weight species (HMW) formation

| | | | % HMW (Absolute value) | |
|---|---|---|---|---|
| Molecule | Concentration (mg/mL) | Formulation | $T_0$ | 4 weeks at 40° C. |
| NOV004 | 150 | 20 mM Hist/HCl, 220 mM Sucrose, 0.04% PS20, pH 5.5 | n.a | n.a |
| | | 20 mM Hist/HCl, 220 mM sucrose, 0.04% PS20, pH 6.5 | 1.2 | 64 |
| NOV005 | 150 | 20 mM Hist/HCl, 220 mM Sucrose, 0.04% PS20, pH 5.5 | 0.2 | 0.8 |
| | | 20 mM Hist/HCl, 220 mM sucrose, 0.04% PS20, pH 6.5 | 0.2 | 0.6 |
| NOV006 | 150 | 20 mM Hist/HCl, 220 mM Sucrose, 0.04% PS20, pH 5.5 | <LOQ | 0.7 |
| | | 20 mM Hist/HCl, 220 mM sucrose, 0.04% PS20, pH 6.5 | <LOQ | 0.6 |

LOQ = limit of quantification

The differences in sequences of NOV005 and NOV006, relative to NOV004, conferred significant improvement in the formation of HMW upon storage. Both NOV005 and NOV006 exhibited approximately less than 1% HMW formation at 40° C. for 4 week, while NOV004 exhibited much higher HMW formation, approximately 64% HMW formation at 40° C. for 4 week.

Sequence alignment of the VH and VL of NOV005 and NOV004 is provided below:

```
VH
Identity: 79.2
Similarity: 88.3%
NOV005    1 QVQLQESGPGLVKPSQTLSLTCTVSGYSITSGYTWHWIRQHPGKGLEWIG    50
            :|||.|||.|||||..:|.|:|.||||||||||||||:||.|||||||:.
NOV004    1 EVQLVESGGGLVKPGGSLRLSCAVSGYSITSGYTWHWVRQAPGKGLEWLS    50

NOV005   51 YIHYSVYTNYNPSLKSRVTISRDTSKNQFSLKLSSVTAADTAVYYCARRT   100
            ||||||||||||:|.|.||||||:||.|.|:::|:.|.||||||||||
NOV004   51 YIHYSVYTNYNPSVKGRFTISRDTAKNSFYLQMNSLRAEDTAVYYCARRT   100

NOV005  101 TSLERYFDVWGQGTLVTVSS                                120
            ||||||||||||||||||||
NOV004  101 TSLERYFDVWGQGTLVTVSS                                120

VL
Identity: 99.1%
Similarity: 100.0%
NOV005    1 DIQMTQSPSSLSASVGDRVTITCQASQDISNYLNWYQQKPGKAPKLLIYY    50
            ||||||||||||||||||||||||||||||||||||||||||||||||||
NOV004    1 DIQMTQSPSSLSASVGDRVTITCQASQDISNYLNWYQQKPGKAPKLLIYY    50

NOV005   51 TSRLQSGVPSRFSGSGSGADYTFTISSLQPEDIATYFCQQGNTLPYTFGQ   100
            ||||||||||||:|||||||||||||||||||||||||||||||||||||
NOV004   51 TSRLQSGVPSRFTGSGSGADYTFTISSLQPEDIATYFCQQGNTLPYTFGQ   100

NOV005  101 GTKLEIK                                             107
            |||||||
NOV004  101 GTKLEIK                                             107
```

This data show that NOV005 and NOV006 surprising exhibited minimal aggregation tendencies as indicated by formation of HMW in contrast to NOV004, and suggest that NOV005 and NOV006 exhibit characteristics suitable, and would be more preferable, for a pharmaceutical formulation.

Example 5: Study in Obese, Cynomolgus Monkeys

The effects of FGF21 mimetic mAbs, such as NOV004, NOV005, or NOV006, on food consumption, body weight, and plasma biomarkers in obese cynomolgus monkeys are studied.

Exemplary Protocols:

Five male cynomolgus monkeys are treated with two subcutaneous (s.c.), 1 mg/kg doses of FGF21 mimetic mAbs, such as NOV004, NOV005, or NOV006 to be administered one week apart (study days 0 and 7) and food consumption, body weights, and plasma biomarkers are assessed for more than 100 days post-dose. For each dose, animals are restrained in their home cage, blood samples are collected, and then each animal is given a subcutaneous dose of 1 mg/kg FGF21 mimetic mAbs, such as NOV004, NOV005, or NOV006. Food consumption measurements start 1 week before the first dose and continues through the study. The study diet is weighed prior to feeding and is divided into two equal portions for each day. The following morning, remaining diet is collected and weighed. The number of pellets (1 g each) dropped in the catch pan are counted and are added to the weight of the remaining food. Daily food consumption is calculated as the weight of food provided minus food collected. Fruit and vegetable consumption are not measured. Non-fed body weights are measured in duplicate three mornings per week (prior to blood collection or dosing) using the dynamic feature on the scale.

Measurement of Plasma FGF21 Mimetic mAb Concentrations

Human Fc IgG in cynomologus monkey plasma is quantified using an ELISA based sandwich immunoassay. Anti-human-IgG mouse IgG1, a mouse monoclonal antibody against human IgG, is used as the capture antibody. White, Greiner, 384-well plates are coated with 2 µg/mL anti-human-IgG mouse IgG1 (30 µL/well) and are incubated overnight at room temperature (RT). Coating antibody is aspirated and 1× milk blocker (KPL #50-82-01) is added at 90 µL/well for 2 h at RT. The blocking solution is aspirated and the plates are stored at −80° C. in plate bags with desiccant until assay. On the day of the assay, plates and reagents are brought to RT. Standards are made by diluting the purified IgG from 4000 to 16 pM in custom casein sample diluent and including a buffer control. Samples are diluted in duplicate 1:50, 1:250, 1:1250, and 1:6250 in the same diluent as standards, and then standards, diluted samples, and controls are added to the plate for 2 h at RT (working volume for all steps was 30 µL/well). Plates are then washed 3 times with a phosphate based wash buffer. Horseradish peroxidase (HRP)-labeled anti-human Fc-gamma antibody is added to the plate for 1 hour at RT, and then the plates are washed 3 times with a phosphate-based wash buffer. Chemiluminescent substrate is added to the plate and the plate is immediately read on a luminescence plate reader.

FGF21 mimetic mAb, e.g., NOV004, NOV005 or NOV006, standards are assayed in triplicate per plate. Diluted plasma samples are assayed in duplicate. Unknown samples are interpolated from the IgG standard curve. Curve fitting, back-calculation, % recovery, and interpolation of sample concentrations are performed using SoftMax Pro Software v5.4.1. Signal generated by the IgG standards was plotted and fit using a 4-parameter logistical curve-fitting option. Fc concentrations (pM) in plasma samples are interpolated from the FGF21 mimetic mAb standard curve and multiplied by dilution factors. The assay lower limit of quantification (LLOQ) and the upper limit of quantification (ULOQ) are determined. LLOQ and ULOQ are defined as the lower and upper standard concentration with 100% recovery ±20% and CV<20% and then multiplied by the dilution factors.

Detection of Anti-Drug Antibodies

Plasma samples are diluted 1:5 in LowCross Buffer (Boca Scientific; Boca Raton, Fla.; cat no. 100 500). Reaction Mixture is prepared containing 0.6 µg/mL of biotin-labeled FGF21 mimetic mAb and 0.6 µg/mL of digoxigenin-labeled FGF21 mimetic mAb in LowCross Buffer. Diluted plasma (80 µL) is combined with 160 µL of Reaction Mixture in 96-well U-bottom plates (BD Falcon; Billerica, Mass.; cat no. 351177). The edges of the plates are sealed with Parafilm and the plates are incubated on a shaking platform at 37° C. for 2 h (150 rpm, protected from light). An aliquot of each mixture (100 µL) is then transferred to duplicate wells of Streptavidin-coated 96-well plates (Roche; cat no. 11734776001), which are first washed 3 times with wash buffer consisting of 1×PBS containing 0.05% (v/v) Tween-20 (300 µL per well). The plates are sealed and then incubated at RT on a shaking platform for 1 h (300 rpm, protected from light). Plates are washed 3 times with wash buffer (300 µL per well), and then 100 µL of anti-digoxigenin peroxidase_POD Fab fragment (Roche; cat no. 11633716001) diluted 1:2500 in LowCross Buffer are added to each well. The plates are sealed, are incubated at RT on a shaking platform for 45 minutes (300 rpm, protected from light), and then are washed 3 times with wash buffer (300 µL per well). TMB One Component HRP Microwell Substrate (Bethyl Laboratories; Montgomery Tex.; cat no. E102; 100 µL/well) is added to each well and blue color was developed for 9-10 min., protected from light. The color reaction is stopped by adding 100 µL of 0.18 N $H_2SO_4$ to each well, the plates are shaken briefly, and yellow color is measured at $OD_{450}$.

Measurement of Plasma Glucose Concentrations

Plasma glucose concentrations are measured using an Autokit Glucose assay (Wako Chemicals; Richmond, Va.; catalog no. 439-90901). A standard curve is prepared by diluting the calibrator to 500, 200, 100, 50, 20, and 0 mg/dL standards. Assay reagent (300 µL), pre-warmed to 37° C., is added to 2 µL of plasma, standards, and control samples in a clear, flat-bottom, 96-well plate (Thermo Scientific; cat no. 269620). The plate is mixed on a plate shaker for 30 s and then incubated at 37° C. for 5 min. Following a 20 s mix, the plate is read at 505/600 nm using a Molecular Devices SPECTRAmax PLUS 384 (Sunnyvale, Calif.). Sample glucose concentrations are calculated by comparing to the standard curve.

Measurement of Plasma Insulin Concentrations

Plasma insulin concentrations are determined using the Millipore Human Insulin Specific RIA Kit (Billerica, Mass.; cat no. HI-14K) according to the manufacturer instructions. Appropriate amounts of assay buffer, standards, or diluted plasma sample are mixed with $^{125}$I-insulin and anti-insulin antibody in 5 mL, 75×12 mm PP SARSTEDT tubes (catalog no. 55.526). The tubes are vortexed, covered, and incubated for 20 h at RT. After the incubation, 1 mL of 4° C. precipitating reagent is added and the tubes are vortexed and incubated for 30 min. at 4° C. All tubes are centrifuged for 30 min (3000 rpm at 4° C.), the supernatants are decanted, and the pellets are counted on a PerkinElmer WIZARD2 Automatic Gamma Counter (model no. 2470; PerkinElmer; Waltham, Mass.). Insulin concentrations are calculated by comparing to a standard curve generated using known quantities of insulin.

Measurement of Plasma Triglyceride Concentrations

Plasma triglyceride (TG) concentrations are measured using the Triglyceride (GPO) Liquid Reagent set (Pointe Scientific; Canton, Mich.; cat no. T7532-500). Pre-warmed assay reagent (300 µL, 37° C.) is added to 5 µL of plasma in a clear, flat-bottom, 96-well plate (Thermo Fisher Scientific; Tewksbury, Mass.; cat no. 269620). The plate is mixed on a plate shaker for 30 s and then is placed in an incubator at 37° C. for 5 min. Following a 20 s mix, absorbance is measured at 500 nm with a SPECTRAmax PLUS plate reader. TG concentrations are calculated by comparing to a calibration curve generated using known quantities of a TG standard (Pointe Scientific; cat no. T7531-STD).

Measurement of Plasma Cholesterol Concentrations:

Plasma total cholesterol (TC) is quantified using the Cholesterol (Liquid) Reagent Set, (Pointe Scientific; cat no. C7510-500). Pre-warmed assay reagent (200 µL, 37° C.) is added to 10 µL of plasma in a clear, flat-bottom, 96-well assay plate (Thermo Fisher Scientific; cat no. 269620). The plate is mixed on a plate shaker for 30 s and then incubated at 37° C. for 5 min. Following a 20 s mix, absorbance is measured at 500 nm in a SPECTRAmax PLUS plate reader. Cholesterol concentrations are calculated by comparing to a calibration curve generated using known quantities of a cholesterol standard (Stanbio Laboratory; Boerne, Tex.; cat no. 1012-030).

Measurement of Plasma High-Density Lipoprotein Cholesterol Concentrations

For determination of high-density lipoprotein (HDL) cholesterol concentrations, 50 µL of plasma sample is combined with 50 µL of Cholesterol Precipitating Reagent (Wako Chemicals; Richmond, Va.; cat no. 431-52501) in a 0.5 mL microcentrifuge tube and is vortexed briefly. The tube is placed at room temperature for 10 min and then is centrifuged at 2000×g for 10 min at 4° C. Following centrifugation, approximately half of the supernatant (containing the HDL cholesterol portion of the original plasma sample) is removed and 10 µL is used for the cholesterol assay described above.

Measurement of Plasma β-Hydroxybutyrate Concentrations

Plasma β-hydroxybutyrate (β-HB) concentrations are measured using the β-Hydroxybutyrate LiquiColor Test kit (Stanbio Laboratory; cat no. 2440-058). Assay reagent R1 (215 µL pre-warmed to 37° C.) is added to 20 µL of quality control or plasma sample in a clear, flat-bottom, 96-well plate (Thermo Fisher Scientific; cat no. 269620). The plate is mixed on a plate shaker for 30 s and is then placed in an incubator at 37° C. for 5 min. Pre-read absorbance is measured at 505 nm in a SPECTRAmax PLUS plate reader. Assay reagent R2 (35 µL pre-warmed to 37° C.) is added to each well, and the plate is again mixed on a plate shaker for 30 s and is incubated at 37° C. for 5 min. Following a 20 s mix, final absorbance is measured at 505 nm from which the pre-read value was subtracted. β-HB concentrations are calculated by comparing to a calibration curve generated using known quantities of a β-HB calibrator (Wako Diagnostics; Richmond, Va.; cat no. 412-73791).

Statistical Analyses

Statistical analyses are performed using GraphPad Prism (Version 6.05; GraphPad Software; La Jolla, Calif.). Food intake data for each animal are normalized as a percent of baseline (calculated as the mean of days −6 to 0) and then group means±standard errors of the mean (SEM) are calculated; each day is compared to day 0 by nonparametric Friedman's test with Dunn's multiple comparisons post-test. Body weights are presented as group means±standard errors of the mean (SEM) calculated as percent of baseline (calculated as the mean of days −7, −5, −3, and 0). Raw body weight and plasma biomarker data are also analyzed by nonparametric Friedman's test with Dunn's multiple comparisons post-test. $P<0.05$ is considered significant.

Example 6: Study in Obese, Cynomolgus Monkeys

Figure 6A:
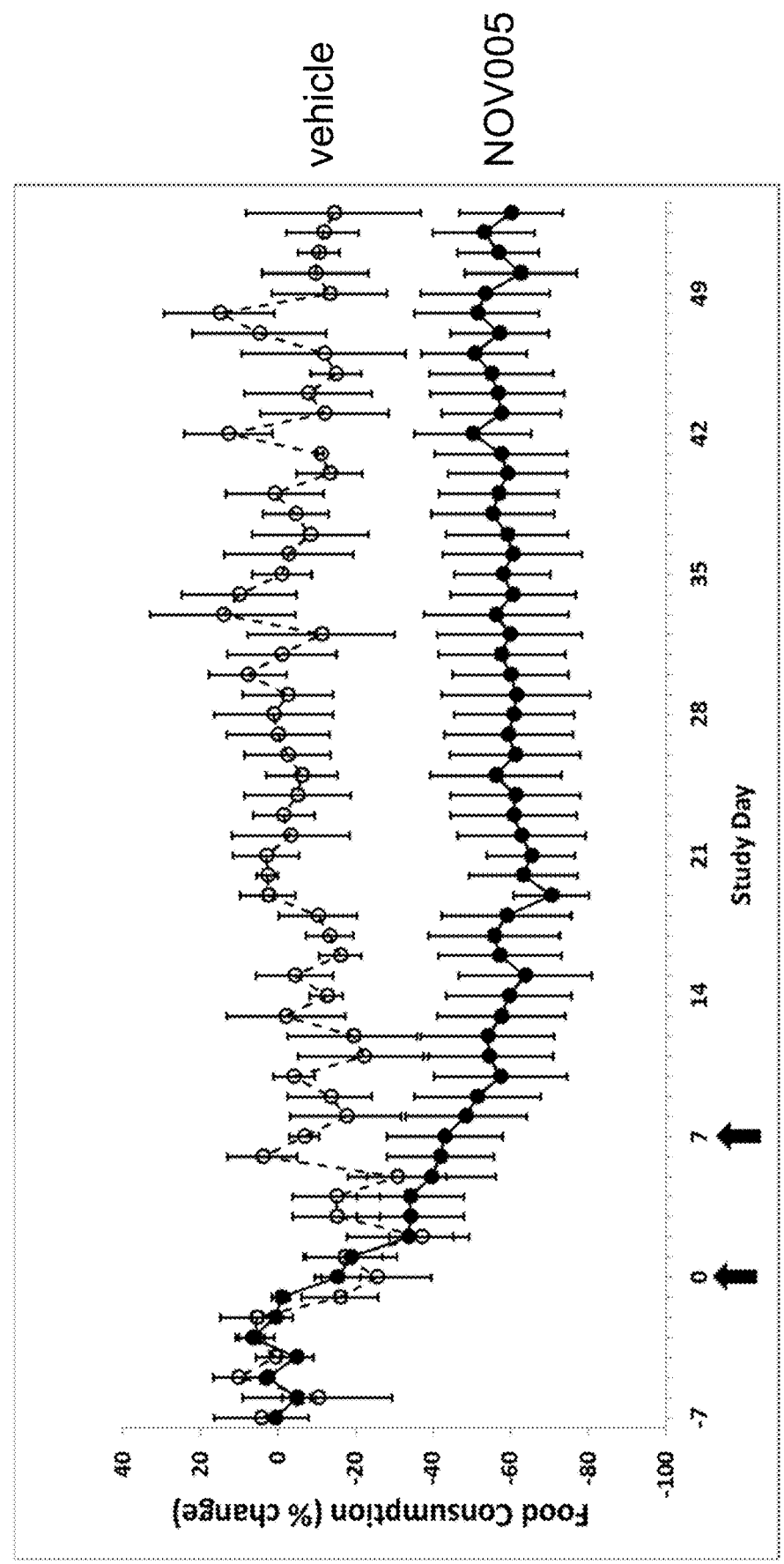
FIG. 6A: Two subcutaneous 1 mg/kg doses of NOV005 (n=5 animals) or vehicle (n=3 animals) were administrated to male normoglycemic obese cynomolgus monkeys one week apart (days of dosing indicated by arrows). Food consumption data for standard chow was normalized as a percent of baseline with group mean±SEM. Monkeys consumed fruit, vegetables and peanuts as treats throughout the study.
Figure 6B:
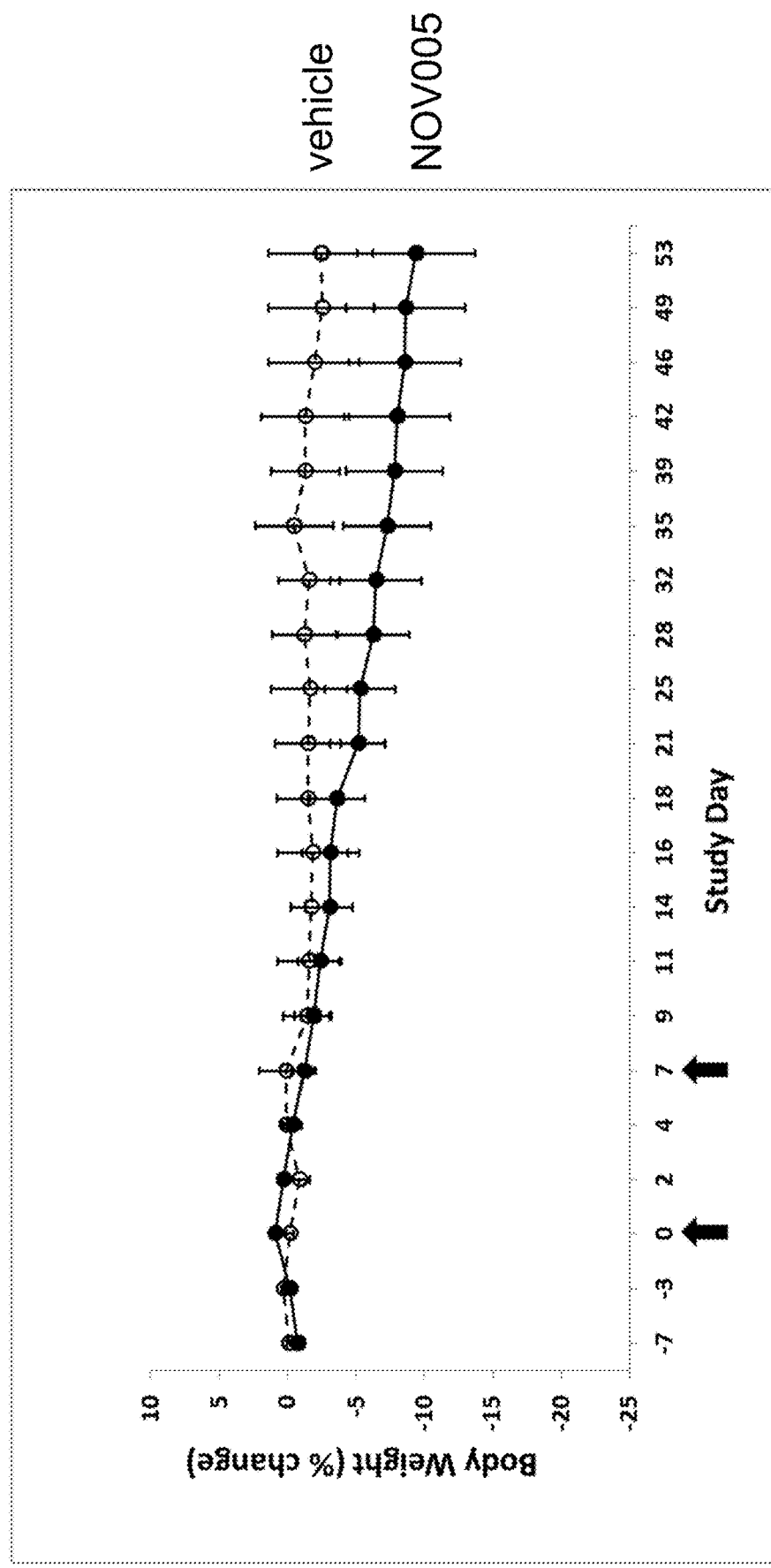
FIG. 6B: Two subcutaneous 1 mg/kg doses of NOV005 (n=5 animals) or vehicle (n=3 animals) were administrated to male normoglycemic obese cynomolgus monkeys one week apart (days of dosing indicated by arrows). Baseline body weights for NOV005 and vehicle treated animals were 11.3+1.2 and 11.4+1.3 kg, respectively. Body weight data was normalized as a percent of baseline with (A) group mean±SEM and (B) individual animal data shown.

To assess the effects of NOV005 in male normoglycemic obese cynomolgus monkeys, two subcutaneous 1 mg/kg doses of NOV005 (n=5 animals) or vehicle (n=3 animals) were administered one week apart. Interim study results are summarized below:

NOV005 decreased food consumption of standard chow, with a peak mean reduction of about 60% compared to baseline (FIG. 6A) and a mean peak weight reduction of about 10% compared to baseline in NOV005 treated animals (FIG. 6B)

Plasma from non-fasted animals was analyzed for changes in biomarkers of lipid and carbohydrate metabolism:

A mean decrease of about 65% was observed for plasma TG levels in NOV005 treated animals compared to baseline at day 35

NOV005 also decreased total cholesterol and insulin compared to baseline at day 35, but these changes were not statistically significant Other biomarkers that will be measured at the end of the study include adiponectin, p-hydroxybutyrate, ApoCIII, HDL-C and lipoprotein profiles

TABLE 4

NOV005 improved plasma biomarker levels in obese cynomolgus monkeys

| Biomarker[1] | Baseline[2] | Day 35 | Mean %Δ[3] |
| --- | --- | --- | --- |
| Triglycerides (mg/dL) | 177 ± 13 | 47 ± 15 | −65 ± 12* |
| Total cholesterol (mg/dL) | 108 ± 2 | 90 ± 9 | −17 ± 6 |
| Glucose (mg/dL) | 64 ± 4 | 66 ± 9 | 3 ± 7 |
| Insulin (µU/mL) | 212 ± 33 | 29 ± 7 | −54 ± 15 |

Values represent group means ± SEM.

[1]Blood was collected from non-fasted animals for biomarker measurements.

[2]Baseline values reflect the mean of days −7, −3 and 0.

[3]Percent change was calculated for each individual and then averaged for group mean ± SEM.

*$P < 0.05$ vs baseline by nonparametric Friedman test with Dunn's post-test.

INCORPORATION BY REFERENCE

All references cited herein, including patents, patent applications, papers, text books, and the like, and the references cited therein, to the extent that they are not already, are hereby incorporated herein by reference in their entirety.

The invention claimed is:

1. A nucleic acid coding for an antibody or antigen-binding fragment thereof that binds to β-klotho comprising the nucleotide sequences encoding the heavy chain variable region as set forth in SEQ ID NOs: 16, 36, or 38; and the light chain variable region as set forth in SEQ ID Nos: 54, 27, 33, or 40.

2. The nucleic acid of claim 1, wherein the nucleotide sequences encode the heavy chain as set forth in SEQ ID Nos: 18, 37, 30, or 39; and the light chain as set forth in SEQ ID Nos: 29, 51, 35 or 41.

3. A vector comprising the nucleic acid according to claim 1.

4. A host cell comprising the vector of claim 3.

5. A method of making an antibody or antigen-binding fragment thereof which binds β-klotho, comprising the steps of:
culturing the host cell of claim 4 under conditions suitable for expression of the antibody or an antigen-binding fragment thereof, wherein the antibody or antigen-binding fragment thereof comprises a heavy chain variable region and a light chain variable region which can be assembled; and
isolating and/or purifying said antibody or antigen-binding fragment thereof from the culture medium.

6. The nucleic acid of claim 1, comprising the nucleotide sequences in the heavy chain variable region as set forth in SEQ ID NOs: 16 or 36; and in the light chain variable region as set forth in SEQ ID Nos: 54 or 27.

7. A method of making an antibody or antigen-binding fragment thereof which binds β-klotho, comprising the steps of:
culturing the host cell of claim 6 under conditions suitable for expression of the antibody or an antigen-binding fragment thereof, wherein the antibody or antigen-binding fragment thereof comprises a heavy chain variable region and a light chain variable region which can be assembled; and
isolating and/or purifying said antibody or antigen-binding fragment thereof from the culture medium.

8. The nucleic acid of claim 1, comprising the nucleotide sequences in the heavy chain variable region as set forth in SEQ ID NOs: 16 or 38; and in the light chain variable region as set forth in SEQ ID Nos: 33 or 40.

9. A method of making an antibody or antigen-binding fragment thereof which binds β-klotho, comprising the steps of:
culturing the host cell of claim 8 under conditions suitable for expression of the antibody or an antigen-binding fragment thereof, wherein the antibody or antigen-binding fragment thereof comprises a heavy chain variable region and a light chain variable region which can be assembled; and
isolating and/or purifying said antibody or antigen-binding fragment thereof from the culture medium.

10. The nucleic acid of claim 1, comprising the nucleotide sequence in the heavy chain region as set forth in SEQ ID Nos: 18 or 37; and in the light chain region as set forth in SEQ ID Nos: 29 or 51.

11. A method of making an antibody or antigen-binding fragment thereof which binds β-klotho, comprising the steps of:
culturing the host cell of claim 10 under conditions suitable for expression of the antibody or an antigen-binding fragment thereof, wherein the antibody or antigen-binding fragment thereof comprises a heavy chain variable region and a light chain variable region which can be assembled; and isolating and/or purifying said antibody or antigen-binding fragment thereof from the culture medium.

12. The nucleic acid of claim 1, comprising the nucleotide sequence in the heavy chain region as set forth in SEQ ID Nos: 30 or 39; and in the light chain region as set forth in SEQ ID Nos: 35 or 41.

13. A method of making an antibody or antigen-binding fragment thereof which binds β-klotho, comprising the steps of:

culturing the host cell of claim 12 under conditions suitable for expression of the antibody or an antigen-binding fragment thereof, wherein the antibody or antigen-binding fragment thereof comprises a heavy chain variable region and a light chain variable region which can be assembled; and isolating and/or purifying said antibody or antigen-binding fragment thereof from the culture medium.

* * * * *